US011319593B2

(12) United States Patent
Toung et al.

(10) Patent No.: US 11,319,593 B2
(45) Date of Patent: May 3, 2022

(54) DISTINGUISHING METHYLATION LEVELS IN COMPLEX BIOLOGICAL SAMPLES

(71) Applicant: Illumina, Inc., San Diego, CA (US)

(72) Inventors: Jonathan Toung, San Diego, CA (US); Li Liu, San Diego, CA (US); Min-Jui Richard Shen, Rancho Santa Fe, CA (US); Ruoyu Zhang, Ithaca, NY (US)

(73) Assignee: Illumina, Inc., San Diego, CA (US)

( * ) Notice: Subject to any disclaimer, the term of this patent is extended or adjusted under 35 U.S.C. 154(b) by 809 days.

(21) Appl. No.: 15/380,348

(22) Filed: Dec. 15, 2016

(65) Prior Publication Data

US 2017/0175205 A1     Jun. 22, 2017

Related U.S. Application Data

(60) Provisional application No. 62/268,961, filed on Dec. 17, 2015, provisional application No. 62/401,591, filed on Sep. 29, 2016.

(51) Int. Cl.
| | |
|---|---|
| *C12Q 1/6886* | (2018.01) |
| *G16B 25/10* | (2019.01) |
| *G16B 20/10* | (2019.01) |
| *G16H 50/30* | (2018.01) |
| *G16B 40/00* | (2019.01) |
| *G16B 99/00* | (2019.01) |

(52) U.S. Cl.
CPC ........... *C12Q 1/6886* (2013.01); *G16B 20/10* (2019.02); *G16B 25/10* (2019.02); *G16B 40/00* (2019.02); *G16B 99/00* (2019.02); *G16H 50/30* (2018.01); *C12Q 2600/154* (2013.01)

(58) Field of Classification Search
None
See application file for complete search history.

(56) References Cited

U.S. PATENT DOCUMENTS

| | | |
|---|---|---|
| 5,599,675 A | 2/1997 | Brenner |
| 5,750,341 A | 5/1998 | Macevicz |
| 5,786,146 A | 7/1998 | Herman et al. |
| 6,023,540 A | 2/2000 | Walt et al. |
| 6,200,737 B1 | 3/2001 | Walt et al. |
| 6,210,891 B1 | 4/2001 | Nyren et al. |
| 6,251,594 B1 | 6/2001 | Gonzalgo et al. |
| 6,258,568 B1 | 7/2001 | Nyren |
| 6,265,171 B1 | 7/2001 | Herman et al. |
| 6,274,320 B1 | 8/2001 | Rothberg et al. |
| 6,327,410 B1 | 12/2001 | Walt et al. |
| 6,331,393 B1 | 12/2001 | Laird et al. |
| 6,355,431 B1 | 3/2002 | Chee et al. |
| 6,429,027 B1 | 8/2002 | Chee et al. |
| 6,890,741 B2 | 5/2005 | Fan et al. |
| 6,913,884 B2 | 7/2005 | Stuelpnagel et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,582,420 B2 | 9/2009 | Oliphant et al. |
| 7,611,869 B2 | 11/2009 | Fan |
| 2002/0102578 A1 | 8/2002 | Dickinson et al. |
| 2003/0170684 A1 | 9/2003 | Fan |
| 2005/0053980 A1 | 3/2005 | Gunderson et al. |
| 2005/0181440 A1 | 8/2005 | Chee et al. |
| 2008/0108082 A1 | 5/2008 | Rank et al. |
| 2008/0166728 A1 | 7/2008 | Kruglyak et al. |
| 2009/0026082 A1 | 1/2009 | Rothberg et al. |
| 2009/0127589 A1 | 5/2009 | Rothberg et al. |
| 2009/0186349 A1 | 7/2009 | Gunderson et al. |
| 2010/0137143 A1 | 6/2010 | Rothberg et al. |

(Continued)

FOREIGN PATENT DOCUMENTS

| | | |
|---|---|---|
| EP | 1 342 794 A1 | 9/2003 |
| WO | WO 89/10977 A1 | 11/1989 |

(Continued)

OTHER PUBLICATIONS

Schwarzenbach et al. Cell-free nucleic acids as biomarkers in cancer patients. Nature Reviews Cancer, vol. 11, pp. 426-437 (Year: 2011).*
Hirst, Martin. "Epigenomics: sequencing the methylome." In Array Comparative Genomic Hybridization, pp. 39-54. Humana Press, Totowa, NJ, 2013. (Year: 2013).*
Lee et al. Analyzing the cancer methylome through targeted bisulfite sequencing. Cancer Letters 2013, vol. 340, pp. 171-178 (Year: 2013).*
Ushijima et al. Treatment for Recurrent Ovarian Cancer—At first relapse. Journal of Oncology 2010, pp. 1-7 (Year: 2010).*

(Continued)

*Primary Examiner* — Olivia M. Wise
(74) *Attorney, Agent, or Firm* — Mueting Raasch Group

(57) ABSTRACT

Provided herein is a method for distinguishing an aberrant methylation level for DNA from a first cell type, including steps of (a) providing a test data set that includes (i) methylation states for a plurality of sites from test genomic DNA from at least one test organism, and (ii) coverage at each of the sites for detection of the methylation states; (b) providing methylation states for the plurality of sites in reference genomic DNA from one or more reference individual organisms, (c) determining, for each of the sites, the methylation difference between the test genomic DNA and the reference genomic DNA, thereby providing a normalized methylation difference for each site; and (d) weighting the normalized methylation difference for each site by the coverage at each of the sites, thereby determining an aggregate coverage-weighted normalized methylation difference score. Also provided herein are sensitive methods for using genomic DNA methylation levels to distinguish cancer cells from normal cells and to classify different cancer types according to their tissues of origin.

14 Claims, 9 Drawing Sheets

Specification includes a Sequence Listing.

(56) References Cited

U.S. PATENT DOCUMENTS

| | | |
|---|---|---|
| 2010/0282617 A1 | 11/2010 | Rothberg et al. |
| 2013/0189684 A1 | 7/2013 | Ehrich et al. |
| 2013/0275486 A1 | 10/2013 | Dickinson et al. |
| 2014/0080715 A1 | 3/2014 | Lo et al. |
| 2014/0214579 A1 | 7/2014 | Shen et al. |

FOREIGN PATENT DOCUMENTS

| | | |
|---|---|---|
| WO | WO 91/06678 A1 | 5/1991 |
| WO | WO 99/18434 A1 | 4/1998 |
| WO | WO 98/40726 A1 | 9/1998 |
| WO | WO 98/50782 A2 | 11/1998 |
| WO | WO 02/086163 A1 | 10/2002 |
| WO | WO 02/086163 A8 | 10/2002 |
| WO | WO 2004/018497 A2 | 3/2004 |
| WO | WO 2004/051224 A2 | 6/2004 |
| WO | WO 2007/123744 A2 | 11/2007 |
| WO | WO 2013/174432 A1 | 11/2013 |
| WO | WO 2014/043763 A1 | 3/2014 |

OTHER PUBLICATIONS

Invitation to Pay Additional Fees, PCT/US2016/066901, 10 pages, dated Mar. 31, 2017.
International Search Report and Written Opinion, PCT/US2016/066901, 26 pages, dated Jun. 2, 2017.
Assenov et al., "Comprehensive analysis of DNA methylation data with RnBeads", Nature Methods, Nov. 2014; 11(11):1138-1145.
Bains et al., "A novel method for nucleic acid sequence determination," Journal of Theoretical Biology, Dec. 1988; 135(3):303-7.
Baylin et al., "DNA hypermethylation in tumorigenesis: epigenetics joins genetics," Trends Genet., Apr. 2000; 16(4):168-174.
Bentley et al., "Accurate whole human genome sequencing using reversible terminator chemistry," Nature, Nov. 2008; 456(7218):53-59.
Bestor, "Gene silencing. Methylation meets acetylation," Nature, May 1998; 393(6683):311-312.
Bock, "Analysing and interpreting DNA methylation data", Nature Reviews Genetics, Oct. 2012; 13(10):705-719.
Cancer Genome Atlas Research Network et al., "The Cancer Genome Atlas Pan-Cancer analysis project," Nature Genetics., Oct. 2013; 45(10):1113-1120.
Chan et al., "Bioinformatics analysis of circulating cell-free DNA sequencing data", Clinical Biochemistry, May 2015; 48(15):962-975.
Cox et al. "Drugging the undruggable RAS: Mission possible?" Nature Reviews Drug Discovery, Nov. 2014; 13(11):828-51.
Danese et al., "Comparison of Genetic and Epigenetic Alterations of Primary Tumors and Matched Plasma Samples in Patients with Colorectal Cancer," PLoS ONE, May 2015; 10(5):e0126417. doi:10.1371/journal.pone.0126417.
Diaz et al., "The molecular evolution of acquired resistance to targeted EGFR blockade in colorectal cancers," Nature, Jun. 2012; 486(7404):537-540.
Dragich et al., "Rett syndrome: a surprising result of mutation in MECP2," Hum Mol Genet., Oct. 2000; 9(16):2365-2375.
Drmanac et al., "Accurate sequencing by hybridization for DNA diagnostics and individual genomics," Nature Biotechnology, Jan. 1998; 16(1):54-58.
Eads et al., "CpG Island Hypermethylation in Human Colorectal Tumors Is Not Associated with DNA Methyltransferase Overexpression," Cancer Res., May 1999; 59(10):2302-2306.
Feinberg and Tycko, "The history of cancer epigenetics," Nat Rev Cancer., Feb. 2004; 4(2):143-53.
Fodor et al., "Light-directed, spatially addressable parallel chemical synthesis," Science, Feb. 1991; 251(4995):767-773.
Frommer et al., "A genomic sequencing protocol that yields a positive display of 5-methylcytosine residues in individual DNA strands," Proc. Natl. Acad. Sci. USA, Mar. 1992; 89(5):1827-1831.

Golub et al., "Molecular classification of cancer: class discovery and class prediction by gene expression monitoring," Science, Oct. 1999; 286(5439):531-537.
Gonzalgo et al., "Methylation-sensitive Arbitrarily Primed PCR," Cancer Res., Feb. 1997; 57:594-599.
Gonzalgo and Jones, "Rapid quantitation of methylation differences at specific sites using methylation-sensitive single nucleotide primer extension (Ms-SNuPE)," Nucleic Acids Res., Jun. 1997; 25(12):2529-2531.
Goto and Monk, "Regulation of X-chromosome inactivation in development in mice and humans," Microbiol Mol Biol Rev, Jun. 1998; 62(2):362-378.
Heid et al., "Real time quantitative PCR," Genome Res., Oct. 1996; 6(10):986-994.
Herman et al., "Inactivation of the CDKN2/p16/MTS1 gene is frequently associated with aberrant DNA methylation in all common human cancers," Cancer Res., Oct. 1995; 55(20):4525-4530.
Herman et al., "Methylation-specific PCR: a novel PCR assay for methylation status of CpG islands," Proc. Natl. Acad. Sci. USA, Sep. 1996; 93(18):9821-9826.
Herman et al., "Gene silencing in cancer in association with promoter hypermethylation," N Engl J Med., Nov. 2003; 349(21):2042-2054.
Hiura et al., "Characterization of DNA methylation errors in patients with imprinting disorders conceived by assisted reproduction technologies," Hum Reprod., Aug. 2012; 27(8):2541-2548.
Huang et al., "Methylation profiling of CpG sites in human breast cancer cells," Hum Mol Genet., Mar. 1999; 8(3):459-470.
Illumina Technical Note, "Estimating Sequencing Coverage" Illumina; Dec. 1, 2014; Pub. No. 770-2011-022, 2 pages.
Jensen et al., "Whole genome bisulfite sequencing of cell-free DNA and its cellular contributors uncovers placenta hypomethylated domains", Genome Biology, Apr. 2015; 16(78):1-11.
Jones et al., "Cancer epigenetics comes of age," Nat Genet., Feb. 1999; 21(2):163-167.
Korlach et al., "Selective aluminum passivation for targeted immobilization of single DNA polymerase molecules in zero-mode waveguide nanostructures," Proc. Natl. Acad. Sci. USA, Jan. 2008; 105(4):1176-1181.
Kumar, "Rett and ICF syndromes: methylation moves into medicine," J Biosci., Sep. 2000; 25(3):213-214.
Lehmann-Werman et al., "Identification of tissue-specific cell death using methylation patterns of circulating DNA," Proc Natl Acad Sci USA, Mar. 2016; 113(13):E1826-34.
Levene et al., "Zero-mode waveguides for single-molecule analysis at high concentrations," Science, Jan. 2003; 299(5607):682-686.
Li et al., "Fast and accurate long-read alignment with Burrows-Wheeler transform," Bioinformatics, Mar. 2010; 26(5):589-95.
Lo at al., "Presence of donor-specific DNA in plasma of kidney and liver-transplant recipients," Lancet., May 1998; 351(9112):1329-1330.
Lundquist et al., "Parallel confocal detection of single molecules in real time," Opt. Lett., May 2008; 33(9):1026-1028.
Olek et al., "A modified and improved method for bisulphite based cytosine methylation analysis," Nucleic Acids Res., Dec. 1996; 24(24):5064-5066.
Otterson et al., "CDKN2 gene silencing in lung cancer by DNA hypermethylation and kinetics of p16INK4 protein induction by 5-aza 2'deoxycytidine," Oncogene, Sep. 1995; 11(6):1211-1216.
Park et al., "Methylation Profiles of CpG Island Loci in Major Types of Human Cancers", J Korean Med Sci, Apr. 2007; 22(2):311-317.
Razin and Cedar, "DNA methylation and embryogenesis," Exs, 1993; 64:343-357.
Razin, "CpG methylation, chromatin structure and gene silencing—a three-way connection," Embo J., Sep. 1998; 17(17):4905-4908.
Reik et al., "Epigenetic reprogramming in mammalian development," Science, Aug. 2001; 293(5532):1089-1093.
Ronaghi et al., "Real-time DNA sequencing using detection of pyrophosphate release," Analytical Biochemistry, Nov. 1996; 242(1):84-9.
Ronaghi et al., "A sequencing method based on real-time pyrophosphate," Science, Jul. 1998; 281(5375):363, 365.

(56) References Cited

OTHER PUBLICATIONS

Ronaghi, "Pyrosequencing sheds light on DNA sequencing," *Genome Res.*, Jan. 2001; 11(1):3-11.
Sasaki et al., "DNA methylation and genomic imprinting in mammals," *Exs*, 1993; 64:469-486.
Shendure et al., "Accurate multiplex polony sequencing of an evolved bacterial genome," *Science*; Sep. 2005; 309(5741):1728-1732.
Smiraglia et al., "A new tool for the rapid cloning of amplified and hypermethylated human DNA sequences from restriction landmark genome scanning gels," *Genomics*, Jun. 1999; 58(3):254-62.
Snyder et al., "Universal noninvasive detection of solid organ transplant rejection," *Proc Natl Acad Sci USA*; Apr. 2011; 108(15):6229-6234.
Sun et al., "Plasma DNA tissue mapping by genome-wide methylation sequencing for noninvasive prenatal, cancer, and transplantation assessments," *Proc. Natl. Acad. Sci. USA*, Oct. 2015; 112(40):E5503-E5512.
Thompson et al., "Comparison of Whole-Genome DNA Methylation Patterns in Whole Blood, Saliva, and Lymphoblastoid Cell Lines", *Behav Genet*, Dec. 2012; 43(2):168-176.
Toyota et al., "Identification of Differentially Methylated Sequences in Colorectal Cancer by Methylated CpG Island Amplification," *Cancer Res.*, May 1999; 59:2307-2312.
Van Veldhoven et al., "Epigenome-wide association study reveals decreased average methylation levels years before breast cancer diagnosis", *Clinical Epigenetics*, Aug. 2015; 7(67):1-12.
Varela-Rey, "Alcohol, DNA Methylation, and Cancer", *Alcohol Research: Current Reviews*, 35(1):1-9, https://pubs.niaaa.nih.gov/publications/arcr351/25-35.htm.
Warton et al., "Methylation of cell-free circulating DNA in the diagnosis of cancer", *Frontiers in Molecular Biosciences*, Apr. 2015; 2(13):1-10.
Whitlock, "Combining probability from independent tests: the weighted Z-method is superior to Fisher's approach", *J. Evol. Biol.*, Aug. 2005; 18(5):1368-1373.
Worthley et al., "DNA methylation within the normal colorectal mucosa is associated with pathway-specific predisposition to cancer," *Oncogene*, 2010; 29:1653-1662.
Yan et al., "Role of DNA methylation and histone acetylation in steroid receptor expression in breast cancer," *J Mammary Gland Biol Neoplasia.*, Apr. 2001; 6(2):183-192.
Yang et al., "Child Abuse and Epigenetic Mechanisms of Disease Risk", *Am J Prev Med*, Feb. 2013; 44(2):101-107.
Zhai et al., "Genome-wide DNA Methylation Profiling of Cell-Free Serum DNA in Esophageal Adenocarcinoma and Barrett Esophagus", *Neoplasia*, Jan. 2012; 14(1):29-33.
Zheng at al., "Nonhematopoietically Derived DNA Is Shorter than Hematopoietically Derived DNA in Plasma: A Transplantation Model," *Clin Chem.*, Feb. 2012; 58(3):549-558.
Zhong et al. "A survey of FRAXE allele sizes in three populations," *Am J Med Genet*, Aug. 1996; 64(2):415-419.
International Preliminary Report on Patentability, PCT/US2016/066901, 14 pages, dated Jun. 28, 2018.

\* cited by examiner

FIG. 6

|  | Cancer | Normal | Sensitivity | Specificity |
|---|---|---|---|---|
| BRCA | 8 | 3 | 72.7% | |
| CRC | 34 | 2 | 94.4% | |
| Lung | 10 | 9 | 52.6% | |
| Normal | 0 | 25 | | 100% |

FIG. 9

| | BRCA | CRC | LUNG |
|---|---|---|---|
| Acute Myeloid Leukemia | 1 | 0 | 0 |
| Breast invasive carcinoma | 7 | 0 | 0 |
| Colon adenocarcinoma | 0 | 28 | 0 |
| Esophageal carcinoma | 0 | 3 | 0 |
| Liver hepatocellular carcinoma | 0 | 1 | 1 |
| Lung adenocarcinoma | 0 | 0 | 6 |
| Lung squamous cell carcinoma | 0 | 0 | 1 |
| Sarcoma | 0 | 0 | 1 |
| Stomach adenocarcinoma | 0 | 2 | 1 |
| Sensitivity | 7/8 (88%) | 28/34 (82%) | 7/10 (70%) |

SEQUENCE LISTING

```
<160> NUMBER OF SEQ ID NOS: 9

<210> SEQ ID NO 1
<211> LENGTH: 22
<212> TYPE: DNA
<213> ORGANISM: artificial
<220> FEATURE:
<223> OTHER INFORMATION: Probe
<220> FEATURE:
<221> NAME/KEY: modified_base
<222> LOCATION: (12)..(12)
<223> OTHER INFORMATION: Methylated
<220> FEATURE:
<221> NAME/KEY: modified_base
<222> LOCATION: (16)..(16)
<223> OTHER INFORMATION: Methylated

<400> SEQUENCE: 1
acgatcgcct tcgaccgtcg aa                                              22

<210> SEQ ID NO 2
<211> LENGTH: 22
<212> TYPE: DNA
<213> ORGANISM: artificial
<220> FEATURE:
<223> OTHER INFORMATION: Probe
<220> FEATURE:
<221> NAME/KEY: misc_feature
<222> LOCATION: (2)..(2)
<223> OTHER INFORMATION: uracil that is expected to result from
      bisulfate conversion
<220> FEATURE:
<221> NAME/KEY: misc_feature
<222> LOCATION: (6)..(6)
<223> OTHER INFORMATION: uracil that is expected to result from
      bisulfate conversion
<220> FEATURE:
<221> NAME/KEY: misc_feature
<222> LOCATION: (8)..(9)
<223> OTHER INFORMATION: uracil that is expected to result from
      bisulfate conversion
<220> FEATURE:
<221> NAME/KEY: modified_base
<222> LOCATION: (12)..(12)
<223> OTHER INFORMATION: Methylated
<220> FEATURE:
<221> NAME/KEY: misc_feature
<222> LOCATION: (15)..(15)
<223> OTHER INFORMATION: uracil that is expected to result from
```

```
      bisulfate conversion
<220> FEATURE:
<221> NAME/KEY: modified_base
<222> LOCATION: (16)..(16)
<223> OTHER INFORMATION: Methylated
<220> FEATURE:
<221> NAME/KEY: misc_feature
<222> LOCATION: (19)..(19)
<223> OTHER INFORMATION: uracil that is expected to result from
      bisulfate conversion

<400> SEQUENCE: 2
angatngnnt tcgancgtng aa                                              22

<210> SEQ ID NO 3
<211> LENGTH: 22
<212> TYPE: DNA
<213> ORGANISM: artificial
<220> FEATURE:
<223> OTHER INFORMATION: Probe

<400> SEQUENCE: 3
atgattgttt tcgatcgttg aa                                              22

<210> SEQ ID NO 4
<211> LENGTH: 22
<212> TYPE: DNA
<213> ORGANISM: artificial
<220> FEATURE:
<223> OTHER INFORMATION: Probe
<220> FEATURE:
<221> NAME/KEY: modified_base
<222> LOCATION: (16)..(16)
<223> OTHER INFORMATION: Methylated

<400> SEQUENCE: 4
atgatagcct tcgaccgtag aa                                              22

<210> SEQ ID NO 5
<211> LENGTH: 22
<212> TYPE: DNA
<213> ORGANISM: artificial
<220> FEATURE:
<223> OTHER INFORMATION: Probe
<220> FEATURE:
<221> NAME/KEY: misc_feature
<222> LOCATION: (8)..(9)
<223> OTHER INFORMATION: uracil that is expected to result from
      bisulfate conversion
<220> FEATURE:
<221> NAME/KEY: misc_feature
<222> LOCATION: (12)..(12)
<223> OTHER INFORMATION: uracil that is expected to result from
      bisulfate conversion
<220> FEATURE:
<221> NAME/KEY: modified_base
<222> LOCATION: (16)..(16)
<223> OTHER INFORMATION: Methylated

<400> SEQUENCE: 5
atgatagnnt tngaccgtag aa                                              22

<210> SEQ ID NO 6
<211> LENGTH: 22
<212> TYPE: DNA
<213> ORGANISM: artificial
<220> FEATURE:
<223> OTHER INFORMATION: Probe

<400> SEQUENCE: 6
```

```
atgatagttt ttgaccgtag aa                                          22

<210> SEQ ID NO 7
<211> LENGTH: 22
<212> TYPE: DNA
<213> ORGANISM: artificial
<220> FEATURE:
<223> OTHER INFORMATION: Probe

<400> SEQUENCE: 7
ttcgacgatc gaaaacgatc gt                                          22

<210> SEQ ID NO 8
<211> LENGTH: 22
<212> TYPE: DNA
<213> ORGANISM: artificial
<220> FEATURE:
<223> OTHER INFORMATION: Probe

<400> SEQUENCE: 8
ttcaacaatc aaaaacaatc at                                          22

<210> SEQ ID NO 9
<211> LENGTH: 22
<212> TYPE: DNA
<213> ORGANISM: artificial
<220> FEATURE:
<223> OTHER INFORMATION: Probe

<400> SEQUENCE: 9
ttctacrgtc raaaactatc at                                          22
```

DISTINGUISHING METHYLATION LEVELS IN COMPLEX BIOLOGICAL SAMPLES

CROSS-REFERENCE TO RELATED APPLICATIONS

This application claims the benefit of U.S. Provisional Application Ser. No. 62/401,591, filed Sep. 29, 2016, and U.S. Provisional Application Ser. No. 62/268,961, filed Dec. 17, 2015, each of which is incorporated by reference herein.

SEQUENCE LISTING

This application contains a Sequence Listing electronically submitted via EFS-Web to the United States Patent and Trademark Office as an ASCII text file entitled "SequenceListing1396_ST25.txt" having a size of 3 kilobytes and created on Jan. 12, 2017. The information contained in the Sequence Listing is incorporated by reference herein.

BACKGROUND

The present disclosure relates to determination of methylation patterns in genomic DNA. Specific embodiments relate to prediction, diagnosis, prognosis and monitoring of various conditions based on genomic methylation patterns.

Changes in cellular genetic information, such as mutations in gene sequences which can affect gene expression and/or protein sequence, are associated with many diseases and conditions. However, changes can also occur to genes that affect gene expression; changes caused by mechanisms other than genetic mutations. Epigenetics is the study of changes in gene expression caused by mechanisms other than changes in the underlying DNA sequence, the methylation of DNA being one of those mechanisms. Methylation of DNA, for example, the addition of a methyl group to the 5 position of a cytosine pyrimidine ring or the positional sixth nitrogen of an adenine purine ring, is widespread and plays a critical role in the regulation of gene expression in development and differentiation of diseases such as multiple sclerosis, diabetes, schizophrenia, aging, and cancers. In adult somatic cells, DNA methylation typically occurs in regions where a cytosine nucleotide (C) is found next to a guanine nucleotide (G) where the C and G are linked by a phosphate group (p), the linear construct being referred to as a "CpG" site. Methylation in particular gene regions, for example, in gene promoter regions, can augment or inhibit the expression of these genes.

DNA methylation is widespread and plays a critical role in the regulation of gene expression in development, differentiation and disease. Methylation in particular regions of genes, for example their promoter regions, can inhibit the expression of these genes (Baylin and Herman (2000) DNA hypermethylation in tumorigenesis: epigenetics joins genetics. *Trends Genet*, 16, 168-174.; Jones and Laird (1999) Cancer epigenetics comes of age. *Nat Genet*, 21, 163-167). Gene silencing effects of methylated regions has been shown to be accomplished through the interaction of methylcytosine binding proteins with other structural compounds of the chromatin (Razin (1998) CpG methylation, chromatin structure and gene silencing—a three-way connection. *Embo J*, 17, 4905-4908.; Yan et al. (2001) Role of DNA methylation and histone acetylation in steroid receptor expression in breast cancer. *J Mammary Gland Biol Neoplasia*, 6, 183-192), which, in turn, makes the DNA inaccessible to transcription factors through histone deacetylation and chromatin structure changes (Bestor (1998) Gene silencing. Methylation meets acetylation. *Nature*, 393, 311-312). Genomic imprinting in which imprinted genes are preferentially expressed from either the maternal or paternal allele also involves DNA methylation. Deregulation of imprinting has been implicated in several developmental disorders (Kumar (2000) Rett and ICF syndromes: methylation moves into medicine. *J Biosci*, 25, 213-214.; Sasaki et al. (1993) DNA methylation and genomic imprinting in mammals. *Exs*, 64, 469-486.; Zhong et al. (1996) A survey of FRAXE allele sizes in three populations. *Am J Med Genet*, 64, 415-419). The references cited above are incorporated herein by reference.

In vertebrates, the DNA methylation pattern is established early in embryonic development and in general the distribution of 5-methylcytosine (5 mC) along the chromosome is maintained during the life span of the organism (Razin and Cedar (1993) DNA methylation and embryogenesis. *Exs*, 64, 343-357.; Reik et al. (2001) Epigenetic reprogramming in mammalian development. *Science*, 293, 1089-1093, each of which is incorporated herein by reference). Stable transcriptional silencing is important for normal development, and is associated with several epigenetic modifications. If methylation patterns are not properly established or maintained, various disorders like mental retardation, immune deficiency and sporadic or inherited cancers may follow.

Changes in DNA methylation have been recognized as one of the most common molecular alterations in human neoplasia. Hypermethylation of CpG sites located in promoter regions of tumor suppressor genes is a frequent mechanism for gene inactivation in cancers. Hypomethylation of genomic DNA are observed in tumor cells. Further, a correlation between hypomethylation and increased gene expression has been reported for many oncogenes. Monitoring global changes in methylation pattern has been applied to molecular classification of cancers, for example, gene hypermethylation has been associated with clinical risk groups in neuroblastoma and hormone receptor status correlation with response to tamoxifen in breast cancer.

In addition to playing an important role in cancer detection, a proper understanding of genetic methylation patterns has been used to detect other conditions. The initiation and the maintenance of the inactive X-chromosome in female eutherians were found to depend on methylation (Goto and Monk (1998) Regulation of X-chromosome inactivation in development in mice and humans. *Microbiol Mol Biol Rev*, 62, 362-378, which is incorporated herein by reference). Rett syndrome (RTT) is an X-linked dominant disease caused by mutation of MeCP2 gene, which is further complicated by X-chromosome inactivation (XCI) pattern. A current model predicts that MeCP2 represses transcription by binding methylated CpG residues and mediating chromatin remodeling (Dragich et al. (2000) Rett syndrome: a surprising result of mutation in MECP2. *Hum Mol Genet*, 9, 2365-2375, which is incorporated herein by reference).

Several technical challenges hinder development of methylation detection techniques into a robust and cost efficient screening tool. For example, the accuracy and affordability of currently available techniques can be compromised by impurities in samples that are to be tested. As a result, cumbersome and expensive purification techniques are often employed to purify a genomic sample from background nucleic acids. For example, tumor biopsy techniques are employed to physically separate tumor tissues from healthy tissues. Depending upon the depth of the tissue in the body of an individual, biopsy can require unpleasant and risky harvesting procedures such as needle biopsy, endoscopy, bronchoscopy, colonoscopy or surgery. The presence of circulating tumor DNA in blood provides an attractive alternative to such biopsy techniques. However, circulating tumor DNA is typically present in low quantities and in a background of a relatively large quantity of non-tumor DNA.

Thus there is a need for methods to distinguish methylation patterns in complex genomic samples from particular tissues of interest (e.g. tumor DNA), often in a background of other genomic material from other tissues (e.g. circulating DNA). The methods and apparatus set forth herein satisfy this need and provide other advantages as well.

BRIEF SUMMARY

The present disclosure provides a method for distinguishing an aberrant methylation level for DNA from a first cell type. The method can include steps of (a) providing a test data set that includes (i) methylation states for a plurality of sites from test genomic DNA from at least one test organism, and (ii) coverage at each of the sites for detection of the methylation states; (b) providing methylation states for the plurality of sites in reference genomic DNA from one or more reference individual organisms, (c) determining, for each of the sites, the methylation difference between the test genomic DNA and the reference genomic DNA, thereby providing a normalized methylation difference for each site; and (d) weighting the normalized methylation difference for each site by the coverage at each of the sites, thereby determining an aggregate coverage-weighted normalized methylation difference score.

Also provided is a method for distinguishing an aberrant methylation level for DNA from a sample containing DNA from a plurality of different cell types, including steps of (a) providing a sample containing a mixture of genomic DNA from a plurality of different cell types from at least one test organism, thereby providing test genomic DNA; (b) detecting methylation states for a plurality of sites in the test genomic DNA; (c) determining the coverage at each of the sites for the detecting of the methylation states; (d) providing methylation states for the plurality of sites in reference genomic DNA from at least one reference individual, the at least one test organism and reference individual optionally being the same species; (e) determining, for each of the sites, the methylation difference between the test genomic DNA and the reference genomic DNA, thereby providing a normalized methylation difference for each site; and (f) weighting the normalized methylation difference for each site by the coverage at each of the sites, thereby determining an aggregate coverage-weighted normalized methylation difference score.

In particular embodiments, this disclosure provides a method for detecting a condition such as cancer. The method can include steps of (a) providing a mixture of genomic DNA from blood of an individual suspected of having the condition (e.g. cancer), wherein the mixture comprises genomic DNA from a plurality of different cell types from the individual, thereby providing test genomic DNA; (b) detecting methylation states for a plurality of sites in the test genomic DNA; (c) determining the coverage at each of the sites for the detecting of the methylation states; (d) providing methylation states for the plurality of sites in reference genomic DNA from at least one reference individual, the reference individual being known to have the condition (e.g. cancer) or known to not have the condition (e.g. cancer); (e) determining, for each of the sites, the methylation difference between the test genomic DNA and the reference genomic DNA, thereby providing a normalized methylation difference for each site; (f) weighting the normalized methylation difference for each site by the coverage at each of the sites, thereby determining an aggregate coverage-weighted normalized methylation difference score; and (g) determining that the individual does or does not have the condition (e.g. cancer) based on the aggregate coverage-weighted normalized methylation difference score.

The present disclosure also provides an alternative sensitive method for distinguishing an aberrant methylation level for DNA from a first cell type. The method can include a first stage of establishing a methylation baseline, including the steps of (a) providing methylation states for a plurality of sites in baseline genomic DNA from two or more normal individual organisms; and (b) determining, for each of the sites, the mean methylation level and standard deviation of methylation levels for the baseline genomic DNA; a second stage of determining aggregate methylation scores for a plurality of training samples, including the steps of (c) providing a training set of normal genomic DNA samples from two or more normal individual organisms that includes (i) methylation states for a plurality of sites in the training set of normal genomic DNA samples, and optionally (ii) coverage at each of the sites for detection of the methylation states; (d) determining, for each of the sites, the methylation difference between each normal genomic DNA sample of the training set and the baseline genomic DNA, thereby providing a normalized methylation difference for each normal genomic DNA sample of the training set at each site; (e) converting the normalized methylation difference for each normal genomic DNA sample of the training set at each site into the probability of observing such a normalized methylation difference or greater, and optionally weighting the probability of such an event; (f) determining an aggregate methylation score for each normal genomic DNA sample of the training set to obtain training set methylation scores; and (g) calculating the mean methylation score and standard deviation of the training set methylation scores; a third stage, which can be carried out before, after, or concurrently with the second stage, of determining an aggregate methylation score for a given test sample, including the steps of (h) providing a test data set that includes (i) methylation states for the plurality of sites from test genomic DNA from at least one test organism, and optionally (ii) coverage at each of the sites for detection of the methylation states; (i) determining, for each of the sites, the methylation difference between the test genomic DNA and the baseline genomic DNA, thereby providing a normalized methylation difference for the test genomic DNA; (j) converting the normalized methylation difference for the test genomic DNA at each of the sites into the probability of observing such a normalized methylation difference or greater, and optionally weighting the probability of such an event; and (k) determining an aggregate methylation score for the test genomic DNA; and a fourth stage of (l) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA.

Also provided is an alternative sensitive method for distinguishing an aberrant methylation level for DNA from a sample containing DNA from a plurality of different cell types. The method can include a first stage of establishing a methylation baseline, including the steps of (a) providing methylation states for a plurality of sites in baseline genomic DNA from two or more normal individual organisms; and (b) determining, for each of the sites, the mean methylation level and standard deviation of methylation levels for the baseline genomic DNA; a second stage of determining aggregate methylation scores for a plurality of training samples, including the steps of (c) providing a training set of normal genomic DNA samples from two or more normal individual organisms that includes (i) methylation states for a plurality of sites in the training set of normal genomic DNA samples, and optionally (ii) coverage at each of the sites for detection of the methylation states; (d) determining, for each of the sites, the methylation difference between each normal genomic DNA sample of the training set and the baseline genomic DNA, thereby providing a normalized methylation difference for each normal genomic DNA sample of the training set at each site; (e) converting the normalized methylation difference for each normal genomic DNA sample of the training set at each site into the probability of observing such a normalized methylation difference or greater, and optionally weighting the probability; (f) determining an aggregate methylation score for each normal genomic DNA sample of the training set to obtain training set methylation scores; and (g) calculating the mean methylation score and standard deviation of the training set methylation scores; a third stage, which can be carried out before, after, or concurrently with the second stage, of determining an aggregate methylation score for a given test sample, including the steps of (h) providing a mixture of genomic DNA from a test organism suspected of having a condition associated with an aberrant DNA methylation level, wherein the mixture includes genomic DNA from a plurality of different cell types from the test organism, thereby providing test genomic DNA; (i) detecting methylation states for the plurality of sites in the test genomic DNA, and optionally determining the coverage at each of the sites for the detecting of the methylation states; (j) determining, for each of the sites, the methylation difference between the test genomic DNA and the baseline genomic DNA, thereby providing a normalized methylation difference for the test genomic DNA; (k) converting the normalized methylation difference for the test genomic DNA at each of the sites into the probability of observing such a normalized methylation difference or greater, and optionally weighting the probability of such an event; and (l) determining an aggregate methylation score for the test genomic DNA; and a fourth stage of (m) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA.

In particular embodiments, this disclosure provides a method for detecting a condition such as cancer. The method can include a first stage of establishing a methylation baseline, including the steps of (a) providing methylation states for a plurality of sites in baseline genomic DNA from at least one normal individual organism; and (b) determining, for each of the sites, the mean methylation level and standard deviation of methylation levels for the baseline genomic DNA; a second stage of determining aggregate methylation scores for a plurality of training samples, including the steps of (c) providing a training set of normal genomic DNA samples from two or more normal individual organisms that includes (i) methylation states for a plurality of sites in the training set of normal genomic DNA samples, and optionally (ii) coverage at each of the sites for detection of the methylation states; (d) determining, for each of the sites, the methylation difference between each normal genomic DNA sample of the training set and the baseline genomic DNA, thereby providing a normalized methylation difference for each normal genomic DNA sample of the training set at each site; (e) converting the normalized methylation difference for each normal genomic DNA sample of the training set at each site into the probability of observing such a normalized methylation difference or greater, and optionally weighting the probability of such an event; (f) determining a methylation score for each normal genomic DNA sample of the training set to obtain training set methylation scores; and (g) calculating the mean methylation score and standard deviation of the training set methylation scores; a third stage, which can be carried out before, after, or concurrently with the second stage, of determining an aggregate methylation score for a given test sample, including the steps of (h) providing a mixture of genomic DNA from a test organism suspected of having the condition, wherein the mixture comprises genomic DNA from a plurality of different cell types from the test organism, thereby providing test genomic DNA; (i) detecting methylation states for the plurality of sites in the test genomic DNA, and optionally determining the coverage at each of the sites for the detecting of the methylation states; (j) determining, for each of the sites, the methylation difference between the test genomic DNA and the baseline genomic DNA, thereby providing a normalized methylation difference for the test genomic DNA; (k) converting the normalized methylation difference for the test genomic DNA at each of the sites into the probability of observing such a normalized methylation difference or greater, and optionally weighting the probability of such an event; and (l) determining a methylation score for the test genomic DNA; and a fourth stage of (m) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA.

The present disclosure provides a method for using methylation levels to identify or classify a specific type of cancer in a test organism. The method can include a first stage of identifying specific cancers that can be used as a cancer type, including (a) providing a data set that includes methylation states for a plurality of sites from genomic DNA from clinical samples known to include a specific cancer; a second stage of selecting hypermethylated sites that includes (b) identifying hypermethylated sites characteristic of a cancer type, including (i) determining a mean methylation level for each site in the genomic DNA of the clinical samples known to include the specific cancer, (ii) determining which sites meet a first threshold, a second threshold, or a combination thereof, where determining the first threshold includes (1) determining the absolute value of the mean methylation level of each site; (2) ranking the mean methylation levels for each site from lowest to highest, and (3) selecting those sites having a mean methylation level at a percentile rank that is greater than or equivalent to a first preselected value, and where determining the second threshold includes (1) determining the absolute value of the mean methylation level of each site; and (2) selecting those sites having a mean methylation level that is greater than a second preselected value, and (iii) compiling a list of hypermethylated sites that are characteristic for the cancer type; and (c)

repeating (a) and (b) for each specific cancer, to result in a plurality of lists of hypermethylated sites that are characteristic for additional cancer types; a third stage that includes analyzing a test genomic DNA sample from a test organism by (d) providing a test data set that includes a methylation level for each hypermethylated site from a test genomic DNA from an individual test organism, wherein the hypermethylated sites are from one of the lists of hypermethylated sites that is characteristic for a cancer type identified in steps (b) and (c); (e) averaging the methylation level of each of the hypermethylated sites to result in a single average methylation level for the test genomic DNA for the cancer type identified in steps (b) and (c); (f) repeating step (e) for each cancer type, to result in an average methylation level for each cancer type; and (g) ranking the average methylation levels for each cancer type from lowest to highest, wherein the cancer type corresponding to the highest average methylation level is the cancer present in the individual test organism.

BRIEF DESCRIPTION OF THE DRAWINGS

FIG. 6 shows a tabulated summary of the methylation scores shown in FIG. 5.

FIG. 9 depicts cancer type classification results on plasma DNA samples from cancer patients, showing high clinical sensitivities for colorectal and breast cancers.

DETAILED DESCRIPTION

Figure 1:
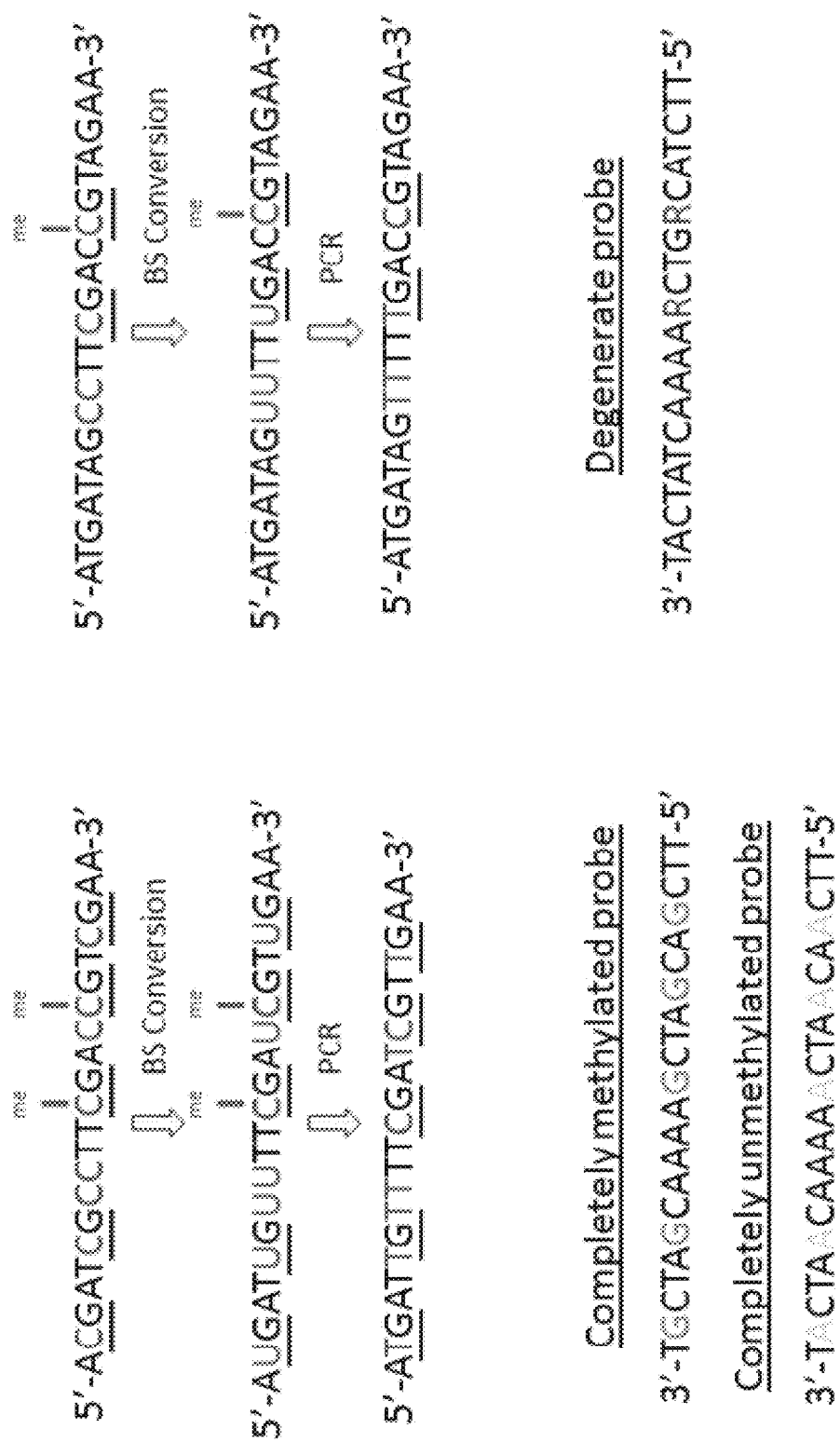
FIG. 1 shows criteria for designing probes to regions of a genome having methylation sites. ACGATCGCCTTCGACCGTCGAA (SEQ ID NO:1); AUGATUGUUTTCGAUCGTUGAA (SEQ ID NO:2); ATGATTGTTTTCGATCGTTGAA (SEQ ID NO:3); ATGATAGCCTTCGACCGTAGAA (SEQ ID NO:4); ATGATAGUUTTUGACCGTAGAA (SEQ ID NO:5); ATGATAGTTTTTGACCGTAGAA (SEQ ID NO:6); TTCGACGATCGAAAACGATCGT (SEQ ID NO:7); TTCAACAATCAAAAACAATCAT (SEQ ID NO:8); and TTCTACRGTCRAAAACTATCAT (SEQ ID NO:9).

DNA methylation data can provide valuable information, when evaluated independently or in combination with other information such as genotype or gene expression patterns. One object of the methods set forth herein is to determine this information, e.g. if one or more sites in a genome are differentially methylated in a test sample compared to a reference sample or data set.

Particular embodiments can be used for the detection, screening, monitoring (e.g. for relapse, remission, or response to treatment), staging, classification (e.g. for aid in choosing the most appropriate treatment modality) and prognostication of cancer using methylation analysis of circulating plasma/serum DNA.

Cancer DNA is known to demonstrate aberrant DNA methylation (see, for example, Herman et al. 2003 *N Engl J Med* 349: 2042-2054, which is incorporated herein by reference). For example, the CpG site promoters of genes, e.g. tumor suppressor genes, are hypermethylated while the CpG sites in the gene body are hypomethylated when compared with non-cancer cells. In particular embodiments of the methods set forth herein, a methylation pattern detected from the blood of an individual suspected of having cancer is indicative of the methylation state of potentially cancerous tissues such that the pattern is expected to be different between individuals with cancer when compared with those healthy individuals without cancer or when compared with those whose cancer has been cured.

Because aberrant methylation occurs in most cancers, the methods described herein can be applied to the detection of any of a variety of malignancies with aberrant methylation, for example, malignancies in lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinomas, adenocarcinomas, sarcomas, fibroadenocarcinoma, neuroendocrine, or undifferentiated.

In particular embodiments, a method for determining methylation patterns can be used to monitor development of a fetus (e.g. to determine the presence or absence of a developmental abnormality) or to determine the presence of a particular disease or condition. In such cases the method can be carried out using a sample (e.g. blood, tissue or amniotic fluid) obtained from a pregnant female and the sample can be evaluated for methylation levels of fetal nucleic acids. A DNA methylation profile of placental tissues can be used to evaluate the pathophysiology of pregnancy-associated or developmentally-related diseases, such as preeclampsia and intrauterine growth restriction. Disorders in genomic imprinting are associated with developmental disorders, such as Prader-Willi syndrome and Angelman syndrome, and can be identified or evaluated using methods of the present disclosure. Altered profiles of genomic imprinting and global DNA methylation in placental and fetal tissues have been observed in pregnancies resulting from assisted reproductive techniques (see, for example, Hiura et al. 2012 *Hum Reprod;* 27: 2541-2548, incorporated herein by reference) and can be detected using methods set forth herein. Exemplary methods that can be modified for use with the methods of the present disclosure are forth in US Pat. App. Pub. Nos. 2013/0189684 A1 or 2014/0080715 A1, each of which is incorporated herein by reference.

The ability to determine placental or fetal methylation patterns from maternal plasma provides a noninvasive method to determine, detect and monitor pregnancy-associated conditions such as preeclampsia, intrauterine growth restriction, preterm labor and others. For example, the detection of a disease-specific aberrant methylation signature allows the screening, diagnosis and monitoring of such pregnancy-associated conditions.

Additionally, a method set forth herein to obtain diagnostic or prognostic information for other conditions. For example, liver tissue can be analyzed to determine a methylation pattern specific to the liver, which may be used to identify liver pathologies. Other tissues which can also be analyzed include brain cells, bones, the lungs, the heart, the muscles and the kidneys, etc. DNA can be obtained from blood samples and analyzed in a method set forth herein in order to determine the state of any of a variety of tissues that contribute DNA to the blood.

Furthermore, methylation patterns of transplanted organs can be determined from plasma DNA of organ transplantation recipients. Transplant analysis from plasma, can be a synergistic technology to transplant genomic analysis from plasma, such as technology set forth in Zheng at al. 2012 *Clin Chem* 58: 549-558; Lo at al. 1998 *Lancet* 351: 1329-1330; or Snyder et al. 2011 *Proc Natl Acad Sci USA;* 108: 6229-6234, each of which is incorporated herein by reference.

The methylation patterns of various tissues may change from time to time, e.g. as a result of development, aging, disease progression (e.g. inflammation, cancer or cirrhosis) or treatment. The dynamic nature of DNA methylation makes such analysis potentially very valuable for monitoring of physiological and pathological processes. For example, if one detects a change in the plasma methylation pattern of an individual compared to a baseline value obtained when they were healthy, one could then detect disease processes in organs that contribute plasma DNA.

Terms used herein will be understood to take on their ordinary meaning in the relevant art unless specified otherwise. Several terms used herein and their meanings are set forth below.

As used herein, the term "cell-free," when used in reference to DNA, is intended to mean DNA that has been removed from a cell in vivo. The removal of the DNA can be a natural process such as necrosis or apoptosis. Cell-free DNA is generally obtained from blood, or a fraction thereof, such as plasma. Cell-free DNA can be obtained from other bodily fluids or tissues.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to urinary bladder, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, ovary epithelial, ovary fibroblast, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver Alexander, liver fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial and stomach fibroblast. In some embodiments, two cells can be considered to be the same type of cell despite one of the cells having been phenotypically or morphologically altered by a condition or disease such as cancer. For purposes of comparison, a first cell that has been altered by a disease or condition can be compared to a second cell based on the known or suspected state of the first cell prior to having been altered. For example, a cancerous pancreatic ductal epithelium cell can be considered to be the same type of cell as a non-cancerous pancreatic ductal epithelium cell.

As used herein, the term "circulating," when used in reference to DNA, is intended to mean DNA that is or was moving through the circulatory system of an organism, whether in cell-free form or inside circulating cells.

As used herein, the term "coverage," when used in reference to a genetic locus, is intended to mean the number of detection events (e.g. sequence reads) that align to, or "cover," the locus. In some embodiments, the term refers to the average number of detection events (e.g. sequence reads) that align to, or "cover," a plurality of loci. Generally, the coverage level obtained from a sequencing method correlates directly with the degree of confidence in the accuracy of the call (e.g. nucleotide type or methylation state) determined at a particular base position or genetic locus. At higher levels of coverage, a locus is covered by a greater number of aligned sequence reads, so calls can be made with a higher degree of confidence.

As used herein, the term "CpG site" is intended to mean the location in a nucleic acid molecule, or sequence representation of the molecule, where a cytosine nucleotide and guanine nucleotide occur, the 3' oxygen of the cytosine nucleotide being covalently attached to the 5' phosphate of the guanine nucleotide. The nucleic acid is typically DNA. The cytosine nucleotide can optionally contain a methyl moiety, hydroxymethyl moiety or hydrogen moiety at position 5 of the pyrimidine ring.

As used herein, the term "derived," when used in reference to DNA, is intended to refer to the source from which the DNA was obtained or the origin where the DNA was synthesized. In the case of biologically derived DNA, the term can be used to refer to an in vivo source from which the DNA was obtained or the in vivo origin where the DNA was synthesized. Exemplary origins include, but are not limited to, a cell, cell type, tissue, tissue type, organism or species of organism. In the case of synthetically derived DNA, the term can be used to refer to an in vitro source from which the DNA was obtained or the in vitro origin where the DNA was synthesized. A DNA molecule that is derived from a particular source or origin can nonetheless be subsequently copied or amplified. The sequence of the resulting copies or amplicons can be referred to as having been derived from the source or origin.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "methylation difference" is intended to mean a qualitative or quantitative indicia that two nucleotides or nucleic acids do not have the same methylation state. The methylation difference can be indicated for nucleotides that are at aligned positions on different nucleic acids. In some cases the methylation difference can be a sum or aggregate of a plurality of aligned positions.

When two or more nucleic acids are aligned, the methylation difference can be an average across one or more aligned positions.

As used herein, the term "methylation state," when used in reference to a locus (e.g., a CpG site or polynucleotide segment) across several molecules having that locus, refers to one or more characteristics of the locus relevant to presence or absence of a methyl moiety. Non-limiting examples of such characteristics include whether any of the cytosine (C) bases within a locus are methylated, location of methylated C base(s), percentage of methylated C base(s) at a particular locus, and allelic differences in methylation due to, for example, difference in the origin of alleles. Reference to the methylation state of a particular CpG site in a nucleic acid molecule, is directed to the presence or absence of a methyl moiety at position 5 of the pyrimidine ring of a cytosine. The term can be applied to one or more cytosine nucleotides (or representations thereof e.g. a chemical formula), or to one or more nucleic acid molecules (or representations thereof e.g. a sequence representation). The term can also refer to the relative or absolute amount (e.g., concentration) of methylated C or non-methylated C at a particular locus in a nucleic acid. A methylation state sometimes is hypermethylated and sometimes is hypomethylated. For example, if all or a majority of C bases within a locus are methylated, the methylation state can be referred to as "hypermethylated." In another example, if all or a majority of C bases within a locus are not methylated, the methylation state may be referred to as "hypomethylated." Likewise, if all or a majority of C bases within a locus are methylated as compared to reference then the methylation state is considered hypermethylated compared to the reference. Alternatively, if all or a majority of the C bases within a locus are not methylated as compared to a reference then the methylation state is considered hypomethylated compared to the reference.

A "methylation site" is a locus in a nucleic acid where methylation has occurred, or has the possibility of occurring. A methylation site sometimes is a C base, or multiple C bases in a region, and sometimes a methylation site is a CpG site in a locus. Each methylation site in the locus may or may not be methylated. A methylation site can be susceptible to methylation by a naturally occurring event in vivo or by an event that chemically methylates a nucleotide in vitro.

As used herein, the term "mixture," when used in reference to two or more components, is intended to mean that the two or more components are simultaneously present in a fluid or vessel. The components are typically capable of contacting each other via diffusion or agitation. The components may be separate molecules (e.g. two or more nucleic acid fragments) or the components may be part of a single molecule (e.g. sequence regions on a long nucleic acid molecule).

As used herein, the term "tissue" is intended to mean a collection or aggregation of cells that act together to perform one or more specific functions in an organism. The cells can optionally be morphologically similar. Exemplary tissues include, but are not limited to, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of a human or other body.

The embodiments set forth below and recited in the claims can be understood in view of the above definitions.

The present disclosure provides a method for distinguishing an aberrant methylation level for DNA from a first cell type. The method can include steps of (a) providing a test data set that includes (i) methylation states for a plurality of sites (e.g. CpG sites) from test genomic DNA from at least one test organism, and (ii) coverage at each of the sites (e.g. CpG sites) for detection of the methylation states; (b) providing methylation states for the plurality of sites (e.g. CpG sites) in reference genomic DNA from one or more reference individual organisms, (c) determining, for each of the sites (e.g. CpG sites), the methylation difference between the test genomic DNA and the reference genomic DNA, thereby providing a normalized methylation difference for each sites (e.g. CpG sites); and (d) weighting the normalized methylation difference for each sites (e.g. CpG sites) by the coverage at each of the sites (e.g. CpG sites), thereby determining an aggregate coverage-weighted normalized methylation difference score. Optionally the sites from the test genomic DNA are derived from a plurality of different cell types from the individual test organism and as a further option the cell type from which each of the sites is derived is unknown. In a further optional embodiment, the individual test organism and the one or more reference individual organisms are the same species.

Also provided is a method for distinguishing an aberrant methylation level for DNA from a sample containing DNA from a plurality of different cell types, including steps of (a) providing a sample containing a mixture of genomic DNA from a plurality of different cell types from at least one test organism, thereby providing test genomic DNA; (b) detecting methylation states for a plurality of sites (e.g. CpG sites) in the test genomic DNA; (c) determining the coverage at each of the sites (e.g. CpG sites) for the detecting of the methylation states; (d) providing methylation states for the plurality of sites (e.g. CpG sites) in reference genomic DNA from at least one reference individual, the at least one test organism and reference individual optionally being the same species; (e) determining, for each of the sites (e.g. CpG sites), the methylation difference between the test genomic DNA and the reference genomic DNA, thereby providing a normalized methylation difference for each site (e.g. CpG site); and (f) weighting the normalized methylation difference for each site (e.g. CpG site) by the coverage at each of the sites (e.g. CpG sites), thereby determining an aggregate coverage-weighted normalized methylation difference score.

The present invention also provides an alternative sensitive method for distinguishing an aberrant methylation level for DNA from a first cell type.

The first stage of this method involves establishing a methylation baseline, including the steps of (a) providing methylation states for a plurality of sites (e.g., CpG sites) in baseline genomic DNA from two or more normal individual organisms; and (b) determining, for each of the sites (e.g., CpG sites), the mean methylation level and standard deviation of methylation levels for the baseline genomic DNA. In some embodiments, the number of normal individual organisms providing baseline genomic DNA is at least 3, at least 5, at least 10, at least 20, at least 50, or at least 100.

The second stage of this method involves determining aggregate methylation scores for a plurality of training samples, including the steps of (c) providing a training set of normal genomic DNA samples from two or more normal individual organisms that includes (i) methylation states for a plurality of sites (e.g., CpG sites) in the training set of normal genomic DNA samples, and optionally (ii) coverage at each of the sites (e.g., CpG sites) for detection of the methylation states; (d) determining, for each of the sites (e.g., CpG sites), the methylation difference between each normal genomic DNA sample of the training set and the baseline genomic DNA, thereby providing a normalized methylation difference for each normal genomic DNA sample of the training set at each site (e.g., CpG site); (e) converting the normalized methylation difference for each normal genomic DNA sample of the training set at each site (e.g., CpG site) into the probability of observing such a normalized methylation difference or greater (e.g., a one-sided p-value), and optionally weighting the probability of such an event; (f) determining an aggregate methylation score for each normal genomic DNA sample of the training set to obtain training set methylation scores; and (g) calculating the mean methylation score and standard deviation of the training set methylation scores. In some embodiments, the number of normal individual organisms providing genomic DNA for the training set is at least 3, at least 5, at least 10, at least 20, at least 50, or at least 100.

The third stage of this method, which can be carried out before, after, or concurrently with the second stage, involves determining an aggregate methylation score for a given test sample, including the steps of (h) providing a test data set that includes (i) methylation states for the plurality of sites (e.g., CpG sites) from test genomic DNA from at least one test organism, and optionally (ii) coverage at each of the sites (e.g., CpG sites) for detection of the methylation states; (i) determining, for each of the sites (e.g., CpG sites), the methylation difference between the test genomic DNA and the baseline genomic DNA, thereby providing a normalized methylation difference for the test genomic DNA; (j) converting the normalized methylation difference for the test genomic DNA at each of the sites (e.g., CpG sites) into the probability of observing such a normalized methylation difference or greater (e.g., a one-sided p-value), and optionally weighting the probability of such an event; and (k) determining an aggregate methylation score for the test genomic DNA.

The fourth and final stage of this method involves the step of (1) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA. In the event the number of standard deviations exceeds a predetermined threshold value (e.g., 2.0, 2.5, 3.0, 3.5, 4.0, 4.5, 5.0, etc.), the test sample is considered to have an aberrant DNA methylation level.

Optionally, the methylation sites (e.g., CpG sites) from the test genomic DNA are derived from a plurality of different cell types from the individual test organism, and as a further option, the cell type from which each of the sites (e.g., CpG sites) is derived is unknown. In a further optional embodiment, the individual test organism and the one or more baseline individual organisms, training individual organisms, or a combination thereof are the same species.

Also provided is an alternative sensitive method for distinguishing an aberrant methylation level for DNA from a sample containing DNA from a plurality of different cell types.

The first stage of this method involves establishing a methylation baseline, including the steps of (a) providing methylation states for a plurality of sites (e.g., CpG sites) in baseline genomic DNA from two or more normal individual organisms; and (b) determining, for each of the sites (e.g., CpG sites), the mean methylation level and standard deviation of methylation levels for the baseline genomic DNA. In some embodiments, the number of normal individual organisms providing baseline genomic DNA is at least 3, at least 5, at least 10, at least 20, at least 50, or at least 100.

The second stage of this method involves determining aggregate methylation scores for a plurality of training samples, including the steps of (c) providing a training set of normal genomic DNA samples from two or more normal individual organisms that includes (i) methylation states for a plurality of sites (e.g., CpG sites) in the training set of normal genomic DNA samples, and optionally (ii) coverage at each of the sites (e.g., CpG sites) for detection of the methylation states; (d) determining, for each of the sites (e.g., CpG sites), the methylation difference between each normal genomic DNA sample of the training set and the baseline genomic DNA, thereby providing a normalized methylation difference for each normal genomic DNA sample of the training set at each site (e.g., CpG site); (e) converting the normalized methylation difference for each normal genomic DNA sample of the training set at each site (e.g., CpG sites) into the probability of observing such a normalized methylation difference or greater (e.g., a one-sided p-value), and optionally weighting the probability; (f) determining an aggregate methylation score for each normal genomic DNA sample of the training set to obtain training set methylation scores; and (g) calculating the mean methylation score and standard deviation of the training set methylation scores. In some embodiments, the number of normal individual organisms providing genomic DNA for the training set is at least 3, at least 5, at least 10, at least 20, at least 50, or at least 100.

The third stage of this method, which can be carried out before, after, or concurrently with the second stage, involves determining an aggregate methylation score for a given test sample, including the steps of (h) providing a mixture of genomic DNA from a test organism suspected of having a condition associated with an aberrant DNA methylation level (e.g., cancer), wherein the mixture comprises genomic DNA from a plurality of different cell types from the test organism, thereby providing test genomic DNA; (i) detecting methylation states for the plurality of sites (e.g., CpG sites) in the test genomic DNA, and optionally determining the coverage at each of the sites (e.g., CpG sites) for the detecting of the methylation states; (j) determining, for each of the sites (e.g., CpG sites), the methylation difference between the test genomic DNA and the baseline genomic DNA, thereby providing a normalized methylation difference for the test genomic DNA; (k) converting the normalized methylation difference for the test genomic DNA at each of the sites (e.g., CpG sites) into the probability of observing such a normalized methylation difference or greater (e.g., a one-sided p-value), and optionally weighting the probability of such an event; and (1) determining an aggregate methylation score for the test genomic DNA.

The fourth and final stage of this method involves the step of (m) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA. In the event the number of standard deviations exceeds a predetermined threshold value (e.g., 1.5, 2.0, 2.5, 3.0, 3.5, 4.0, 4.5, 5.0, etc.), the test sample is considered to have an aberrant DNA methylation level.

A method set forth herein can be carried out for any of a variety of test organisms. Exemplary organisms include, without limitation, eukaryotic (unicellular or multicellular) organisms. Exemplary eukaryotic organisms include a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*Oryza sativa*), wheat, rice, canola, or soybean; an algae such as *Chlamvdomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile: an amphibian such as a frog or *Xenopus laevis*; a *Dictyostelium discoideum*; a fungi such as *Pneumocystis carinii, Takifugu rubripes*, yeast such as *Saccharamoyces cerevisiae* or *Schizosaccharomyces pombe*; or a *Plasmodium falciparum*. A method of the present disclosure can also be used to evaluate methylation in organisms such as prokaryotes, examples of which include a bacterium, *Escherichia coli*, Staphylococci or *Mycoplasma pneumoniae*; an archae; a virus, examples of which include Hepatitis C virus or human immunodeficiency virus; or a viroid.

Particular embodiments of the methods set forth herein can provide advantages when applied to multicellular organisms because the methods provide for determination of the methylation states for genomic DNA derived from a particular cell or tissue in a background of nucleic acids derived from other cells or tissues. Thus, the methods set forth herein can be particularly useful for mammals, such as humans. In some cases the methods can be carried out on samples containing nucleic acid mixtures from several different cell types or tissue types such as samples obtained from the blood or other biological fluid of a multicellular organism. Furthermore, the methods set forth herein can be advantageously employed for evaluation of methylation states for genomic DNA obtained from somatic cells of a pregnant female mammal, such as a pregnant female human, and/or the methylation states for genomic DNA obtained from somatic cells of one or more prenatal offspring carried by the female.

In some embodiments, the methods can be carried out for a mixture of genomic DNA from several different cell types from a mixed organism environment (e.g. metagenomics sample) such as an ecological sample (e.g. pond, ocean, thermal vent, etc.) or digestive system sample (e.g. mouth, gut, colon, etc.). Thus, the method can be carried out for a mixed organism sample wherein individual species are not separated or cultivated.

As will be evident from several exemplary embodiments set forth herein, the CpG sites from a test genomic DNA that are evaluated in a method of this disclosure can optionally be derived from a plurality of different cell types from the individual test organism. As a further option the cell type from which each of the CpG sites is derived need not be known. This will often be the case when the sample used in the method is derived from blood or another biological fluid or metagenomics sample.

In particular embodiments, the test sample used in a method set forth herein can include circulating tumor DNA and circulating non-tumor DNA. This can be the case when the test sample includes DNA obtained from blood, for example, from an individual known or suspected to have cancer.

Particular embodiments of the methods set forth herein can be carried out using methylation states for a plurality of sites from test genomic DNA from an individual test organism. In some cases the data is provided to an individual or system that carries out the method. Alternatively, embodiments of the methods can include one or more steps for detecting methylation states for a plurality of sites in a test genome.

Methylation of sites, such as CpG dinucleotide sequences, can be measured using any of a variety of techniques used in the art for the analysis of such sites. For example, methylation can be measured by employing a restriction enzyme based technology, which utilizes methylation sensitive restriction endonucleases for the differentiation between methylated and unmethylated cytosines. Restriction enzyme based technologies include, for example, restriction digest with methylation-sensitive restriction enzymes followed by nucleic acid sequencing (e.g. massively parallel or Next Generation sequencing), Southern blot analysis, real time PCR, restriction landmark genomic scanning (RLGS) or differential methylation hybridization (DMH).

Restriction enzymes characteristically hydrolyze DNA at and/or upon recognition of specific sequences or recognition motifs that are typically between 4- to 8-bases in length. Among such enzymes, methylation sensitive restriction enzymes are distinguished by the fact that they either cleave, or fail to cleave DNA according to the cytosine methylation state present in the recognition motif, in particular, of the CpG sequences. In methods employing such methylation sensitive restriction enzymes, the digested DNA fragments can be differentially separated (e.g. based on size or hybridization affinity to complementary probes), differentially amplified (e.g. based on affinity to an amplification primer), or differentially detected (e.g. via a microarray detection technique or nucleic acid sequencing technique) such that the methylation status of the sequence can thereby be deduced.

In some embodiments that employ methylation sensitive restriction enzymes, a post-digest PCR amplification step is added wherein a set of two oligonucleotide primers, one on each side of the methylation sensitive restriction site, is used to amplify the digested genomic DNA. PCR products are produced and detected for templates that were not restricted (e.g. due to presence of a methylated restriction site) whereas PCR products are not produced where digestion of the subtended methylation sensitive restriction enzyme site occurs. Techniques for restriction enzyme based analysis of genomic methylation are well known in the art and include the following: differential methylation hybridization (DMH) (Huang et al., 1999, *Human Mol. Genet.* 8, 459-70); Not I-based differential methylation hybridization (for example, WO02/086163A1); restriction landmark genomic scanning (RLGS) (Plass et al., 1999, *Genomics* 58:254-62); methylation sensitive arbitrarily primed PCR (AP-PCR) (Gonzalgo et al., 1997, *Cancer Res.* 57: 594-599); methylated CpG site amplification (MCA) (Toyota et. al., 1999, *Cancer Res.* 59: 2307-2312). Other useful methods for detecting genomic methylation are described, for example, in US Patent Application publication 2003/0170684 A1 or WO 04/05122. The references cited above are incorporated herein by reference.

Methylation of CpG dinucleotide sequences can also be measured by employing cytosine conversion based technologies, which rely on methylation status-dependent chemical modification of CpG sequences within isolated genomic DNA, or fragments thereof, followed by DNA sequence analysis. Chemical reagents that are able to distinguish between methylated and non-methylated CpG dinucleotide sequences include hydrazine, which cleaves the nucleic acid, and bisulfite. Bisulfite treatment followed by alkaline hydrolysis specifically converts non-methylated cytosine to uracil, leaving 5-methylcytosine unmodified as described by Olek A., 1996, *Nucleic Acids Res.* 24:5064-6 or Frommer et al., 1992, *Proc. Natl. Acad. Sci. USA* 89:1827-1831, each of which is incorporated herein by reference. The bisulfite-treated DNA can subsequently be analyzed by molecular techniques, such as PCR amplification, sequencing, and detection comprising oligonucleotide hybridization (e.g. using nucleic acid microarrays).

Techniques for the analysis of bisulfite treated DNA can employ methylation-sensitive primers for the analysis of CpG methylation status with isolated genomic DNA, for example, as described by Herman et al., 1996, *Proc. Natl. Acad. Sci. USA* 93:9821-9826, or U.S. Pat. No. 5,786,146 or 6,265,171, each of which is incorporated herein by reference. Methylation sensitive PCR (MSP) allows for the detection of a specific methylated CpG position within, for example, the regulatory region of a gene. The DNA of interest is treated such that methylated and non-methylated cytosines are differentially modified, for example, by bisulfite treatment, in a manner discernable by their hybridization behavior. PCR primers specific to each of the methylated and non-methylated states of the DNA are used in PCR amplification. Products of the amplification reaction are then detected, allowing for the deduction of the methylation status of the CpG position within the genomic DNA. Other methods for the analysis of bisulfite treated DNA include methylation-sensitive single nucleotide primer extension (Ms-SNuPE) (see, for example, Gonzalgo & Jones, 1997; *Nucleic Acids Res.* 25:2529-2531, or U.S. Pat. No. 6,251,594, each of which is incorporated herein by reference), or the use of real time PCR based methods, such as the art-recognized fluorescence-based real-time PCR technique MethyLight™ (see, for example, Eads et al., 1999; *Cancer Res.* 59:2302-2306, U.S. Pat. No. 6,331,393 or Heid et al., 1996, *Genome Res.* 6:986-994, each of which is incorporated herein by reference). It will be understood that a variety of methylation assay methods can be used for the determination of the methylation status of particular genomic CpG positions. Methods which employ bisulfite conversion include, for example, bisulfite sequencing, methylation-specific PCR, methylation-sensitive single nucleotide primer extension (Ms-SnuPE), MALDI mass spectrometry and methylation-specific oligonucleotide arrays, for example, as described in U.S. Pat. No. 7,611,869 or International Patent Application WO2004/051224, each of which is incorporated herein by reference.

In particular embodiments, methylation of genomic CpG positions in a sample can be detected using an array of probes. In such embodiments, a plurality of different probe molecules can be attached to a substrate or otherwise spatially distinguished in an array. Exemplary arrays that can be used in the invention include, without limitation, slide arrays, silicon wafer arrays, liquid arrays, bead-based arrays and others known in the art or set forth in further detail herein. In preferred embodiments, the methods of the invention can be practiced with array technology that combines a miniaturized array platform, a high level of assay multiplexing, and scalable automation for sample handling and data processing. Particularly useful arrays are described in U.S. Pat. Nos. 6,355,431; 6,429,027; 6,890,741; 6,913,884 or 7,582,420; or U.S. Pat. App. Pub. Nos. 2002/0102578 A1; 2005/0053980 A1; 2005/0181440 A1; or 2009/0186349 A1, each of which is incorporated herein by reference. Further examples of useful arrays include those described in U.S. Pat. Nos. 6,023,540, 6,200,737 or 6,327,410; or PCT Pub. Nos. WO9840726, WO9918434 or WO9850782, each of which is incorporated herein by reference.

The plexity of an array used in the invention can vary depending on the probe composition and desired use of the array. For example, the plexity of nucleic acids (or CpG sites) detected in an array can be at least 10, 100, 1,000, 10,000, 0.1 million, 1 million, 10 million, 100 million or more. Alternatively or additionally, the plexity can be selected to be no more than 100 million, 10 million, 1 million, 0.1 million, 10,000, 1,000, 100 or less. Of course, the plexity can be between one of the lower values and one of the upper values selected from the ranges above. Similar plexity ranges can be achieved using nucleic acid sequencing approaches such as those known in the art as Next Generation or massively parallel sequencing.

A variety of commercially available array-based products for detection of methylation can be used including, for example, the MethylationEPIC™ BeadChip™ (Illumina, Inc., San Diego, Calif.) which allows interrogation of over 850,000 methylation sites quantitatively across the human genome at single-nucleotide resolution. Also useful are methylation microarrays available from Agilent (Santa Clara, Calif.) and other commercial suppliers of nucleic acid arrays. The array products can be customized for detection of a wide variety of methylation sites in the human genome or other genomes.

Detection of one or more nucleic acids obtained or generated in a technique set forth herein can employ a sequencing procedure, such as a sequencing-by-synthesis (SBS) technique or other techniques known in the art as massively parallel sequencing or Next Generation sequencing. Briefly, SBS can be initiated by contacting the target nucleic acids with one or more labeled nucleotides, DNA polymerase, etc. The target nucleic acid can be derived from a methylation detection technique such as bisulfate conversion or restriction with a methyl sensitive restriction endonuclease. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a method of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211, 414; 7,315,019 or 7,405,281, or US Pat. App. Pub. No. 2008/0108082 A1, each of which is incorporated herein by reference.

Other sequencing procedures that detect large numbers of nucleic acids in parallel can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); or U.S. Pat. Nos. 6,210,891; 6,258,568 or 6,274,320, each of which is incorporated herein by reference). Sequencing-by-ligation reactions are also useful including, for example, those described in Shendure et al. *Science* 309: 1728-1732 (2005); or U.S. Pat. No. 5,599,675 or 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); or WO 1989/10977, each of which is incorporated herein by reference. Techniques that use fluorescence resonance energy transfer (FRET) and/or zeromode waveguides can be used such as those described in Levene et al. *Science* 299, 682-686 (2003); Lundquist et al. *Opt. Lett.* 33, 1026-1028 (2008); or Korlach et al. *Proc. Natl. Acad. Sci. USA* 105, 1176-1181 (2008), the disclosures of which are incorporated herein by reference. Also useful are sequencing techniques that employ detection of a proton released upon incorporation of a nucleotide into an extension product, such as those commercially available from Ion Torrent (Guilford, Conn., a Life Technologies subsidiary) or described in US Pat. App. Pub. Nos. 2009/0026082 A1; 2009/0127589 A1; 2010/0137143 A1; or 2010/0282617 A1, each of which is incorporated herein by reference.

Particularly useful sequencing platforms that can be employed include those commercially available from Illumina, Inc. (San Diego, Calif.) such as the MiSeq™, NextSeq™ or HiSeq™ lines of nucleic acid sequencers; the 454 sequencing systems commercially available from Roche Life Sciences (Basel, Switzerland); the Ion Torrent sequencing systems available from Life Technologies, a subsidiary of Thermo Fisher Scientific (Waltham, Mass.); or the nanopore sequencing systems commercially available from Oxford Nanopore (Oxford, England). The TruSeq™ DNA Methylation Kit is available from Illumina, Inc. and can be used to produce bisulfite sequencing libraries that can be detected on Illumina sequencers. Useful commercial products for preparing nucleic acid samples for detection of methylation on sequencing platforms from Illumina or other suppliers include, for example, Methylation Analysis Sample Prep Products available from Thermo Fisher Scientific (Waltham, Mass.), Accel-NGS® Methyl-Seq DNA Library Kit (Swift Biosciences, Ann Arbor, Mich.), EpiMark® Methylated DNA Enrichment Kit available from New England BioLabs (Beverley, Mass.), the Pico Methyl-Seq™ Library Prep Kit available from Zymoresearch (Irvine, Calif.), or the Methylamp™ Universal Methylated DNA Preparation Kit available from EpiGentek (Farmingdale, N.Y.).

Particular embodiments can include a step of manipulating a nucleic acid sample to enrich for desired nucleic acids. For example, a sample that is provided for use in a method set forth herein can be subjected to targeted selection of a subset of genomic DNA fragments that include a set of predetermined target CpG sites. Targeted selection can occur prior to or after treating nucleic acids with bisulfite, methyl sensitive endonucleases or other reagents used to distinguish methylated sites from unmethylated sites. A useful targeted selection technique is set forth in Example I, below.

Particular embodiments of the methods set forth herein will evaluate and/or use the coverage determined for each of the sites where methylation states have been or will be determined. In some cases the coverage data is provided to an individual or system that carries out the method. Alternatively, embodiments of the methods can include one or more steps for determining coverage at each of the sites.

For embodiments that detect methylation states via a sequencing technique, coverage can be considered to describe the average number of sequencing reads that align to, or "cover," particular sites (e.g. CpG sites). The Next Generation sequencing coverage level often determines whether a particular sequence or site can be characterized with a certain degree of confidence. At higher levels of coverage, each site is covered by a greater number of aligned sequence reads, so characterizations can be made with a higher degree of confidence. A useful guide for determining coverage is provided by Illumina Technical Note "Estimating Sequencing Coverage" Pub. No. 770-2011-022 (Dec. 1, 2014), which is incorporated herein by reference. Similar coverage criteria can be applied to other detection techniques besides Next Generation sequencing techniques.

Particular embodiments of the present invention can use coverage that is at least 10×, 30×, 50×, 100×, 1,000×, 5,000×, 10,000× or more at each site. Alternatively or additionally, coverage can be at most 10,000×, 5,000×, 1,000×, 100×, 50×, 30×, 10× or less. Coverage can be selected based on a desired confidence in determining methylation pattern taken in view of the number of sites being evaluated and the quantity of DNA used in the method.

As the number of sites evaluated increases, the confidence in the characterization of the sites will also increase. This means a lower coverage can be acceptable. In particular embodiments the number of sites evaluated can be at least 10 sites, 100 sites, 500 sites, $1 \times 10^3$ sites, $5 \times 10^3$ sites, $1 \times 10^4$ sites, $1 \times 10^5$ sites, $1 \times 10^6$ sites or more. Alternatively or additionally, the number of sites evaluated can be at most $1 \times 10^6$ sites, $1 \times 10^5$ sites, $1 \times 10^4$ sites, $1 \times 10^3$ sites, 100 sites or 10 sites.

The quantity of DNA used in a method set forth herein will depend upon several factors such as the sample used and the analytical steps carried out on the sample. A typical blood draw will provide 30 ng of circulating DNA. However, larger or smaller quantities of DNA can be provided by altering the volume of blood drawn, by using a different type of sample (such as those exemplified elsewhere herein) and/or utilizing sample extraction techniques with higher or lower yields. Accordingly, a method of the present invention can be carried out using a quantity of DNA that is at least 3 ng, 10 ng, 30 ng, 50 ng, 100 ng, 500 ng or more. Alternatively or additionally, the quantity of DNA can be at most 500 ng, 100 ng, 50 ng, 30 ng, 10 ng or 3 ng.

Furthermore, in some embodiments the DNA used in a method for evaluating methylation states is a mixture of DNA from a target cell or tissue (e.g. tumor DNA) in a background of DNA from other cells or tissues (e.g. non-tumor DNA). The percent DNA from the target tissue or cell can be at most 90%, 50%, 25%, 10%, 1%, 0.1%, 0.01% or lower. Alternatively or additionally, the percent DNA from the target tissue or cell can be at least 0.01%, 0.1%, 1%, 10%, 25%, 50%, 90% or higher.

The above parameters of DNA amount, coverage, number of sites and percent DNA from the target cell or tissue can be adjusted, for example, within the ranges exemplified above to accommodate a desired confidence level in characterizing methylation states for nucleic acids in a method set forth herein.

Particular embodiments of the methods set forth herein include a step of providing methylation states for the plurality of sites in reference genomic DNA from one or more reference individual organisms. Optionally, a method can include one or more steps for detecting the methylation states for the plurality of sites in reference genomic DNA from one or more reference individual organisms. In one aspect, a reference genomic DNA can include, for instance, baseline samples. Any one of the methods set forth herein for determining methylation states of test DNA can be used to determine methylation states for reference DNA.

Reference genomic DNA, such as baseline samples, that is used in a method of the present disclosure can be from one or more organism that is (or are) the same species as the test organism. For example, when the test organism is an individual human, the reference genomic DNA can be from a different human individual. In some embodiments, the reference genomic DNA is from the same individual who provided the test genomic DNA material. For example, the test DNA can be from a tissue suspected of having a particular condition, whereas the reference DNA is from a tissue that is known not to have the condition. In particular embodiments, the test DNA can be from a tumor sample obtained from an individual whereas the reference DNA is from a normal tissue obtained from the same individual. The tissue or cell types can be the same, but for the fact that one of the tissue or cell types has a condition that the other tissue or cell type does not. Alternatively, different tissue or cell types can be obtained from the individual, one of the tissue or cell types providing test DNA and the other tissue or cell type providing reference DNA. A reference genomic DNA can be obtained from a metagenomics sample (e.g. environmental or community sample), for example, to be used in comparison to a test metagenomics sample.

A test DNA can be derived from one or more test organisms at a different time from when a reference DNA, such as baseline samples, is derived from the one or more test organisms. For example, a reference DNA sample can be obtained from an individual at a time prior to when a disease or condition is suspected to be present, and then a test DNA sample can be obtained from the individual at a later time when the individual is suspected of having a disease or condition. In such embodiments the test DNA and reference DNA can be obtained from similar tissues, communities or cell types or from different tissues, communities or cell types.

In one embodiment, a method of the present disclosure can include a step of determining, for a plurality of sites (e.g. CpG sites), the methylation difference between test genomic DNA and reference genomic DNA, thereby providing a normalized methylation difference for each site (e.g. CpG site). In particular embodiments the normalized methylation difference, also referred to as z-score, at a particular site (e.g., CpG site) is determined according to the formula $$Z_i = \frac{\chi_i - \mu_i}{\sigma_i}$$

wherein $Z_i$ represents a normalized methylation difference for a particular site identified as i, $\chi_i$ represents the methylation level at site i in the test genomic DNA, $\mu_i$ represents the mean methylation level at site i in the reference genome, and $\sigma_i$ represents the standard deviation of methylation levels at site i in the reference genomic DNA. Use of the formula for determining methylation difference is exemplified in Example I, below.

A method of the present disclosure can further include a step of weighting the normalized methylation difference for each site (e.g., CpG site) by the coverage at each of the sites (e.g., CpG sites), thereby determining an aggregate coverage-weighted normalized methylation difference score. In particular embodiments, an aggregate coverage-weighted normalized methylation difference score (represented as A) is determined according to the formula $$A = \frac{\sum_{i=1}^{k} w_i Z_i}{\sqrt{\sum_{i=1}^{k} w_i^2}}$$

wherein $w_i$ represents the coverage at site i, and k represents the total number of sites. Use of the formula for determining an aggregate coverage-weighted normalized methylation difference score is exemplified in Example I, below.

In particular embodiments, the methods set forth herein can be used to identify a change in methylation state for a test organism or to monitor such changes over time. Accordingly, the present disclosure provides a method that includes steps of (a) providing a test data set that includes (i) methylation states for a plurality of sites from test genomic DNA from at least one test organism, and (ii) coverage at each of the sites for detection of the methylation states; (b) providing methylation states for the plurality of sites in reference genomic DNA from one or more reference individual organisms, (c) determining, for each of the sites, the methylation difference between the test genomic DNA and the reference genomic DNA, thereby providing a normalized methylation difference for each site; (d) weighting the normalized methylation difference for each site by the coverage at each of the sites, thereby determining an aggregate coverage-weighted normalized methylation difference score and (e) repeating steps (a) through (d) using a second test data set that includes (i) methylation states for the plurality of sites from a second test genomic DNA from the individual test organism, and (ii) coverage at each of the sites for detection of the methylation states, and using the same reference genomic DNA from the at least one reference individual, and (f) determining whether or not a change has occurred in the aggregate coverage-weighted normalized methylation difference score between the test genomic DNA and the second test genomic DNA.

Also provided is a method that includes the steps of (a) providing a sample containing a mixture of genomic DNA from a plurality of different cell types from at least one test organism, thereby providing test genomic DNA; (b) detecting methylation states for a plurality of sites in the test genomic DNA; (c) determining the coverage at each of the sites for the detecting of the methylation states; (d) providing methylation states for the plurality of sites in reference genomic DNA from at least one reference individual, the at least one test organism and reference individual optionally being the same species; (e) determining, for each of the sites, the methylation difference between the test genomic DNA and the reference genomic DNA, thereby providing a normalized methylation difference for each site; (f) weighting the normalized methylation difference for each site by the coverage at each of the sites, thereby determining an aggregate coverage-weighted normalized methylation difference score; (g) repeating steps (a) through (f) using a second test genomic DNA provided from a sample comprising a mixture of genomic DNA from a plurality of different cell types from the at least one test organism, and using the same reference genomic DNA from the at least one reference individual, and (h) determining whether or not a change has occurred in the aggregate coverage-weighted normalized methylation difference score between the test genomic DNA and the second test genomic DNA.

In another embodiment, the method is refined to take into consideration the observed variations in aggregate DNA methylation within a normal population. The test genomic DNA is not compared directly to a reference genomic DNA;

rather, an intermediate step is interposed that includes the evaluation of a training set of normal genomic DNA samples against the reference genomic DNA—referred to in this embodiment as baseline samples—to assess variation of aggregate DNA methylation within a normal population. This involves calculating "methylation scores" for each member of a training set of normal genomic DNA samples, and determining the mean and standard deviation of the methylation scores of the training set population, thereby yielding information about the distribution of methylation scores in a normal population. In some embodiments, the number of normal individual organisms providing genomic DNA for the training set is at least 3, at least 5, at least 10, at least 20, at least 50, or at least 100.

In this embodiment, the method can include a first step of determining, for each CpG site i, the mean methylation level ($\mu_i$) and standard deviation of methylation levels ($\sigma_i$), observed for a population of reference genomic DNA. Here, the reference or baseline genomic DNA takes the form of a population of normal genomic DNA samples. A selected genomic DNA can then be compared to the baseline DNA population to evaluate variation in methylation levels. More specifically, methylation levels at each site i (e.g., CpG site) in a selected genomic DNA can be compared to the population mean, $\mu_i$, for the baseline samples to generate a methylation score for the selected genomic DNA. In one embodiment, the selected genomic DNA is a set of training controls, and in another embodiment, the selected genomic DNA is a test genomic DNA. Methylation levels can be determined by methods that are routine and known to the skilled person. For example, methylation levels can be calculated as the fraction of 'C' bases at a target CpG site out of 'C'+'U' bases following the bisulfite treatment, or the fraction of 'C' bases at a target CpG site out of total 'C'+'T' bases following the bisulfite treatment and subsequent nucleic acid amplification, as described herein.

A methylation score (MS) for a selected genomic DNA can be calculated by determining the normalized methylation difference (z-score) at a particular site i (e.g., CpG site) with reference to a set of baseline samples, converting the z-score for each site into a probability of observing such a z-score or greater (e.g., a one-sided p-value), and combining the p-values into a final, aggregate methylation score. Optionally, the p-values are weighted. Each of these steps is detailed herein and immediately below.

Methylation scores are initially determined for a training set of normal genomic DNA samples. First, a normalized methylation difference (z-score) at a particular site i (e.g., CpG site) is determined according to the formula $$Z_i = \frac{\chi_i - \mu_i}{\sigma_i}$$

wherein $Z_i$ represents a normalized methylation difference for a particular site identified as i, $\chi_i$ represents the methylation level at site i in a member of the training set of normal genomic DNA, $\mu_i$ represents the mean methylation level at site i in the baseline samples, and $\sigma_i$ represents the standard deviation of methylation levels at site i in the baseline samples.

The z-score for each CpG site i ($Z_i$) is then converted into the probability of observing such a z-score or greater. In one aspect, the probability is calculated by converting the z-score into a one-sided p-value ($p_i$). Probabilities can be calculated assuming a normal distribution, t-distribution, or binomial distribution. Statistical tools for such calculations are well known and easily available to a person of ordinary skill.

Next, a methylation score (MS), an aggregate of the probability of the observed normalized methylation differences, is determined by combining the p-values according to the Fisher formula:

$$MS = -2\sum_{i=1}^{k} \ln(p_i)$$

wherein $p_i$ represents the one-sided p-value at site i, and k represents the total number of sites. A methylation score is calculated for each member of the training set of normal genomic DNA.

Optionally, the p-value at each CpG site can be weighted by multiplying the p-value at each CpG site i ($p_i$) with a weighting factor $w_i$, where $w_i$ can correspond to the significance of the CpG site obtained from a priori knowledge, the depth of coverage associated with the site, or any other ranking method. In this aspect, a methylation score (represented as MS) is determined by combining the weighted p-values according to the Fisher formula:

$$MS = -2\sum_{i=1}^{k} \ln(w_i p_i)$$

wherein $p_i$ represents the one-sided p-value at site i, k represents the total number of sites, and $w_i$ represents the significance, for instance coverage, of the site i. Use of this formula for determining weighted methylation scores for a training set of normal genomic DNA samples is illustrated in Example III.

Statistical analysis of the training set methylation scores is then performed. The mean methylation score ($\mu_{MS}$) and standard deviation of methylation scores ($\sigma_{MS}$) in the training set of normal genomic DNA are calculated. This characterizes the distribution of the methylation score in a normal population, and can be used to determine whether the genomic DNA of a test genomic sample has an aberrant methylation level.

The methylation score (MS) of a test genomic DNA is then determined with reference to the baseline samples (as described above for members of the training set) and compared to the distribution of the methylation scores determined for the training set of normal genomic DNA.

As described above in connection with the training set, a normalized methylation difference (z-score) at a particular site i (e.g., CpG site) is first determined according to the formula $$Z_i = \frac{\chi_i - \mu_i}{\sigma_i}$$

wherein $Z_i$ represents a normalized methylation difference for a particular site identified as i, $\chi_i$ represents the methylation level at site i in the test genomic DNA, $\mu_i$ represents the mean methylation level at site i in the baseline samples, and $\sigma_i$ represents the standard deviation of methylation levels at site i in the baseline samples.

The z-score for each CpG site i ($Z_i$) is then converted into the probability of observing such a z-score or greater. In one aspect, the probability is calculated by converting the z-score into a one-sided p-value ($p_i$). Probabilities can be calculated assuming a normal distribution, t-distribution, or binomial distribution. A methylation score (MS) of the test genomic DNA is determined by combining the p-values according to the Fisher formula:

$$MS = -2 \sum_{i=1}^{k} \ln(p_i)$$

wherein $p_i$ represents the one-sided p-value at site i, and k represents the total number of sites.

Optionally, the p-value at each CpG site can be weighted by multiplying the p-value at each CpG site i ($p_i$) with a weight $w_i$, where $w_i$ can correspond to the significance of the CpG site obtained from a priori knowledge, the depth of coverage associated with the site, or any other ranking method. A methylation score (MS) of the test genomic DNA is determined by combining the weighted p-values according to the Fisher formula:

$$MS = -2 \sum_{i=1}^{k} \ln(w_i p_i)$$

wherein $p_i$ represents the one-sided p-value at site i, k represents the total number of sites, and $w_i$ represents the significance, for instance coverage, of the site i. Use of this formula for determining weighted methylation scores for test genomic DNA samples is illustrated in Examples II and III.

Finally, the methylation score of the test genomic DNA is evaluated against the distribution of methylation scores determined for the training set population, represented by the mean methylation score ($\mu_{MS}$) and standard deviation of methylation scores ($\sigma_{MS}$) for the training set of normal genomic DNA. The number of standard deviations the methylation score for the test genomic DNA is from the methylation score mean ($\mu_{MS}$) of the training set of normal genomic DNA is determined according to the formula $$Z_{MS} = \frac{MS - \mu_{MS}}{\sigma_{MS}}$$

wherein $Z_{MS}$ represents a normalized methylation score difference, MS represents the methylation score of the test sample, $\mu_{MS}$ represents the mean methylation score for the training set of normal genomic DNA, and $\sigma_{MS}$ represents the standard deviation of methylation scores for the training set of normal genomic DNA. Use of this formula for determining normalized methylation score difference is illustrated in Example III. A $Z_{MS}$ value of greater than 1.5, greater than 2, greater than 2.5, or greater than 3 standard deviations indicates the test genomic DNA has an aberrant DNA methylation level. In a preferred embodiment, a $Z_{MS}$ value greater than 3 standard deviations is used as an indication that the test genomic DNA has an aberrant DNA methylation level.

In another embodiment, the methods set forth herein can be used to identify a change in methylation state for a test organism or to monitor such changes over time. Accordingly, the present disclosure provides a method that includes steps of (a) providing methylation states for a plurality of sites (e.g., CpG sites) in baseline genomic DNA from two or more normal individual organisms; (b) determining, for each of the sites (e.g., CpG sites), the mean methylation level and standard deviation of methylation levels for the baseline genomic DNA; (c) providing a test data set that includes (i) methylation states for the plurality of sites (e.g., CpG sites) from a first test genomic DNA from at least one test organism, and optionally (ii) coverage at each of the sites (e.g., CpG sites) for detection of the methylation states; (d) determining, for each of the sites (e.g., CpG sites), the methylation difference between the first test genomic DNA and the baseline genomic DNA, thereby providing a normalized methylation difference for the first test genomic DNA; (e) converting the normalized methylation difference for the first test genomic DNA at each of the sites (e.g., CpG sites) into the probability of observing such a normalized methylation difference or greater (e.g., a one-sided p-value), and optionally weighting the probability of such an event; (f) determining a methylation score for the first test genomic DNA; (g) repeating steps (c) through (f) using a second test genomic DNA provided from a sample comprising a mixture of genomic DNA from a plurality of different cell types from the at least one test organism, and using the same baseline genomic DNA; and (h) determining whether or not a change has occurred in the methylation score between the first test genomic DNA and the second test genomic DNA.

An alternative method of monitoring changes in DNA methylation over time includes the steps of (a) providing methylation states for a plurality of sites (e.g., CpG sites) in baseline genomic DNA from two or more normal individual organisms; (b) determining, for each of the sites (e.g., CpG sites), the mean methylation level and standard deviation of methylation levels for the baseline genomic DNA; (c) providing a mixture of genomic DNA from a test organism suspected of having a condition associated with an aberrant DNA methylation level (e.g., cancer), wherein the mixture comprises genomic DNA from a plurality of different cell types from the test organism, thereby providing a first test genomic DNA; (d) detecting methylation states for the plurality of sites (e.g., CpG sites) in the first test genomic DNA, and optionally determining the coverage at each of the sites (e.g., CpG sites) for the detecting of the methylation states; (e) determining, for each of the sites (e.g., CpG sites), the methylation difference between the first test genomic DNA and the baseline genomic DNA, thereby providing a normalized methylation difference for the first test genomic DNA; (f) converting the normalized methylation difference for the first test genomic DNA at each of the sites (e.g., CpG sites) into the probability of observing such a normalized methylation difference or greater (e.g., a one-sided p-value), and optionally weighting the probability of such an event; (g) determining a methylation score for the first test genomic DNA; (h) repeating steps (c) through (g) using a second test genomic DNA provided from a sample comprising a mixture of genomic DNA from a plurality of different cell types from the at least one test organism, and using the same baseline genomic DNA; and (i) determining whether or not a change has occurred in the methylation score between the first test genomic DNA and the second test genomic DNA.

First and second test genomic DNA samples (or test data sets) that are compared in a method set forth herein can be derived from the same type of cell, community, tissue or fluid, but at different time points. Accordingly, a method set forth herein can be used to identify or monitor a change that occurs over time. In some embodiments the different time points can occur before, during and/or after a particular treatment. For example, in the case of monitoring or prognosing cancer, samples can be obtained from an individual before and after initiation of a treatment such as surgery, chemotherapy or radiation therapy. Furthermore multiple samples can be obtained at different time points during treatment. For example the samples can be obtained and evaluated at time points throughout surgery (e.g. to evaluate whether or not margins have been cleared of cancerous tissue) or at different time points throughout a course of chemotherapy or radiation therapy. Different samples can be obtained from an individual and tested after treatment for example to test for relapse and remission.

In a further example, gut metagenomics samples can be obtained before and after a treatment (e.g. for a digestive disorder). The methylation states of the samples can be evaluated and compared to identify changes in the bacterial flora of the gut due to the treatment. The changes in turn can be used to monitor the treatment and determine a prognosis for the individual being treated.

Any of a variety of sample types set forth herein, or known in the art to contain tumor DNA, can be used in a method for identifying or monitoring a change in methylation state for an individual. Observed changes can provide a basis for diagnosis, prognosis, or screening of an individual with respect to having a particular condition such as cancer.

A method set forth herein can also be used to screen or test a candidate treatment, for example, in an experimental cell culture, tissue or organism. Accordingly, a method set forth herein can be used to identify or monitor a change that occurs over time in a cell culture, tissue or organism being tested in a clinical or laboratory environment. In some embodiments the different time points can occur before, during and/or after a particular candidate treatment. For example, samples can be obtained from a test organism before and after initiation of a candidate treatment such as surgery, chemotherapy or radiation therapy. Furthermore, multiple samples can be obtained at different time points during the candidate treatment. For example the samples can be obtained and evaluated at time points throughout surgery (e.g. to evaluate whether or not margins have been cleared of cancerous tissue) or at different time points throughout a course of a candidate chemotherapy or radiation therapy. Different samples can be obtained from a test organism and tested after a candidate treatment, for example, to evaluate relapse and remission. Control organisms that are not subjected to the candidate treatment and/or that do not have a particular condition can also be tested using similar methods. Comparison of results between samples subjected to candidate treatments and controls can be used to determine efficacy and/or safety of a particular candidate treatment Any of a variety of sample types set forth herein, or known in the art to contain tumor DNA, can be used in a method for identifying or screening a candidate treatment. Changes, whether or not being compared to a particular control, can be used for evaluating efficacy and/or safety of a particular candidate treatment.

In particular embodiments, this disclosure provides a method for detecting a condition such as cancer. The method can include steps of (a) providing a mixture of genomic DNA from an individual suspected of having the condition (e.g. cancer), wherein the mixture comprises genomic DNA from a plurality of different cell types from the individual, thereby providing test genomic DNA; (b) detecting methylation states for a plurality of sites (e.g. CpG sites) in the test genomic DNA; (c) determining the coverage at each of the sites (e.g. CpG sites) for the detecting of the methylation states; (d) providing methylation states for the plurality of sites (e.g. CpG sites) in reference genomic DNA from at least one reference individual, the reference individual being known to have the condition (e.g. cancer) or known to not have the condition (e.g. cancer); (e) determining, for each of the sites (e.g. CpG sites), the methylation difference between the test genomic DNA and the reference genomic DNA, thereby providing a normalized methylation difference for each site (e.g. CpG site); (f) weighting the normalized methylation difference for each site (e.g. CpG site) by the coverage at each of the sites (e.g. CpG sites), thereby determining an aggregate coverage-weighted normalized methylation difference score; and (g) determining that the individual does or does not have the condition (e.g. cancer) based on the aggregate coverage-weighted normalized methylation difference score. In some embodiments the sample is blood and the DNA can, for example, include cell free DNA from the blood.

Also provided is a method for identifying a change in a condition such as cancer. The method can include steps of (a) providing a mixture of genomic DNA from an individual suspected of having the condition (e.g. cancer), wherein the mixture comprises genomic DNA from a plurality of different cell types from the individual, thereby providing test genomic DNA; (b) detecting methylation states for a plurality of sites (e.g. CpG sites) in the test genomic DNA; (c) determining the coverage at each of the sites (e.g. CpG sites) for the detecting of the methylation states; (d) providing methylation states for the plurality of sites (e.g. CpG sites) in reference genomic DNA from at least one reference individual, the reference individual being known to have the condition (e.g. cancer) or known to not have the condition (e.g. cancer); (e) determining, for each of the sites (e.g. CpG sites), the methylation difference between the test genomic DNA and the reference genomic DNA, thereby providing a normalized methylation difference for each site (e.g. CpG site); (f) weighting the normalized methylation difference for each site (e.g. CpG site) by the coverage at each of the sites (e.g. CpG sites), thereby determining an aggregate coverage-weighted normalized methylation difference score; and (g) repeating steps (a) through (f) using a second mixture of genomic DNA from the individual suspected of having the condition (e.g. cancer), and using the same reference genomic DNA from the at least one reference individual, and (h) determining whether or not a change has occurred in the aggregate coverage-weighted normalized methylation difference score for the second test genomic DNA compared to the test genomic DNA, thereby determining that a change has or has not occurred in the condition (e.g. cancer) based on the change in the aggregate coverage-weighted normalized methylation difference score.

In particular embodiments, this disclosure provides a method for detecting a condition such as cancer. The method can include steps of (a) providing methylation states for a plurality of sites (e.g., CpG sites) in baseline genomic DNA from at least one normal individual organism; (b) determining, for each of the sites (e.g., CpG sites), the mean methylation level and standard deviation of methylation levels for the baseline genomic DNA; (c) providing a training set of normal genomic DNA samples from two or more normal individual organisms that includes (i) methylation states for a plurality of sites (e.g., CpG sites) in the training set of normal genomic DNA samples, and optionally (ii) coverage at each of the sites (e.g., CpG sites) for detection of the methylation states; (d) determining, for each of the sites (e.g., CpG sites), the methylation difference between each normal genomic DNA sample of the training set and the baseline genomic DNA, thereby providing a normalized methylation difference for each normal genomic DNA sample of the training set at each site (e.g., CpG site); (e) converting the normalized methylation difference for each normal genomic DNA sample of the training set at each site (e.g., CpG site) into the probability of observing such a normalized methylation difference or greater (e.g., a one-sided p-value), and optionally weighting the probability of such an event; (f) determining a methylation score for each normal genomic DNA sample of the training set to obtain training set methylation scores; (g) calculating the mean methylation score and standard deviation of the training set methylation scores; (h) providing a mixture of genomic DNA from a test organism suspected of having the condition (e.g., cancer), wherein the mixture comprises genomic DNA from a plurality of different cell types from the test organism, thereby providing test genomic DNA; (i) detecting methylation states for the plurality of sites (e.g., CpG sites) in the test genomic DNA, and optionally determining the coverage at each of the sites (e.g., CpG sites) for the detecting of the methylation states; (j) determining, for each of the sites (e.g., CpG sites), the methylation difference between the test genomic DNA and the baseline genomic DNA, thereby providing a normalized methylation difference for the test genomic DNA; (k) converting the normalized methylation difference for the test genomic DNA at each of the sites (e.g., CpG sites) into the probability of observing such a normalized methylation difference or greater (e.g., a one-sided p-value), and optionally weighting the probability of such an event; (l) determining a methylation score for the test genomic DNA; and (m) comparing the methylation score of the test genomic DNA to the mean methylation score and standard deviation of methylation scores in the training set of normal genomic DNA to determine the number of standard deviations the methylation score of the test genomic DNA is from the distribution of methylation scores in the training set of normal genomic DNA. In the event the number of standard deviations exceeds a predetermined threshold value (e.g., 1.5, 2.0, 2.5, 3.0, 3.5, 4.0, 4.5, 5.0, etc.), the test sample is considered to have an aberrant DNA methylation level.

Optionally, the sites from the test genomic DNA are derived from a plurality of different cell types from the individual test organism, and as a further option, the cell type from which each of the sites (e.g., CpG sites) is derived is unknown. In a further optional embodiment, the individual test organism and the one or more baseline individual organisms, training individual organisms, or a combination thereof are the same species. In some embodiments, the mixture of genomic DNA from an individual suspected of having the condition is blood and the DNA can, for example, include cell-free DNA (cfDNA) or circulating tumor DNA (ctDNA) from the blood.

Also provided herein is a method for identifying a change in a condition such as cancer over time. The method can include steps of (a) providing methylation states for a plurality of sites (e.g., CpG sites) in baseline genomic DNA from at least one normal individual organism; (b) determining, for each of the sites (e.g., CpG sites), the mean methylation level and standard deviation of methylation levels for the baseline genomic DNA; (c) providing a first mixture of genomic DNA from a test organism suspected of having the condition (e.g., cancer), wherein the first mixture comprises genomic DNA from a plurality of different cell types from the test organism, thereby providing a first test genomic DNA; (d) detecting methylation states for the plurality of sites (e.g., CpG sites) in the first test genomic DNA, and optionally determining the coverage at each of the sites (e.g., CpG sites) for the detecting of the methylation states; (e) determining, for each of the sites (e.g., CpG sites), the methylation difference between the first test genomic DNA and the baseline genomic DNA, thereby providing a normalized methylation difference for the first test genomic DNA; (f) converting the normalized methylation difference for the first test genomic DNA at each of the sites (e.g., CpG sites) into the probability of observing such a normalized methylation difference or greater (e.g., a one-sided p-value), and optionally weighting the probability of such an event; (g) determining a methylation score for the first test genomic DNA; (h) repeating steps (c) through (g) using a second mixture of genomic DNA from the test organism suspected of having the condition (e.g., cancer), wherein the second mixture comprises a second test genomic DNA, and (i) determining whether or not a change has occurred in the methylation score for the second test genomic DNA compared to the first test genomic DNA, thereby determining that a change has or has not occurred in the condition (e.g., cancer) based on the change in the methylation score.

Methylation states determined using methods set forth herein can be used for molecular classification and prediction of cancers using criteria that have been developed for gene expression and other genomic data (see, for example, Golub et al. (1999) Molecular classification of cancer: class discovery and class prediction by gene expression monitoring. *Science*, 286, 531-537). Other classification systems that can be used include those that have been developed for correlating global changes in methylation pattern to molecular classification in breast cancer (see, for example, Huang et al. (1999) Methylation profiling of CpG sites in human breast cancer cells. *Hum Mol Genet*, 8, 459-470), or those developed for correlating methylation patterns in tumor suppressor genes (for example, p16, a cyclin-dependent kinase inhibitor) in certain human cancer types (see, for example, Herman et al. (1995) Inactivation of the CDKN2/p16/MTS1 gene is frequently associated with aberrant DNA methylation in all common human cancers. *Cancer Res*, 55, 4525-4530.; Otterson et al. (1995) CDKN2 gene silencing in lung cancer by DNA hypermethylation and kinetics of p16INK4 protein induction by 5-aza 2'deoxycytidine. *Oncogene*, 11, 1211-1216). The above references are incorporated herein by reference.

In some applications of the methylation analysis methods set forth herein, a model can be developed to predict the disease type without prior pathological diagnosis. Thus, in some embodiments, the methods set forth herein are used to determine methylation patterns in staged tumor samples relative to matched normal tissues from the same patient. The determined differences in methylation pattern between the tumor and normal tissues can be used to build a model to predict, diagnose or monitor cancer. For example, methylation patterns determined for a test sample can be compared to a methylation pattern from a known normal and/or from a known tumor, and a diagnosis can be made based on the degree of similarity of the test sample to one or both of these references.

In addition, the methods set forth herein can facilitate identification, classification and prognostic evaluation of tumors. This information can in turn be used to identify subgroups of tumors with related properties. Such classification has been useful in identifying the causes of various types of cancer and in predicting their clinical behavior.

In particular embodiments of the present methods, cancers are predicted, detected, identified, classified, or monitored from cell free DNA of cancer patients. For example, the determination of a methylation pattern from a plasma sample can be used to screen for cancer. When the methylation pattern of the plasma sample is aberrant compared with a healthy reference, cancer may be suspected. Then further confirmation and assessment of the type of cancer or tissue origin of the cancer can be performed by determining the plasma profile of methylation at different genomic loci or by plasma genomic analysis to detect tumor-associated copy number aberrations, chromosomal translocations and single nucleotide variants. Alternatively, radiological and imaging investigations (e.g. computed tomography, magnetic resonance imaging, positron emission tomography) or endoscopy (e.g. upper gastrointestinal endoscopy or colonoscopy) can be used to further investigate individuals who were suspected of having cancer based on the plasma methylation level analysis.

In one aspect of the present invention, provided herein is a method for using methylation levels to identify or classify a specific type of cancer in a test organism, preferably a mammalian organism, more preferably a human. In this aspect, methylation levels of a test genomic DNA are evaluated, for subsets of preselected methylation sites associated with known cancer types, herein referred to as "hypermethylated" sites, and then ranked from lowest to highest. The cancer type corresponding to the highest average methylation level is considered to be associated with the test genomic DNA, i.e. the cancer type is deemed to be present in the test organism.

As a starting point, the method can include identifying specific cancers that can be used as a cancer type in the identification or classification algorithm according to this aspect of the invention. A cancer type is a cancer, e.g., breast invasive carcinoma, colon adenocarcinoma, lung adenocarcinoma, and others, that can be used as a member of a panel of specific cancers to determine whether a test organism has a specific type of cancer.

Determining whether a cancer can be used as a cancer type in the present method includes obtaining genomic DNA sequence data from clinical samples. Genomic DNA sequence data useful herein is readily available from known databases that characterize genomic and epigenomic changes—such as changes in methylation state—in different types of cancers. The greater the number of clinical samples of a cancer in a database, the more likely the cancer can be used as a cancer type. A cancer type suitable for the present method may be defined using genomic DNA sequence data from at least 10, at least 15, at least 20, at least 25, at least 30, at least 40, at least 50, at least 75, or at least 100 clinical samples of a specific cancer.

Once a panel of suitable cancer type has been defined, a list of so-called "hypermethylated" sites specific for each cancer type is assembled. In some embodiments, useful methylation sites that can be evaluated for methylation state include the selected CpG sites of the Pan Cancer Panel set forth in Table I (the listed methylation sites are from Genome Build 37) and/or set forth in Table II (the listed methylation sites are from Genome Build 37). In other embodiments, useful methylation sites that can be evaluated for methylation state include those present in The Cancer Genome Atlas (see, for example, Cancer Genome Atlas Research Network et al., *Nature Genetics* 45:1113-1120 (2013)), the CpG sites used to identify or monitor colorectal cancer described in Worthley et al., *Oncogene* 29, 1653-1662 (2010), and methylation markers for detection of ovarian cancer set forth in US Pat. App. Pub. No. 2008/0166728 A1, among others. All of the cited documents are incorporated herein by reference in their entireties. All or a subset of the sites set forth herein or listed in a reference herein can be used in the identification or classification method set forth herein. For example, at least 100, $1\times10^3$, $1\times10^4$, $1\times10^5$, $1\times10^6$, or more of the methylation sites can be used as a starting point. In some embodiments, the entire methylome (i.e. the full set of methylation sites in a test organism's genome) may be used to select hypermethylated sites suitable for the present method.

TABLE I

| Pan Cancer Panel |
|---|
| cg00006948 |
| cg00012992 |
| cg00019137 |
| cg00021108 |
| cg00026375 |
| cg00027037 |
| cg00039627 |
| cg00041084 |
| cg00056676 |
| cg00059034 |
| cg00073771 |
| cg00073780 |
| cg00079563 |
| cg00081574 |
| cg00091964 |
| cg00107016 |
| cg00114393 |
| cg00114963 |
| cg00115040 |
| cg00117463 |
| cg00121634 |
| cg00121640 |
| cg00124160 |
| cg00128353 |
| cg00132108 |
| cg00134776 |
| cg00136947 |
| cg00139244 |
| cg00141174 |
| cg00143220 |
| cg00145489 |
| cg00151810 |
| cg00155423 |
| cg00157987 |
| cg00158254 |
| cg00164196 |
| cg00168514 |
| cg00169305 |
| cg00183340 |
| cg00196372 |
| cg00202702 |
| cg00205263 |
| cg00207389 |
| cg00208931 |
| cg00210994 |
| cg00214530 |
| cg00220517 |
| cg00221969 |
| cg00233079 |
| cg00235260 |
| cg00235337 |
| cg00245538 |
| cg00246817 |
| cg00251610 |
| cg00254802 |
| cg00259618 |
| cg00262031 |
| cg00264591 |
| cg00266918 |
| cg00267325 |
| cg00275232 |
| cg00280758 |
| cg00281977 |

TABLE I-continued

Pan Cancer Panel

| | |
|---|---|
| cg00283576 | cg00562243 |
| cg00286984 | cg00567696 |
| cg00288050 | cg00574530 |
| cg00289081 | cg00576301 |
| cg00291351 | cg00577109 |
| cg00302521 | cg00581731 |
| cg00303548 | cg00582881 |
| cg00303672 | cg00583303 |
| cg00310855 | cg00586537 |
| cg00311654 | cg00588720 |
| cg00312474 | cg00591844 |
| cg00318608 | cg00593962 |
| cg00322319 | cg00594560 |
| cg00325599 | cg00594866 |
| cg00338893 | cg00598730 |
| cg00341980 | cg00603617 |
| cg00344260 | cg00607526 |
| cg00346326 | cg00611485 |
| cg00350003 | cg00613753 |
| cg00351011 | cg00614641 |
| cg00352349 | cg00616965 |
| cg00353340 | cg00618725 |
| cg00358220 | cg00622677 |
| cg00365470 | cg00626110 |
| cg00367047 | cg00633736 |
| cg00370303 | cg00639886 |
| cg00371920 | cg00642494 |
| cg00372486 | cg00643111 |
| cg00381697 | cg00650006 |
| cg00389976 | cg00651829 |
| cg00395632 | cg00656387 |
| cg00397851 | cg00656411 |
| cg00401880 | cg00658626 |
| cg00404838 | cg00659495 |
| cg00405843 | cg00661753 |
| cg00407729 | cg00663739 |
| cg00408906 | cg00673557 |
| cg00414171 | cg00679738 |
| cg00414398 | cg00683895 |
| cg00415978 | cg00687122 |
| cg00419564 | cg00691999 |
| cg00440043 | cg00692763 |
| cg00442814 | cg00695712 |
| cg00447632 | cg00697033 |
| cg00449821 | cg00702008 |
| cg00450312 | cg00704633 |
| cg00456894 | cg00708380 |
| cg00466108 | cg00709515 |
| cg00466364 | cg00712044 |
| cg00470794 | cg00713925 |
| cg00471966 | cg00719143 |
| cg00474209 | cg00720475 |
| cg00476317 | cg00735962 |
| cg00480136 | cg00741789 |
| cg00483446 | cg00744920 |
| cg00485296 | cg00745606 |
| cg00485849 | cg00747619 |
| cg00486611 | cg00751156 |
| cg00486627 | cg00752016 |
| cg00487870 | cg00752376 |
| cg00488787 | cg00755836 |
| cg00489861 | cg00757182 |
| cg00495503 | cg00758584 |
| cg00498155 | cg00761787 |
| cg00499289 | cg00769520 |
| cg00503704 | cg00769843 |
| cg00504703 | cg00773459 |
| cg00507727 | cg00780574 |
| cg00512374 | cg00790649 |
| cg00525503 | cg00793280 |
| cg00527440 | cg00796360 |
| cg00533620 | cg00796793 |
| cg00549463 | cg00797346 |
| cg00549910 | cg00800993 |
| cg00551736 | cg00803088 |
| cg00552973 | cg00803816 |
| cg00559018 | cg00808740 |
| cg00560547 | cg00809888 |

TABLE I-continued

Pan Cancer Panel

| | |
|---|---|
| cg00813603 | cg01083689 |
| cg00815093 | cg01093319 |
| cg00818693 | cg01097611 |
| cg00819163 | cg01097881 |
| cg00821073 | cg01097964 |
| cg00824141 | cg01098237 |
| cg00828602 | cg01099231 |
| cg00834400 | cg01099875 |
| cg00835429 | cg01101742 |
| cg00838874 | cg01105385 |
| cg00843352 | cg01107801 |
| cg00845942 | cg01108392 |
| cg00846483 | cg01112082 |
| cg00850971 | cg01112965 |
| cg00868383 | cg01126855 |
| cg00873850 | cg01141237 |
| cg00877887 | cg01142386 |
| cg00879003 | cg01143579 |
| cg00879447 | cg01143804 |
| cg00880074 | cg01145317 |
| cg00884221 | cg01151699 |
| cg00887511 | cg01152936 |
| cg00894435 | cg01153132 |
| cg00896540 | cg01156948 |
| cg00899483 | cg01157070 |
| cg00901765 | cg01160085 |
| cg00906644 | cg01175682 |
| cg00907211 | cg01179851 |
| cg00918541 | cg01181350 |
| cg00919118 | cg01183053 |
| cg00929855 | cg01184522 |
| cg00939301 | cg01186777 |
| cg00940278 | cg01187533 |
| cg00944142 | cg01191114 |
| cg00948275 | cg01196517 |
| cg00953355 | cg01204271 |
| cg00953777 | cg01211349 |
| cg00954566 | cg01215936 |
| cg00964103 | cg01216370 |
| cg00965391 | cg01224730 |
| cg00966974 | cg01226806 |
| cg00969047 | cg01227006 |
| cg00969787 | cg01228636 |
| cg00971804 | cg01236148 |
| cg00976157 | cg01244034 |
| cg00977805 | cg01244650 |
| cg00979348 | cg01245656 |
| cg00983637 | cg01246835 |
| cg00984694 | cg01247426 |
| cg00992385 | cg01250961 |
| cg00994693 | cg01254575 |
| cg00996262 | cg01256674 |
| cg00996986 | cg01258587 |
| cg00999950 | cg01259619 |
| cg01009697 | cg01263075 |
| cg01012280 | cg01263292 |
| cg01015652 | cg01263716 |
| cg01016553 | cg01267522 |
| cg01016662 | cg01268683 |
| cg01019028 | cg01269344 |
| cg01024009 | cg01269537 |
| cg01025398 | cg01270246 |
| cg01029840 | cg01274625 |
| cg01033463 | cg01275523 |
| cg01035198 | cg01277490 |
| cg01043524 | cg01280202 |
| cg01045612 | cg01284881 |
| cg01052477 | cg01289643 |
| cg01054622 | cg01294263 |
| cg01060026 | cg01300341 |
| cg01060059 | cg01307939 |
| cg01069256 | cg01308268 |
| cg01070355 | cg01310019 |
| cg01070794 | cg01310600 |
| cg01076997 | cg01313313 |
| cg01078147 | cg01313518 |
| cg01079098 | cg01315063 |
| cg01079658 | cg01316109 |

TABLE I-continued

Pan Cancer Panel

| | |
|---|---|
| cg01327552 | cg01587630 |
| cg01333350 | cg01588748 |
| cg01335685 | cg01593751 |
| cg01335781 | cg01597066 |
| cg01339444 | cg01601746 |
| cg01340952 | cg01606085 |
| cg01341170 | cg01606998 |
| cg01363902 | cg01607295 |
| cg01367393 | cg01611886 |
| cg01369082 | cg01612478 |
| cg01370014 | cg01613306 |
| cg01370063 | cg01616178 |
| cg01370181 | cg01616474 |
| cg01372071 | cg01618114 |
| cg01373292 | cg01618829 |
| cg01377006 | cg01632300 |
| cg01380710 | cg01637011 |
| cg01384163 | cg01637551 |
| cg01385795 | cg01641096 |
| cg01387945 | cg01645113 |
| cg01394093 | cg01646610 |
| cg01398050 | cg01646639 |
| cg01402994 | cg01649597 |
| cg01404988 | cg01653005 |
| cg01406536 | cg01656221 |
| cg01409659 | cg01657408 |
| cg01414358 | cg01665212 |
| cg01418667 | cg01666600 |
| cg01419567 | cg01667646 |
| cg01421405 | cg01667837 |
| cg01424281 | cg01677561 |
| cg01429635 | cg01678172 |
| cg01431908 | cg01678714 |
| cg01434487 | cg01682021 |
| cg01442844 | cg01692340 |
| cg01445942 | cg01699584 |
| cg01446203 | cg01706029 |
| cg01450204 | cg01706789 |
| cg01451328 | cg01719157 |
| cg01453694 | cg01719793 |
| cg01458686 | cg01722423 |
| cg01460805 | cg01722994 |
| cg01462053 | cg01725608 |
| cg01464969 | cg01740172 |
| cg01466678 | cg01740424 |
| cg01479818 | cg01742897 |
| cg01483681 | cg01743617 |
| cg01485010 | cg01743962 |
| cg01486752 | cg01754037 |
| cg01492246 | cg01754155 |
| cg01498231 | cg01757209 |
| cg01499217 | cg01763173 |
| cg01504555 | cg01764954 |
| cg01505590 | cg01772385 |
| cg01505767 | cg01775260 |
| cg01506130 | cg01778450 |
| cg01506492 | cg01780109 |
| cg01507044 | cg01782227 |
| cg01507046 | cg01785417 |
| cg01511379 | cg01791407 |
| cg01514859 | cg01794473 |
| cg01518631 | cg01814098 |
| cg01522456 | cg01814945 |
| cg01532206 | cg01822124 |
| cg01544751 | cg01831896 |
| cg01548300 | cg01833212 |
| cg01549404 | cg01834210 |
| cg01555604 | cg01839688 |
| cg01556502 | cg01844352 |
| cg01558040 | cg01844539 |
| cg01562471 | cg01851208 |
| cg01563031 | cg01857475 |
| cg01564068 | cg01861574 |
| cg01565690 | cg01862172 |
| cg01566304 | cg01869273 |
| cg01573616 | cg01869826 |
| cg01583034 | cg01871428 |
| cg01583969 | cg01873234 |

TABLE I-continued

Pan Cancer Panel

| | |
|---|---|
| cg01876194 | cg02221750 |
| cg01885963 | cg02221866 |
| cg01890984 | cg02229097 |
| cg01893041 | cg02229993 |
| cg01908537 | cg02231729 |
| cg01911237 | cg02232273 |
| cg01912921 | cg02233216 |
| cg01922936 | cg02236651 |
| cg01940943 | cg02241397 |
| cg01947949 | cg02247561 |
| cg01948390 | cg02248320 |
| cg01949798 | cg02250071 |
| cg01950665 | cg02251557 |
| cg01952683 | cg02257090 |
| cg01955962 | cg02257750 |
| cg01962509 | cg02260353 |
| cg01962510 | cg02265056 |
| cg01966612 | cg02266348 |
| cg01967288 | cg02270183 |
| cg01969058 | cg02273903 |
| cg01970519 | cg02277383 |
| cg01970575 | cg02282626 |
| cg01970784 | cg02284150 |
| cg01978544 | cg02284587 |
| cg01981187 | cg02285922 |
| cg01984858 | cg02286547 |
| cg01992107 | cg02290238 |
| cg01995821 | cg02293228 |
| cg01998047 | cg02298956 |
| cg02002584 | cg02303897 |
| cg02005505 | cg02304863 |
| cg02012576 | cg02306127 |
| cg02012731 | cg02307033 |
| cg02014107 | cg02307605 |
| cg02020882 | cg02310733 |
| cg02028389 | cg02315971 |
| cg02030493 | cg02316216 |
| cg02033141 | cg02328010 |
| cg02034497 | cg02330121 |
| cg02048890 | cg02330494 |
| cg02052895 | cg02331143 |
| cg02059348 | cg02340915 |
| cg02062409 | cg02344926 |
| cg02065704 | cg02346970 |
| cg02072885 | cg02352687 |
| cg02078870 | cg02352723 |
| cg02079933 | cg02353937 |
| cg02086858 | cg02357043 |
| cg02096492 | cg02362467 |
| cg02101625 | cg02362970 |
| cg02110141 | cg02369195 |
| cg02114924 | cg02384967 |
| cg02115050 | cg02388709 |
| cg02115539 | cg02394263 |
| cg02120463 | cg02398045 |
| cg02120582 | cg02398612 |
| cg02126753 | cg02399645 |
| cg02128087 | cg02400449 |
| cg02132163 | cg02405503 |
| cg02132470 | cg02406285 |
| cg02134353 | cg02407785 |
| cg02136132 | cg02408333 |
| cg02138756 | cg02409108 |
| cg02144298 | cg02424378 |
| cg02151754 | cg02425263 |
| cg02162906 | cg02430347 |
| cg02169113 | cg02435495 |
| cg02169734 | cg02445664 |
| cg02172579 | cg02447380 |
| cg02174225 | cg02448922 |
| cg02180498 | cg02454595 |
| cg02196227 | cg02460997 |
| cg02200939 | cg02461665 |
| cg02202600 | cg02470625 |
| cg02202980 | cg02472291 |
| cg02205739 | cg02474799 |
| cg02215070 | cg02481778 |
| cg02219071 | cg02483484 |

TABLE I-continued

Pan Cancer Panel

| | |
|---|---|
| cg02485200 | cg02723311 |
| cg02486351 | cg02725055 |
| cg02487654 | cg02737782 |
| cg02492778 | cg02738081 |
| cg02492791 | cg02739708 |
| cg02503395 | cg02750883 |
| cg02506053 | cg02757194 |
| cg02510164 | cg02759151 |
| cg02511156 | cg02761345 |
| cg02513017 | cg02767177 |
| cg02513409 | cg02767539 |
| cg02527199 | cg02767960 |
| cg02532538 | cg02770946 |
| cg02537163 | cg02776035 |
| cg02539714 | cg02776314 |
| cg02547025 | cg02783889 |
| cg02551396 | cg02784301 |
| cg02552311 | cg02787320 |
| cg02554246 | cg02795700 |
| cg02557406 | cg02796773 |
| cg02557432 | cg02797548 |
| cg02558627 | cg02816363 |
| cg02560717 | cg02819231 |
| cg02565702 | cg02820717 |
| cg02567082 | cg02831090 |
| cg02574526 | cg02835214 |
| cg02583334 | cg02836020 |
| cg02584489 | cg02836541 |
| cg02593205 | cg02838118 |
| cg02595750 | cg02841941 |
| cg02596331 | cg02842629 |
| cg02602699 | cg02850812 |
| cg02604121 | cg02854695 |
| cg02608019 | cg02855409 |
| cg02617469 | cg02862354 |
| cg02617655 | cg02862904 |
| cg02618553 | cg02866454 |
| cg02620228 | cg02867728 |
| cg02620694 | cg02871940 |
| cg02622885 | cg02873868 |
| cg02624855 | cg02874371 |
| cg02627531 | cg02876237 |
| cg02628801 | cg02877791 |
| cg02630553 | cg02882044 |
| cg02633073 | cg02883595 |
| cg02636497 | cg02885694 |
| cg02637978 | cg02886549 |
| cg02638057 | cg02888838 |
| cg02639285 | cg02888906 |
| cg02639993 | cg02891774 |
| cg02643218 | cg02892350 |
| cg02649987 | cg02892595 |
| cg02651961 | cg02892898 |
| cg02654360 | cg02893482 |
| cg02655739 | cg02899206 |
| cg02657292 | cg02905065 |
| cg02659086 | cg02906238 |
| cg02659794 | cg02915746 |
| cg02660823 | cg02916964 |
| cg02664993 | cg02917917 |
| cg02665570 | cg02918146 |
| cg02666434 | cg02918224 |
| cg02666504 | cg02921003 |
| cg02669964 | cg02921269 |
| cg02671646 | cg02921583 |
| cg02673256 | cg02927655 |
| cg02687055 | cg02929073 |
| cg02688760 | cg02930242 |
| cg02690609 | cg02933119 |
| cg02692405 | cg02934500 |
| cg02701278 | cg02938682 |
| cg02708401 | cg02939019 |
| cg02711801 | cg02942594 |
| cg02712555 | cg02945007 |
| cg02713068 | cg02951059 |
| cg02713266 | cg02951206 |
| cg02716516 | cg02951568 |
| cg02717437 | cg02952978 |

TABLE I-continued

Pan Cancer Panel

| | |
|---|---|
| cg02954735 | cg03259494 |
| cg02955219 | cg03265944 |
| cg02958718 | cg03273700 |
| cg02962318 | cg03279535 |
| cg02968116 | cg03288419 |
| cg02971481 | cg03290040 |
| cg02977761 | cg03297593 |
| cg02978421 | cg03307911 |
| cg02980693 | cg03309367 |
| cg02982690 | cg03309726 |
| cg02982793 | cg03311339 |
| cg02983203 | cg03311459 |
| cg02993259 | cg03313212 |
| cg02995055 | cg03315058 |
| cg03001116 | cg03321003 |
| cg03001832 | cg03324578 |
| cg03003689 | cg03328664 |
| cg03004714 | cg03332113 |
| cg03015433 | cg03334130 |
| cg03016097 | cg03334540 |
| cg03016991 | cg03342084 |
| cg03024517 | cg03342530 |
| cg03024536 | cg03347559 |
| cg03031959 | cg03347944 |
| cg03038003 | cg03352181 |
| cg03040279 | cg03356115 |
| cg03052869 | cg03356760 |
| cg03053575 | cg03364193 |
| cg03054643 | cg03365985 |
| cg03057213 | cg03366439 |
| cg03059112 | cg03366925 |
| cg03060802 | cg03369344 |
| cg03065202 | cg03369477 |
| cg03071143 | cg03382304 |
| cg03081134 | cg03383295 |
| cg03082580 | cg03386480 |
| cg03088791 | cg03387066 |
| cg03089869 | cg03391040 |
| cg03096401 | cg03392673 |
| cg03098937 | cg03393966 |
| cg03100040 | cg03397750 |
| cg03103035 | cg03405315 |
| cg03103770 | cg03410359 |
| cg03108238 | cg03410436 |
| cg03113285 | cg03411979 |
| cg03116642 | cg03415695 |
| cg03122735 | cg03424727 |
| cg03125329 | cg03425504 |
| cg03132532 | cg03427543 |
| cg03141007 | cg03430348 |
| cg03141069 | cg03430923 |
| cg03141620 | cg03431079 |
| cg03143697 | cg03434847 |
| cg03143742 | cg03437204 |
| cg03147990 | cg03443751 |
| cg03148427 | cg03446195 |
| cg03153658 | cg03450370 |
| cg03157531 | cg03455458 |
| cg03159947 | cg03462055 |
| cg03165343 | cg03465206 |
| cg03168582 | cg03467027 |
| cg03169767 | cg03468349 |
| cg03170611 | cg03470396 |
| cg03175305 | cg03472672 |
| cg03181829 | cg03476291 |
| cg03188118 | cg03479657 |
| cg03189990 | cg03485262 |
| cg03191830 | cg03495059 |
| cg03192963 | cg03496713 |
| cg03202738 | cg03502284 |
| cg03209812 | cg03506609 |
| cg03210277 | cg03506979 |
| cg03217173 | cg03513246 |
| cg03223126 | cg03521258 |
| cg03223733 | cg03524308 |
| cg03238298 | cg03525011 |
| cg03255556 | cg03526256 |
| cg03257575 | cg03532274 |

TABLE I-continued

Pan Cancer Panel

| | |
|---|---|
| cg03535663 | cg03806238 |
| cg03536983 | cg03808158 |
| cg03537779 | cg03809147 |
| cg03544918 | cg03817671 |
| cg03545133 | cg03817911 |
| cg03547745 | cg03818920 |
| cg03552151 | cg03818977 |
| cg03552992 | cg03818992 |
| cg03554817 | cg03822259 |
| cg03556393 | cg03824617 |
| cg03556653 | cg03836414 |
| cg03559229 | cg03839661 |
| cg03562044 | cg03843031 |
| cg03577052 | cg03846951 |
| cg03586803 | cg03860020 |
| cg03598499 | cg03860859 |
| cg03603214 | cg03861105 |
| cg03603951 | cg03863616 |
| cg03604840 | cg03871549 |
| cg03607117 | cg03880509 |
| cg03607359 | cg03884587 |
| cg03608167 | cg03884792 |
| cg03609148 | cg03894174 |
| cg03609308 | cg03896436 |
| cg03611007 | cg03899372 |
| cg03612722 | cg03900646 |
| cg03613077 | cg03901784 |
| cg03615913 | cg03909781 |
| cg03621100 | cg03911494 |
| cg03626278 | cg03920233 |
| cg03626734 | cg03921179 |
| cg03631864 | cg03921416 |
| cg03638874 | cg03921599 |
| cg03648780 | cg03927893 |
| cg03650154 | cg03929741 |
| cg03662422 | cg03930088 |
| cg03663746 | cg03938598 |
| cg03668475 | cg03940620 |
| cg03673687 | cg03947464 |
| cg03675739 | cg03954442 |
| cg03681341 | cg03961800 |
| cg03691812 | cg03974423 |
| cg03694261 | cg03978375 |
| cg03695666 | cg03979582 |
| cg03699307 | cg03980991 |
| cg03701001 | cg03985136 |
| cg03701745 | cg03986989 |
| cg03704912 | cg03991848 |
| cg03707948 | cg03998871 |
| cg03710481 | cg04005725 |
| cg03711182 | cg04008429 |
| cg03712038 | cg04010471 |
| cg03717315 | cg04011182 |
| cg03719634 | cg04012592 |
| cg03721976 | cg04012924 |
| cg03722871 | cg04017769 |
| cg03735847 | cg04022379 |
| cg03738134 | cg04027074 |
| cg03741406 | cg04028634 |
| cg03751813 | cg04044297 |
| cg03753681 | cg04046599 |
| cg03753849 | cg04049102 |
| cg03754311 | cg04051458 |
| cg03756448 | cg04054012 |
| cg03757145 | cg04057016 |
| cg03757871 | cg04058593 |
| cg03767822 | cg04072843 |
| cg03768777 | cg04073970 |
| cg03770147 | cg04076682 |
| cg03771448 | cg04083712 |
| cg03774026 | cg04083751 |
| cg03776464 | cg04083753 |
| cg03778788 | cg04085025 |
| cg03780545 | cg04089426 |
| cg03785281 | cg04092682 |
| cg03786924 | cg04095732 |
| cg03801902 | cg04099652 |
| cg03802907 | cg04106782 |

TABLE I-continued

Pan Cancer Panel

| | |
|---|---|
| cg04110544 | cg04417028 |
| cg04112845 | cg04424930 |
| cg04125371 | cg04430835 |
| cg04133572 | cg04435719 |
| cg04134305 | cg04437841 |
| cg04140862 | cg04438814 |
| cg04141379 | cg04439623 |
| cg04145287 | cg04449512 |
| cg04148762 | cg04450862 |
| cg04156369 | cg04454506 |
| cg04159901 | cg04457626 |
| cg04167903 | cg04461388 |
| cg04171539 | cg04468564 |
| cg04171853 | cg04480903 |
| cg04175417 | cg04487506 |
| cg04176674 | cg04489069 |
| cg04180299 | cg04493931 |
| cg04188397 | cg04494789 |
| cg04197823 | cg04501188 |
| cg04199931 | cg04504095 |
| cg04199943 | cg04513669 |
| cg04206517 | cg04515583 |
| cg04209650 | cg04516083 |
| cg04216289 | cg04524120 |
| cg04219247 | cg04524652 |
| cg04219613 | cg04525496 |
| cg04220088 | cg04534504 |
| cg04220579 | cg04539573 |
| cg04227789 | cg04539574 |
| cg04232325 | cg04543012 |
| cg04234680 | cg04547554 |
| cg04235146 | cg04547588 |
| cg04243181 | cg04554033 |
| cg04245373 | cg04555982 |
| cg04258811 | cg04557953 |
| cg04261877 | cg04559178 |
| cg04262938 | cg04566848 |
| cg04269188 | cg04568116 |
| cg04271801 | cg04569381 |
| cg04274487 | cg04572161 |
| cg04278225 | cg04577625 |
| cg04281219 | cg04578997 |
| cg04282206 | cg04580029 |
| cg04283751 | cg04583043 |
| cg04285443 | cg04583285 |
| cg04292359 | cg04584833 |
| cg04297664 | cg04593780 |
| cg04307977 | cg04602387 |
| cg04309212 | cg04604884 |
| cg04315947 | cg04605151 |
| cg04317977 | cg04614008 |
| cg04319464 | cg04614625 |
| cg04321580 | cg04614997 |
| cg04322105 | cg04618002 |
| cg04324727 | cg04618068 |
| cg04342092 | cg04632671 |
| cg04343407 | cg04633513 |
| cg04352026 | cg04633600 |
| cg04352676 | cg04635736 |
| cg04356980 | cg04637598 |
| cg04360049 | cg04645567 |
| cg04361852 | cg04653710 |
| cg04362858 | cg04657224 |
| cg04366249 | cg04657461 |
| cg04370807 | cg04658772 |
| cg04371288 | cg04660816 |
| cg04378874 | cg04661674 |
| cg04380513 | cg04663870 |
| cg04385144 | cg04673837 |
| cg04385733 | cg04674803 |
| cg04389422 | cg04677163 |
| cg04389426 | cg04678565 |
| cg04391222 | cg04682916 |
| cg04396685 | cg04697775 |
| cg04399418 | cg04722620 |
| cg04401038 | cg04727332 |
| cg04401710 | cg04730314 |
| cg04413680 | cg04736112 |

TABLE I-continued

Pan Cancer Panel

| |
|---|
| cg04744134 |
| cg04753439 |
| cg04757428 |
| cg04759335 |
| cg04760021 |
| cg04766136 |
| cg04769392 |
| cg04772326 |
| cg04775668 |
| cg04777312 |
| cg04782667 |
| cg04787343 |
| cg04796763 |
| cg04797985 |
| cg04805619 |
| cg04810377 |
| cg04815758 |
| cg04821107 |
| cg04822330 |
| cg04822808 |
| cg04824711 |
| cg04828458 |
| cg04830146 |
| cg04832767 |
| cg04836221 |
| cg04838747 |
| cg04839422 |
| cg04844977 |
| cg04845053 |
| cg04858616 |
| cg04861263 |
| cg04863950 |
| cg04865265 |
| cg04870212 |
| cg04873963 |
| cg04877901 |
| cg04880063 |
| cg04880618 |
| cg04884481 |
| cg04889106 |
| cg04890495 |
| cg04892170 |
| cg04892391 |
| cg04897742 |
| cg04912566 |
| cg04920227 |
| cg04922833 |
| cg04923576 |
| cg04932056 |
| cg04932544 |
| cg04939555 |
| cg04941721 |
| cg04948038 |
| cg04953079 |
| cg04964944 |
| cg04965141 |
| cg04968835 |
| cg04970150 |
| cg04972341 |
| cg04974587 |
| cg04975330 |
| cg04987465 |
| cg04988287 |
| cg04996355 |
| cg04998420 |
| cg05000136 |
| cg05004321 |
| cg05004940 |
| cg05011838 |
| cg05014211 |
| cg05021796 |
| cg05022306 |
| cg05026102 |
| cg05027458 |
| cg05028467 |
| cg05032399 |
| cg05037168 |
| cg05039463 |
| cg05040544 |
| cg05040584 |
| cg05041658 |
| cg05044739 |
| cg05052633 |
| cg05052898 |
| cg05056142 |
| cg05060672 |
| cg05062612 |
| cg05063339 |
| cg05063412 |
| cg05064297 |
| cg05065669 |
| cg05071577 |
| cg05071623 |
| cg05072848 |
| cg05075833 |
| cg05084391 |
| cg05086074 |
| cg05086811 |
| cg05090851 |
| cg05091519 |
| cg05094548 |
| cg05095123 |
| cg05098471 |
| cg05098876 |
| cg05099909 |
| cg05102581 |
| cg05103231 |
| cg05103387 |
| cg05109981 |
| cg05110787 |
| cg05119363 |
| cg05119480 |
| cg05121790 |
| cg05122861 |
| cg05124235 |
| cg05125578 |
| cg05127369 |
| cg05127456 |
| cg05129951 |
| cg05133370 |
| cg05139434 |
| cg05140069 |
| cg05148722 |
| cg05152561 |
| cg05153364 |
| cg05155840 |
| cg05156550 |
| cg05167782 |
| cg05173373 |
| cg05173737 |
| cg05194447 |
| cg05195612 |
| cg05196820 |
| cg05197625 |
| cg05203877 |
| cg05208423 |
| cg05209770 |
| cg05214218 |
| cg05217962 |
| cg05224998 |
| cg05228284 |
| cg05228634 |
| cg05235392 |
| cg05237001 |
| cg05249644 |
| cg05257472 |
| cg05261559 |
| cg05263743 |
| cg05264446 |
| cg05270922 |
| cg05277991 |
| cg05284582 |
| cg05287817 |
| cg05288475 |
| cg05294936 |
| cg05295494 |

TABLE I-continued

Pan Cancer Panel

| | |
|---|---|
| cg05296192 | cg05627083 |
| cg05298677 | cg05628771 |
| cg05302784 | cg05629186 |
| cg05306225 | cg05633190 |
| cg05307923 | cg05638929 |
| cg05312305 | cg05645404 |
| cg05322217 | cg05657805 |
| cg05323731 | cg05661333 |
| cg05329888 | cg05667158 |
| cg05331082 | cg05667817 |
| cg05332077 | cg05670408 |
| cg05332887 | cg05676541 |
| cg05336698 | cg05677402 |
| cg05346841 | cg05681826 |
| cg05347473 | cg05682719 |
| cg05356308 | cg05683504 |
| cg05356662 | cg05684406 |
| cg05356738 | cg05688651 |
| cg05366156 | cg05692837 |
| cg05367443 | cg05702737 |
| cg05371993 | cg05702851 |
| cg05372242 | cg05707458 |
| cg05376505 | cg05714219 |
| cg05376611 | cg05719720 |
| cg05377226 | cg05722552 |
| cg05385047 | cg05724965 |
| cg05390530 | cg05725531 |
| cg05396178 | cg05730283 |
| cg05402599 | cg05739190 |
| cg05406943 | cg05740895 |
| cg05411953 | cg05747105 |
| cg05412664 | cg05750029 |
| cg05419671 | cg05751100 |
| cg05426702 | cg05758094 |
| cg05428436 | cg05758434 |
| cg05428770 | cg05760393 |
| cg05432973 | cg05764240 |
| cg05434115 | cg05768702 |
| cg05435286 | cg05770030 |
| cg05446010 | cg05775742 |
| cg05454237 | cg05775895 |
| cg05461906 | cg05777716 |
| cg05469285 | cg05787193 |
| cg05470389 | cg05793299 |
| cg05481991 | cg05804949 |
| cg05482973 | cg05817664 |
| cg05488043 | cg05820312 |
| cg05495011 | cg05820448 |
| cg05502312 | cg05829482 |
| cg05508067 | cg05831823 |
| cg05508761 | cg05833894 |
| cg05513983 | cg05837253 |
| cg05524529 | cg05842391 |
| cg05530751 | cg05843841 |
| cg05533953 | cg05851163 |
| cg05542661 | cg05852040 |
| cg05542957 | cg05854826 |
| cg05547888 | cg05857941 |
| cg05554936 | cg05863587 |
| cg05557209 | cg05869503 |
| cg05565239 | cg05871997 |
| cg05568274 | cg05875032 |
| cg05568797 | cg05882426 |
| cg05573182 | cg05891474 |
| cg05573997 | cg05893300 |
| cg05576451 | cg05899726 |
| cg05578357 | cg05906740 |
| cg05578989 | cg05907237 |
| cg05580181 | cg05908775 |
| cg05585821 | cg05911003 |
| cg05598845 | cg05913514 |
| cg05603546 | cg05916744 |
| cg05605299 | cg05919561 |
| cg05608159 | cg05920090 |
| cg05613002 | cg05924445 |
| cg05619888 | cg05928649 |
| cg05624214 | cg05930133 |
| cg05625889 | cg05935052 |

TABLE I-continued

Pan Cancer Panel

| | |
|---|---|
| cg05937496 | cg06269673 |
| cg05938671 | cg06274671 |
| cg05941624 | cg06283368 |
| cg05949800 | cg06285590 |
| cg05949903 | cg06285648 |
| cg05951864 | cg06287318 |
| cg05952925 | cg06289589 |
| cg05953927 | cg06292947 |
| cg05956498 | cg06296570 |
| cg05962239 | cg06299537 |
| cg05963618 | cg06305340 |
| cg05970790 | cg06315607 |
| cg05975727 | cg06319033 |
| cg05978988 | cg06320134 |
| cg05986781 | cg06321345 |
| cg05989429 | cg06322891 |
| cg05990544 | cg06323837 |
| cg05991857 | cg06326971 |
| cg05994148 | cg06327267 |
| cg05995135 | cg06331595 |
| cg05995866 | cg06332859 |
| cg06001237 | cg06335741 |
| cg06008470 | cg06341054 |
| cg06011285 | cg06345952 |
| cg06011292 | cg06350353 |
| cg06017917 | cg06353127 |
| cg06027057 | cg06353330 |
| cg06030619 | cg06368118 |
| cg06035247 | cg06369090 |
| cg06035702 | cg06369833 |
| cg06040683 | cg06371306 |
| cg06041595 | cg06376016 |
| cg06045408 | cg06377152 |
| cg06046431 | cg06377278 |
| cg06053738 | cg06381123 |
| cg06055013 | cg06382894 |
| cg06055551 | cg06392318 |
| cg06059849 | cg06395091 |
| cg06060853 | cg06396649 |
| cg06065141 | cg06403244 |
| cg06065225 | cg06406719 |
| cg06065743 | cg06407366 |
| cg06072021 | cg06407634 |
| cg06073471 | cg06408864 |
| cg06078334 | cg06409432 |
| cg06080005 | cg06415582 |
| cg06082745 | cg06424594 |
| cg06100368 | cg06439293 |
| cg06102403 | cg06441668 |
| cg06123396 | cg06443175 |
| cg06123544 | cg06447552 |
| cg06123783 | cg06448961 |
| cg06124975 | cg06457811 |
| cg06128195 | cg06458469 |
| cg06131143 | cg06458554 |
| cg06161738 | cg06462964 |
| cg06163735 | cg06464594 |
| cg06172475 | cg06473927 |
| cg06177860 | cg06476192 |
| cg06188670 | cg06476344 |
| cg06193169 | cg06478457 |
| cg06193383 | cg06479755 |
| cg06194536 | cg06480249 |
| cg06197981 | cg06481158 |
| cg06198190 | cg06482074 |
| cg06202686 | cg06487247 |
| cg06203207 | cg06488775 |
| cg06205432 | cg06490744 |
| cg06214770 | cg06491924 |
| cg06217862 | cg06493473 |
| cg06225133 | cg06493664 |
| cg06226283 | cg06499484 |
| cg06226567 | cg06500654 |
| cg06241792 | cg06503907 |
| cg06247015 | cg06508879 |
| cg06248179 | cg06512974 |
| cg06251832 | cg06523022 |
| cg06263193 | cg06525293 |

TABLE I-continued

Pan Cancer Panel

| | |
|---|---|
| cg06531007 | cg06782692 |
| cg06532037 | cg06785746 |
| cg06533200 | cg06787716 |
| cg06537829 | cg06787731 |
| cg06543087 | cg06787764 |
| cg06545361 | cg06791151 |
| cg06546406 | cg06792347 |
| cg06554200 | cg06795971 |
| cg06562297 | cg06802147 |
| cg06562865 | cg06802365 |
| cg06563086 | cg06802658 |
| cg06564523 | cg06809055 |
| cg06567227 | cg06811478 |
| cg06567525 | cg06820586 |
| cg06570167 | cg06822120 |
| cg06573644 | cg06829893 |
| cg06580371 | cg06830555 |
| cg06582752 | cg06833203 |
| cg06602857 | cg06837311 |
| cg06604690 | cg06838175 |
| cg06606003 | cg06843320 |
| cg06609310 | cg06845943 |
| cg06615189 | cg06848047 |
| cg06616806 | cg06849515 |
| cg06620911 | cg06849719 |
| cg06625414 | cg06851941 |
| cg06626087 | cg06861209 |
| cg06626126 | cg06862167 |
| cg06629767 | cg06862545 |
| cg06631603 | cg06864853 |
| cg06633429 | cg06867829 |
| cg06636316 | cg06870284 |
| cg06636971 | cg06872519 |
| cg06637963 | cg06882758 |
| cg06650115 | cg06885524 |
| cg06654905 | cg06887260 |
| cg06657529 | cg06887275 |
| cg06664930 | cg06888942 |
| cg06668844 | cg06890432 |
| cg06672317 | cg06892005 |
| cg06677538 | cg06893138 |
| cg06685177 | cg06893834 |
| cg06685724 | cg06897264 |
| cg06689205 | cg06899530 |
| cg06690760 | cg06901369 |
| cg06692745 | cg06911121 |
| cg06694137 | cg06918887 |
| cg06699617 | cg06919916 |
| cg06700856 | cg06923622 |
| cg06701027 | cg06928346 |
| cg06704170 | cg06931615 |
| cg06705435 | cg06936079 |
| cg06719671 | cg06936768 |
| cg06720017 | cg06937552 |
| cg06721528 | cg06945523 |
| cg06722144 | cg06945936 |
| cg06722792 | cg06947852 |
| cg06727510 | cg06949053 |
| cg06728579 | cg06952671 |
| cg06734271 | cg06953252 |
| cg06739403 | cg06956232 |
| cg06739520 | cg06958567 |
| cg06741043 | cg06959053 |
| cg06742044 | cg06959514 |
| cg06744574 | cg06960698 |
| cg06744978 | cg06963053 |
| cg06747745 | cg06967120 |
| cg06749592 | cg06969287 |
| cg06755413 | cg06970228 |
| cg06759058 | cg06974483 |
| cg06763823 | cg06974515 |
| cg06765035 | cg06974871 |
| cg06768203 | cg06976202 |
| cg06775072 | cg06978388 |
| cg06776588 | cg06982544 |
| cg06779469 | cg06983586 |
| cg06780705 | cg06985934 |
| cg06780839 | cg06996609 |

TABLE I-continued

Pan Cancer Panel

| |
|---|
| cg06997305 |
| cg07010314 |
| cg07012770 |
| cg07015190 |
| cg07016493 |
| cg07017175 |
| cg07017901 |
| cg07025274 |
| cg07025949 |
| cg07026599 |
| cg07031839 |
| cg07045816 |
| cg07046852 |
| cg07058507 |
| cg07066369 |
| cg07066755 |
| cg07067241 |
| cg07070305 |
| cg07070934 |
| cg07072722 |
| cg07074316 |
| cg07077694 |
| cg07079445 |
| cg07085962 |
| cg07089235 |
| cg07089892 |
| cg07091779 |
| cg07097925 |
| cg07101782 |
| cg07113947 |
| cg07121078 |
| cg07121182 |
| cg07122245 |
| cg07126167 |
| cg07127225 |
| cg07127945 |
| cg07130366 |
| cg07132633 |
| cg07134033 |
| cg07134254 |
| cg07138603 |
| cg07139265 |
| cg07143052 |
| cg07147599 |
| cg07148818 |
| cg07148879 |
| cg07151445 |
| cg07152091 |
| cg07152591 |
| cg07155336 |
| cg07158434 |
| cg07160574 |
| cg07162257 |
| cg07162665 |
| cg07173547 |
| cg07175149 |
| cg07175507 |
| cg07180523 |
| cg07184836 |
| cg07190698 |
| cg07191393 |
| cg07193041 |
| cg07195282 |
| cg07195941 |
| cg07196014 |
| cg07197823 |
| cg07199619 |
| cg07201089 |
| cg07203452 |
| cg07207726 |
| cg07208703 |
| cg07209546 |
| cg07211381 |
| cg07212035 |
| cg07221635 |
| cg07221967 |
| cg07229938 |
| cg07230107 |
| cg07230380 |
| cg07231544 |
| cg07233677 |
| cg07235253 |
| cg07235638 |
| cg07251193 |
| cg07256029 |
| cg07261734 |
| cg07264124 |
| cg07265700 |
| cg07270078 |
| cg07276078 |
| cg07276861 |
| cg07279963 |
| cg07290739 |
| cg07291958 |
| cg07293520 |
| cg07297397 |
| cg07297582 |
| cg07301433 |
| cg07306531 |
| cg07309124 |
| cg07311521 |
| cg07312552 |
| cg07312854 |
| cg07313597 |
| cg07313705 |
| cg07314186 |
| cg07315993 |
| cg07316577 |
| cg07319626 |
| cg07326648 |
| cg07336230 |
| cg07337234 |
| cg07340574 |
| cg07344025 |
| cg07344492 |
| cg07346343 |
| cg07365816 |
| cg07366196 |
| cg07371290 |
| cg07376527 |
| cg07377876 |
| cg07381778 |
| cg07385577 |
| cg07386190 |
| cg07394446 |
| cg07398614 |
| cg07403338 |
| cg07408114 |
| cg07414961 |
| cg07420190 |
| cg07421806 |
| cg07423363 |
| cg07438288 |
| cg07438617 |
| cg07448606 |
| cg07449645 |
| cg07451080 |
| cg07452097 |
| cg07454491 |
| cg07457568 |
| cg07459525 |
| cg07464092 |
| cg07467520 |
| cg07469961 |
| cg07470489 |
| cg07482795 |
| cg07484673 |
| cg07484808 |
| cg07486895 |
| cg07488684 |
| cg07491796 |
| cg07498606 |
| cg07513622 |
| cg07519536 |
| cg07528097 |
| cg07536920 |

TABLE I-continued

Pan Cancer Panel

| | |
|---|---|
| cg07537876 | cg07813370 |
| cg07540542 | cg07813608 |
| cg07544244 | cg07817400 |
| cg07544748 | cg07817783 |
| cg07545317 | cg07824265 |
| cg07548580 | cg07824914 |
| cg07559696 | cg07825094 |
| cg07559730 | cg07826275 |
| cg07560517 | cg07835844 |
| cg07562483 | cg07836661 |
| cg07563569 | cg07838681 |
| cg07564088 | cg07844931 |
| cg07567630 | cg07847233 |
| cg07568344 | cg07847424 |
| cg07572131 | cg07847733 |
| cg07580038 | cg07850464 |
| cg07588964 | cg07864323 |
| cg07594209 | cg07869548 |
| cg07596524 | cg07870757 |
| cg07602492 | cg07872652 |
| cg07614306 | cg07876898 |
| cg07618175 | cg07877431 |
| cg07620039 | cg07879727 |
| cg07620889 | cg07881061 |
| cg07621104 | cg07890490 |
| cg07622404 | cg07896312 |
| cg07625131 | cg07900766 |
| cg07626874 | cg07900968 |
| cg07629187 | cg07904448 |
| cg07637123 | cg07914772 |
| cg07639650 | cg07914959 |
| cg07642566 | cg07916884 |
| cg07647353 | cg07917127 |
| cg07648581 | cg07917886 |
| cg07649491 | cg07919108 |
| cg07650252 | cg07925282 |
| cg07657131 | cg07926482 |
| cg07658614 | cg07927379 |
| cg07668802 | cg07929090 |
| cg07669489 | cg07940440 |
| cg07671603 | cg07944798 |
| cg07671858 | cg07944863 |
| cg07673866 | cg07945002 |
| cg07681728 | cg07951978 |
| cg07682547 | cg07959338 |
| cg07682663 | cg07963121 |
| cg07687766 | cg07964538 |
| cg07689503 | cg07966910 |
| cg07693037 | cg07973470 |
| cg07696033 | cg07976644 |
| cg07697981 | cg07980216 |
| cg07698901 | cg07980469 |
| cg07700369 | cg07980518 |
| cg07706362 | cg07984256 |
| cg07706463 | cg07985503 |
| cg07714565 | cg08009993 |
| cg07715387 | cg08012199 |
| cg07718308 | cg08015704 |
| cg07721822 | cg08023179 |
| cg07725355 | cg08024409 |
| cg07733620 | cg08026502 |
| cg07735777 | cg08027745 |
| cg07749724 | cg08028651 |
| cg07755173 | cg08033284 |
| cg07755653 | cg08038311 |
| cg07756196 | cg08042316 |
| cg07758574 | cg08044516 |
| cg07759377 | cg08045063 |
| cg07760910 | cg08047802 |
| cg07776163 | cg08048987 |
| cg07781332 | cg08063340 |
| cg07799366 | cg08069899 |
| cg07802571 | cg08074201 |
| cg07805238 | cg08074971 |
| cg07808348 | cg08079580 |
| cg07808546 | cg08083016 |
| cg07808661 | cg08089301 |
| cg07811212 | cg08089542 |

TABLE I-continued

Pan Cancer Panel

| | |
|---|---|
| cg08102141 | cg08378505 |
| cg08102256 | cg08378782 |
| cg08114257 | cg08382226 |
| cg08114373 | cg08382542 |
| cg08114476 | cg08382705 |
| cg08115387 | cg08384171 |
| cg08117032 | cg08385249 |
| cg08120331 | cg08385874 |
| cg08131100 | cg08397273 |
| cg08132931 | cg08405284 |
| cg08134829 | cg08406370 |
| cg08135278 | cg08407486 |
| cg08135850 | cg08410921 |
| cg08136813 | cg08416650 |
| cg08140343 | cg08418841 |
| cg08140387 | cg08419026 |
| cg08145698 | cg08424063 |
| cg08153160 | cg08424219 |
| cg08157579 | cg08428129 |
| cg08157672 | cg08430489 |
| cg08158570 | cg08441931 |
| cg08164617 | cg08445409 |
| cg08169659 | cg08446255 |
| cg08170140 | cg08447479 |
| cg08170869 | cg08448833 |
| cg08174718 | cg08460435 |
| cg08193467 | cg08463543 |
| cg08193910 | cg08466351 |
| cg08194677 | cg08468370 |
| cg08195448 | cg08473553 |
| cg08196106 | cg08478074 |
| cg08198711 | cg08478189 |
| cg08204843 | cg08482682 |
| cg08205230 | cg08487399 |
| cg08210629 | cg08496276 |
| cg08210727 | cg08504049 |
| cg08213098 | cg08505228 |
| cg08214689 | cg08506260 |
| cg08221811 | cg08511440 |
| cg08224646 | cg08514735 |
| cg08228715 | cg08517062 |
| cg08229488 | cg08517659 |
| cg08232264 | cg08518631 |
| cg08244959 | cg08519216 |
| cg08252855 | cg08522707 |
| cg08253188 | cg08535260 |
| cg08255782 | cg08541345 |
| cg08266417 | cg08548095 |
| cg08269389 | cg08548429 |
| cg08269900 | cg08552819 |
| cg08270258 | cg08553816 |
| cg08273666 | cg08555325 |
| cg08275602 | cg08565139 |
| cg08276739 | cg08572016 |
| cg08276889 | cg08576643 |
| cg08278648 | cg08577384 |
| cg08279184 | cg08591091 |
| cg08282385 | cg08592707 |
| cg08289140 | cg08599259 |
| cg08303146 | cg08603188 |
| cg08309706 | cg08604885 |
| cg08322205 | cg08607907 |
| cg08324950 | cg08617528 |
| cg08327269 | cg08620474 |
| cg08330183 | cg08623947 |
| cg08331513 | cg08625094 |
| cg08334310 | cg08625382 |
| cg08335854 | cg08625556 |
| cg08341316 | cg08635685 |
| cg08343755 | cg08642016 |
| cg08343881 | cg08644023 |
| cg08344081 | cg08644993 |
| cg08345372 | cg08651867 |
| cg08350814 | cg08653184 |
| cg08352292 | cg08658318 |
| cg08355316 | cg08658407 |
| cg08369872 | cg08659357 |
| cg08372619 | cg08669018 |

TABLE I-continued

Pan Cancer Panel

| | |
|---|---|
| cg08671133 | cg08962682 |
| cg08671343 | cg08965464 |
| cg08675193 | cg08984023 |
| cg08683343 | cg08990497 |
| cg08687901 | cg08992818 |
| cg08694014 | cg08993236 |
| cg08696866 | cg08995368 |
| cg08697092 | cg08998501 |
| cg08703613 | cg09000112 |
| cg08707078 | cg09003539 |
| cg08708599 | cg09010998 |
| cg08712068 | cg09017894 |
| cg08714121 | cg09019052 |
| cg08718398 | cg09024340 |
| cg08725962 | cg09033756 |
| cg08727443 | cg09041207 |
| cg08728856 | cg09043127 |
| cg08728892 | cg09044785 |
| cg08729135 | cg09052453 |
| cg08731623 | cg09067818 |
| cg08736446 | cg09068665 |
| cg08740729 | cg09079593 |
| cg08745498 | cg09085842 |
| cg08747591 | cg09093388 |
| cg08748615 | cg09103591 |
| cg08757742 | cg09106556 |
| cg08767710 | cg09130556 |
| cg08769300 | cg09133028 |
| cg08771731 | cg09135695 |
| cg08774231 | cg09140932 |
| cg08794135 | cg09150117 |
| cg08794939 | cg09150450 |
| cg08797606 | cg09150633 |
| cg08805144 | cg09153683 |
| cg08806611 | cg09158745 |
| cg08809418 | cg09159405 |
| cg08810584 | cg09160477 |
| cg08815286 | cg09163958 |
| cg08816037 | cg09168548 |
| cg08827358 | cg09169215 |
| cg08832069 | cg09170903 |
| cg08834269 | cg09177131 |
| cg08837308 | cg09183941 |
| cg08839858 | cg09185650 |
| cg08845439 | cg09185773 |
| cg08846783 | cg09185829 |
| cg08851719 | cg09191750 |
| cg08853659 | cg09196068 |
| cg08855568 | cg09198448 |
| cg08855729 | cg09202227 |
| cg08856879 | cg09210514 |
| cg08857159 | cg09219451 |
| cg08859513 | cg09224753 |
| cg08867893 | cg09229231 |
| cg08869573 | cg09231514 |
| cg08875180 | cg09235885 |
| cg08881159 | cg09239756 |
| cg08886727 | cg09243759 |
| cg08888625 | cg09248482 |
| cg08890360 | cg09249112 |
| cg08892705 | cg09260640 |
| cg08894362 | cg09265000 |
| cg08894629 | cg09267113 |
| cg08900833 | cg09267217 |
| cg08903381 | cg09267324 |
| cg08905325 | cg09267776 |
| cg08912051 | cg09268672 |
| cg08914844 | cg09273054 |
| cg08915922 | cg09275910 |
| cg08920748 | cg09279615 |
| cg08925398 | cg09280946 |
| cg08933227 | cg09282289 |
| cg08934846 | cg09290735 |
| cg08941714 | cg09290941 |
| cg08945452 | cg09306584 |
| cg08949339 | cg09307284 |
| cg08952590 | cg09312564 |
| cg08958015 | cg09313801 |

TABLE I-continued

Pan Cancer Panel

| | |
|---|---|
| cg09315391 | cg09608712 |
| cg09315918 | cg09611472 |
| cg09316894 | cg09615101 |
| cg09319202 | cg09628601 |
| cg09320746 | cg09631475 |
| cg09324698 | cg09640960 |
| cg09331704 | cg09642640 |
| cg09345512 | cg09648315 |
| cg09350548 | cg09650487 |
| cg09353063 | cg09654046 |
| cg09359907 | cg09666654 |
| cg09366357 | cg09667582 |
| cg09369381 | cg09668408 |
| cg09371047 | cg09669356 |
| cg09371439 | cg09670616 |
| cg09371456 | cg09674251 |
| cg09377064 | cg09679923 |
| cg09381701 | cg09681814 |
| cg09393675 | cg09690326 |
| cg09400281 | cg09691340 |
| cg09405169 | cg09693388 |
| cg09405612 | cg09695735 |
| cg09411252 | cg09697651 |
| cg09413557 | cg09700210 |
| cg09417889 | cg09700630 |
| cg09421347 | cg09701392 |
| cg09425356 | cg09710740 |
| cg09426197 | cg09717333 |
| cg09428893 | cg09717545 |
| cg09432613 | cg09722742 |
| cg09435617 | cg09723781 |
| cg09449030 | cg09727692 |
| cg09450020 | cg09728607 |
| cg09451960 | cg09741070 |
| cg09455182 | cg09742170 |
| cg09458673 | cg09742442 |
| cg09463047 | cg09745440 |
| cg09463882 | cg09749751 |
| cg09464194 | cg09750382 |
| cg09464488 | cg09753043 |
| cg09468912 | cg09758742 |
| cg09470640 | cg09764408 |
| cg09472203 | cg09765994 |
| cg09472360 | cg09775582 |
| cg09479015 | cg09785391 |
| cg09482777 | cg09793279 |
| cg09486260 | cg09793584 |
| cg09508531 | cg09802608 |
| cg09516362 | cg09804380 |
| cg09527109 | cg09809276 |
| cg09528265 | cg09810750 |
| cg09528884 | cg09813219 |
| cg09537107 | cg09819791 |
| cg09538135 | cg09822284 |
| cg09540952 | cg09823095 |
| cg09542745 | cg09824782 |
| cg09545293 | cg09826587 |
| cg09546168 | cg09827065 |
| cg09546921 | cg09848789 |
| cg09547767 | cg09852007 |
| cg09552692 | cg09852693 |
| cg09553358 | cg09854653 |
| cg09559047 | cg09857830 |
| cg09559792 | cg09858237 |
| cg09561458 | cg09859179 |
| cg09563244 | cg09859456 |
| cg09564020 | cg09865339 |
| cg09564101 | cg09865760 |
| cg09567473 | cg09867230 |
| cg09580567 | cg09877593 |
| cg09586080 | cg09885086 |
| cg09592603 | cg09885499 |
| cg09593184 | cg09889291 |
| cg09601704 | cg09892203 |
| cg09601770 | cg09906488 |
| cg09603188 | cg09906751 |
| cg09605726 | cg09908474 |
| cg09608387 | cg09909671 |

TABLE I-continued

Pan Cancer Panel

| | |
|---|---|
| cg09913544 | cg10242089 |
| cg09916572 | cg10243398 |
| cg09927508 | cg10247585 |
| cg09933058 | cg10259735 |
| cg09936190 | cg10266394 |
| cg09936645 | cg10272779 |
| cg09942248 | cg10273340 |
| cg09947186 | cg10291288 |
| cg09949949 | cg10291555 |
| cg09952946 | cg10293093 |
| cg09956859 | cg10300229 |
| cg09967877 | cg10312211 |
| cg09968391 | cg10316381 |
| cg09972364 | cg10316989 |
| cg09974136 | cg10317807 |
| cg09979256 | cg10328157 |
| cg09981184 | cg10330024 |
| cg09988062 | cg10333802 |
| cg09996156 | cg10336707 |
| cg09997760 | cg10342908 |
| cg09998133 | cg10348922 |
| cg09998229 | cg10350352 |
| cg10004574 | cg10365447 |
| cg10025396 | cg10366407 |
| cg10025443 | cg10370599 |
| cg10026473 | cg10377903 |
| cg10028348 | cg10381455 |
| cg10036727 | cg10392164 |
| cg10042106 | cg10398590 |
| cg10042319 | cg10408778 |
| cg10062141 | cg10418567 |
| cg10069638 | cg10421688 |
| cg10072850 | cg10434152 |
| cg10092374 | cg10437806 |
| cg10095938 | cg10443195 |
| cg10096161 | cg10445911 |
| cg10096177 | cg10449070 |
| cg10104986 | cg10453390 |
| cg10108389 | cg10457056 |
| cg10111450 | cg10461004 |
| cg10113334 | cg10463708 |
| cg10115191 | cg10473508 |
| cg10118828 | cg10474350 |
| cg10124651 | cg10477603 |
| cg10126409 | cg10480343 |
| cg10128164 | cg10496915 |
| cg10129816 | cg10497692 |
| cg10135588 | cg10507402 |
| cg10140114 | cg10515332 |
| cg10141019 | cg10515753 |
| cg10148270 | cg10516832 |
| cg10151741 | cg10517014 |
| cg10156125 | cg10517814 |
| cg10157203 | cg10518543 |
| cg10158080 | cg10523966 |
| cg10159349 | cg10534923 |
| cg10163776 | cg10536962 |
| cg10165331 | cg10538151 |
| cg10166205 | cg10542883 |
| cg10167296 | cg10544031 |
| cg10169177 | cg10544564 |
| cg10171063 | cg10547729 |
| cg10173182 | cg10548038 |
| cg10176059 | cg10548492 |
| cg10176160 | cg10548807 |
| cg10176687 | cg10555583 |
| cg10177238 | cg10557743 |
| cg10185885 | cg10569039 |
| cg10188732 | cg10569615 |
| cg10192047 | cg10579840 |
| cg10194844 | cg10580473 |
| cg10197432 | cg10580941 |
| cg10201807 | cg10581281 |
| cg10209083 | cg10588034 |
| cg10212705 | cg10588150 |
| cg10216353 | cg10589249 |
| cg10217327 | cg10590767 |
| cg10218490 | cg10592245 |

TABLE I-continued

Pan Cancer Panel

| | |
|---|---|
| cg10592690 | cg10778619 |
| cg10598066 | cg10779656 |
| cg10598353 | cg10790778 |
| cg10599985 | cg10798048 |
| cg10600178 | cg10799186 |
| cg10603183 | cg10802132 |
| cg10604396 | cg10804678 |
| cg10606059 | cg10809491 |
| cg10608256 | cg10810183 |
| cg10611186 | cg10811474 |
| cg10611863 | cg10815543 |
| cg10612237 | cg10817615 |
| cg10615091 | cg10821050 |
| cg10620273 | cg10821115 |
| cg10626559 | cg10822149 |
| cg10630028 | cg10827893 |
| cg10630240 | cg10832495 |
| cg10633931 | cg10832730 |
| cg10639440 | cg10832949 |
| cg10639888 | cg10833091 |
| cg10641986 | cg10836173 |
| cg10648670 | cg10836716 |
| cg10649525 | cg10836887 |
| cg10657367 | cg10838664 |
| cg10661724 | cg10841775 |
| cg10667877 | cg10847032 |
| cg10668041 | cg10851281 |
| cg10668399 | cg10851835 |
| cg10672508 | cg10852609 |
| cg10673839 | cg10853637 |
| cg10675666 | cg10858746 |
| cg10677909 | cg10861017 |
| cg10678018 | cg10864074 |
| cg10685144 | cg10864596 |
| cg10685945 | cg10864855 |
| cg10688328 | cg10871779 |
| cg10689512 | cg10880755 |
| cg10691592 | cg10883284 |
| cg10692118 | cg10884052 |
| cg10694030 | cg10884788 |
| cg10696724 | cg10885961 |
| cg10699264 | cg10886442 |
| cg10700334 | cg10890233 |
| cg10701051 | cg10895922 |
| cg10701282 | cg10897376 |
| cg10705236 | cg10899637 |
| cg10706069 | cg10900437 |
| cg10706100 | cg10900932 |
| cg10706454 | cg10901968 |
| cg10706642 | cg10908369 |
| cg10711209 | cg10911660 |
| cg10713073 | cg10911913 |
| cg10713773 | cg10914137 |
| cg10714492 | cg10918328 |
| cg10715930 | cg10923475 |
| cg10718940 | cg10925433 |
| cg10721116 | cg10926113 |
| cg10722846 | cg10938374 |
| cg10725121 | cg10943191 |
| cg10725547 | cg10943348 |
| cg10726226 | cg10949611 |
| cg10728469 | cg10950272 |
| cg10728756 | cg10951120 |
| cg10729325 | cg10954363 |
| cg10733249 | cg10955973 |
| cg10734734 | cg10971790 |
| cg10737195 | cg10974632 |
| cg10739095 | cg10975000 |
| cg10748160 | cg10977320 |
| cg10749413 | cg10983327 |
| cg10754670 | cg10986864 |
| cg10758227 | cg10989300 |
| cg10764541 | cg10989504 |
| cg10766373 | cg10994148 |
| cg10768690 | cg10995640 |
| cg10773309 | cg11005250 |
| cg10775273 | cg11007380 |
| cg10778599 | cg11007931 |

TABLE I-continued

Pan Cancer Panel

| | |
|---|---|
| cg11012953 | cg11200965 |
| cg11013544 | cg11201307 |
| cg11015038 | cg11206041 |
| cg11018723 | cg11206067 |
| cg11019211 | cg11208039 |
| cg11025763 | cg11218625 |
| cg11027354 | cg11223573 |
| cg11029301 | cg11224647 |
| cg11031064 | cg11237751 |
| cg11032070 | cg11240320 |
| cg11038073 | cg11241206 |
| cg11038280 | cg11242978 |
| cg11038774 | cg11244813 |
| cg11042361 | cg11245443 |
| cg11044163 | cg11246071 |
| cg11046315 | cg11248182 |
| cg11052668 | cg11248715 |
| cg11054379 | cg11249313 |
| cg11055358 | cg11251113 |
| cg11056409 | cg11252337 |
| cg11059483 | cg11257429 |
| cg11062418 | cg11258043 |
| cg11062677 | cg11258164 |
| cg11065506 | cg11259628 |
| cg11067756 | cg11262757 |
| cg11071762 | cg11262906 |
| cg11071960 | cg11263235 |
| cg11073571 | cg11263393 |
| cg11075316 | cg11267065 |
| cg11075416 | cg11267829 |
| cg11076617 | cg11270393 |
| cg11081186 | cg11274962 |
| cg11081729 | cg11278262 |
| cg11086760 | cg11278506 |
| cg11090139 | cg11279425 |
| cg11092616 | cg11279933 |
| cg11094122 | cg11281912 |
| cg11098493 | cg11283700 |
| cg11099006 | cg11285507 |
| cg11100602 | cg11286023 |
| cg11100798 | cg11287660 |
| cg11100836 | cg11292593 |
| cg11103652 | cg11294084 |
| cg11107669 | cg11296230 |
| cg11108676 | cg11297723 |
| cg11109374 | cg11302533 |
| cg11116776 | cg11303127 |
| cg11117108 | cg11305077 |
| cg11117633 | cg11306587 |
| cg11118396 | cg11313386 |
| cg11122493 | cg11315754 |
| cg11124426 | cg11316146 |
| cg11125787 | cg11316784 |
| cg11127711 | cg11320449 |
| cg11134155 | cg11326968 |
| cg11140785 | cg11334214 |
| cg11142406 | cg11342277 |
| cg11142826 | cg11343017 |
| cg11144056 | cg11345323 |
| cg11150664 | cg11348338 |
| cg11152298 | cg11352190 |
| cg11152364 | cg11352418 |
| cg11153872 | cg11352866 |
| cg11154608 | cg11353329 |
| cg11155707 | cg11353380 |
| cg11159091 | cg11358257 |
| cg11161828 | cg11360366 |
| cg11163901 | cg11360768 |
| cg11165313 | cg11371122 |
| cg11169461 | cg11373604 |
| cg11170727 | cg11374425 |
| cg11171224 | cg11376305 |
| cg11173422 | cg11377484 |
| cg11176990 | cg11378840 |
| cg11186405 | cg11381826 |
| cg11189251 | cg11383347 |
| cg11197015 | cg11386792 |
| cg11198358 | cg11387705 |

TABLE I-continued

Pan Cancer Panel

| | |
|---|---|
| cg11388325 | cg11566061 |
| cg11390468 | cg11567172 |
| cg11390957 | cg11569407 |
| cg11392855 | cg11569979 |
| cg11395536 | cg11571001 |
| cg11396791 | cg11571263 |
| cg11398523 | cg11576123 |
| cg11399097 | cg11583963 |
| cg11400401 | cg11587925 |
| cg11401682 | cg11590405 |
| cg11401866 | cg11591325 |
| cg11402700 | cg11591516 |
| cg11407741 | cg11593482 |
| cg11412935 | cg11595155 |
| cg11413715 | cg11596863 |
| cg11416076 | cg11600807 |
| cg11417653 | cg11607341 |
| cg11419456 | cg11610754 |
| cg11421604 | cg11612291 |
| cg11422045 | cg11613229 |
| cg11423323 | cg11621911 |
| cg11424198 | cg11623861 |
| cg11425254 | cg11628574 |
| cg11425280 | cg11628754 |
| cg11428482 | cg11631644 |
| cg11430245 | cg11638200 |
| cg11431820 | cg11643991 |
| cg11434468 | cg11644057 |
| cg11435087 | cg11647421 |
| cg11439004 | cg11654179 |
| cg11442717 | cg11654553 |
| cg11444379 | cg11654620 |
| cg11444428 | cg11655629 |
| cg11444607 | cg11657970 |
| cg11445323 | cg11661868 |
| cg11459006 | cg11662264 |
| cg11459714 | cg11664467 |
| cg11460029 | cg11665588 |
| cg11461030 | cg11666087 |
| cg11474250 | cg11667451 |
| cg11474317 | cg11671925 |
| cg11476211 | cg11672054 |
| cg11485463 | cg11676221 |
| cg11486350 | cg11679177 |
| cg11487705 | cg11684496 |
| cg11490941 | cg11686528 |
| cg11494123 | cg11687406 |
| cg11495854 | cg11688696 |
| cg11503720 | cg11691561 |
| cg11504515 | cg11692477 |
| cg11504897 | cg11694752 |
| cg11510060 | cg11695653 |
| cg11510557 | cg11696361 |
| cg11512800 | cg11696475 |
| cg11518359 | cg11697226 |
| cg11518945 | cg11698944 |
| cg11521404 | cg11706467 |
| cg11522018 | cg11708616 |
| cg11522812 | cg11715903 |
| cg11523538 | cg11716665 |
| cg11525479 | cg11720950 |
| cg11525941 | cg11721249 |
| cg11527373 | cg11723397 |
| cg11528832 | cg11727653 |
| cg11536457 | cg11729413 |
| cg11538128 | cg11729970 |
| cg11539424 | cg11732642 |
| cg11540007 | cg11734710 |
| cg11542224 | cg11737232 |
| cg11542789 | cg11737710 |
| cg11546106 | cg11737742 |
| cg11550126 | cg11738446 |
| cg11551257 | cg11739541 |
| cg11551740 | cg11739675 |
| cg11553248 | cg11740878 |
| cg11561737 | cg11747771 |
| cg11564981 | cg11750133 |
| cg11565355 | cg11750900 |

TABLE I-continued

Pan Cancer Panel

| | |
|---|---|
| cg11751927 | cg11963595 |
| cg11752440 | cg11963676 |
| cg11753239 | cg11967894 |
| cg11753867 | cg11968091 |
| cg11757144 | cg11972401 |
| cg11758861 | cg11973682 |
| cg11760700 | cg11980147 |
| cg11765438 | cg11980481 |
| cg11767181 | cg11985220 |
| cg11768886 | cg11992351 |
| cg11771234 | cg11992375 |
| cg11772643 | cg11993230 |
| cg11775417 | cg11996434 |
| cg11775528 | cg12005824 |
| cg11775605 | cg12013041 |
| cg11775837 | cg12014547 |
| cg11777390 | cg12015854 |
| cg11782779 | cg12019773 |
| cg11784071 | cg12020533 |
| cg11785166 | cg12020549 |
| cg11787288 | cg12024304 |
| cg11790681 | cg12024311 |
| cg11792653 | cg12025027 |
| cg11794649 | cg12027636 |
| cg11794877 | cg12033943 |
| cg11797092 | cg12034791 |
| cg11799819 | cg12038935 |
| cg11802864 | cg12040278 |
| cg11804724 | cg12040486 |
| cg11804775 | cg12041340 |
| cg11805669 | cg12042448 |
| cg11806442 | cg12042503 |
| cg11811216 | cg12042659 |
| cg11812069 | cg12043314 |
| cg11820517 | cg12046254 |
| cg11828108 | cg12048031 |
| cg11829072 | cg12048674 |
| cg11831043 | cg12055259 |
| cg11837274 | cg12056977 |
| cg11838688 | cg12057741 |
| cg11854154 | cg12059226 |
| cg11856078 | cg12060306 |
| cg11866527 | cg12062488 |
| cg11879480 | cg12064069 |
| cg11879536 | cg12066398 |
| cg11882252 | cg12066864 |
| cg11884230 | cg12070152 |
| cg11889265 | cg12071806 |
| cg11889692 | cg12074093 |
| cg11889769 | cg12074780 |
| cg11895474 | cg12077344 |
| cg11896633 | cg12080391 |
| cg11901043 | cg12082598 |
| cg11901188 | cg12082871 |
| cg11904590 | cg12083965 |
| cg11906038 | cg12084869 |
| cg11911648 | cg12087304 |
| cg11912765 | cg12092561 |
| cg11916219 | cg12097080 |
| cg11921270 | cg12101108 |
| cg11922371 | cg12104945 |
| cg11923957 | cg12108974 |
| cg11926764 | cg12109566 |
| cg11928730 | cg12110677 |
| cg11930114 | cg12119111 |
| cg11931727 | cg12121066 |
| cg11935854 | cg12128270 |
| cg11944428 | cg12132563 |
| cg11946336 | cg12136088 |
| cg11948055 | cg12145080 |
| cg11948456 | cg12150111 |
| cg11949831 | cg12152867 |
| cg11951910 | cg12153044 |
| cg11953272 | cg12164472 |
| cg11954479 | cg12164777 |
| cg11955541 | cg12169977 |
| cg11958643 | cg12177207 |
| cg11960115 | cg12178578 |

TABLE I-continued

Pan Cancer Panel

| | |
|---|---|
| cg12180984 | cg12387700 |
| cg12181634 | cg12391667 |
| cg12182940 | cg12392528 |
| cg12182991 | cg12393697 |
| cg12184864 | cg12394377 |
| cg12185399 | cg12396999 |
| cg12187115 | cg12397426 |
| cg12187657 | cg12400781 |
| cg12189880 | cg12405785 |
| cg12205244 | cg12411093 |
| cg12205729 | cg12414653 |
| cg12207120 | cg12420858 |
| cg12210040 | cg12435415 |
| cg12212657 | cg12439074 |
| cg12217936 | cg12441358 |
| cg12227762 | cg12443753 |
| cg12228245 | cg12448161 |
| cg12228659 | cg12449162 |
| cg12233208 | cg12449366 |
| cg12236045 | cg12452364 |
| cg12240767 | cg12456286 |
| cg12243375 | cg12457529 |
| cg12244581 | cg12466737 |
| cg12249227 | cg12469475 |
| cg12253819 | cg12473009 |
| cg12253830 | cg12476541 |
| cg12254291 | cg12477533 |
| cg12256538 | cg12480416 |
| cg12259256 | cg12482809 |
| cg12266841 | cg12484037 |
| cg12266953 | cg12484686 |
| cg12271199 | cg12485161 |
| cg12273811 | cg12487147 |
| cg12275348 | cg12489736 |
| cg12276768 | cg12492094 |
| cg12280407 | cg12498522 |
| cg12281798 | cg12500891 |
| cg12283120 | cg12500976 |
| cg12286569 | cg12501868 |
| cg12287025 | cg12503643 |
| cg12292531 | cg12505146 |
| cg12297030 | cg12508331 |
| cg12297619 | cg12511113 |
| cg12298212 | cg12513284 |
| cg12298905 | cg12514620 |
| cg12300292 | cg12514873 |
| cg12304599 | cg12518360 |
| cg12311057 | cg12520861 |
| cg12315302 | cg12523878 |
| cg12316475 | cg12527384 |
| cg12316865 | cg12536526 |
| cg12318400 | cg12537168 |
| cg12319507 | cg12537925 |
| cg12320306 | cg12538248 |
| cg12328890 | cg12541049 |
| cg12330330 | cg12545252 |
| cg12332415 | cg12545721 |
| cg12334247 | cg12547474 |
| cg12339905 | cg12550412 |
| cg12340947 | cg12551582 |
| cg12342334 | cg12555306 |
| cg12346504 | cg12558012 |
| cg12346874 | cg12558519 |
| cg12351660 | cg12559860 |
| cg12358524 | cg12561338 |
| cg12359315 | cg12563240 |
| cg12363807 | cg12563839 |
| cg12367520 | cg12566138 |
| cg12368524 | cg12568633 |
| cg12371386 | cg12573516 |
| cg12372692 | cg12581244 |
| cg12373208 | cg12582734 |
| cg12377578 | cg12585429 |
| cg12379940 | cg12586262 |
| cg12379948 | cg12586496 |
| cg12380339 | cg12587386 |
| cg12381164 | cg12588082 |
| cg12382902 | cg12589298 |

TABLE I-continued

Pan Cancer Panel

| | |
|---|---|
| cg12592716 | cg12845520 |
| cg12593303 | cg12850036 |
| cg12593608 | cg12850252 |
| cg12594716 | cg12851504 |
| cg12595016 | cg12853563 |
| cg12598803 | cg12853981 |
| cg12600289 | cg12859164 |
| cg12610867 | cg12868019 |
| cg12612104 | cg12872647 |
| cg12613402 | cg12874092 |
| cg12619536 | cg12879909 |
| cg12620443 | cg12883479 |
| cg12622139 | cg12886634 |
| cg12623648 | cg12886942 |
| cg12624667 | cg12891498 |
| cg12629875 | cg12895747 |
| cg12630336 | cg12902426 |
| cg12632097 | cg12908522 |
| cg12632573 | cg12909741 |
| cg12639324 | cg12910175 |
| cg12643049 | cg12914047 |
| cg12643366 | cg12919976 |
| cg12643689 | cg12920814 |
| cg12647165 | cg12921914 |
| cg12652174 | cg12924825 |
| cg12653917 | cg12926104 |
| cg12664560 | cg12929567 |
| cg12665504 | cg12934934 |
| cg12671336 | cg12936423 |
| cg12680730 | cg12936797 |
| cg12682392 | cg12938565 |
| cg12685200 | cg12940104 |
| cg12685731 | cg12942328 |
| cg12686016 | cg12943155 |
| cg12691382 | cg12945693 |
| cg12693702 | cg12949975 |
| cg12695989 | cg12953628 |
| cg12706983 | cg12954230 |
| cg12714014 | cg12962355 |
| cg12714180 | cg12966801 |
| cg12727462 | cg12968192 |
| cg12728517 | cg12970542 |
| cg12734954 | cg12970695 |
| cg12735820 | cg12970724 |
| cg12741345 | cg12976501 |
| cg12745764 | cg12978205 |
| cg12745769 | cg12978575 |
| cg12748332 | cg12981137 |
| cg12758636 | cg12985773 |
| cg12759298 | cg12986338 |
| cg12760327 | cg12989733 |
| cg12764921 | cg12992385 |
| cg12767281 | cg12998491 |
| cg12771118 | cg13000134 |
| cg12773604 | cg13002939 |
| cg12775884 | cg13002945 |
| cg12777448 | cg13008717 |
| cg12778476 | cg13008978 |
| cg12784241 | cg13011362 |
| cg12784598 | cg13016179 |
| cg12784848 | cg13021384 |
| cg12789062 | cg13021409 |
| cg12790391 | cg13023133 |
| cg12790592 | cg13024590 |
| cg12791192 | cg13027682 |
| cg12792011 | cg13031251 |
| cg12804278 | cg13031432 |
| cg12810233 | cg13042543 |
| cg12810313 | cg13047843 |
| cg12814529 | cg13047892 |
| cg12815987 | cg13050058 |
| cg12819417 | cg13050981 |
| cg12825804 | cg13055665 |
| cg12835256 | cg13056495 |
| cg12837084 | cg13065262 |
| cg12837552 | cg13067194 |
| cg12837896 | cg13070193 |
| cg12841273 | cg13070215 |

TABLE I-continued

Pan Cancer Panel

| | |
|---|---|
| cg13071476 | cg13286510 |
| cg13072057 | cg13298359 |
| cg13075263 | cg13299025 |
| cg13079047 | cg13307451 |
| cg13080151 | cg13308080 |
| cg13083436 | cg13309421 |
| cg13084429 | cg13319975 |
| cg13085414 | cg13320114 |
| cg13094036 | cg13322582 |
| cg13100764 | cg13323825 |
| cg13107975 | cg13326227 |
| cg13108181 | cg13330524 |
| cg13109300 | cg13332538 |
| cg13109397 | cg13334883 |
| cg13111733 | cg13336642 |
| cg13112361 | cg13337238 |
| cg13113115 | cg13337697 |
| cg13115661 | cg13338827 |
| cg13117031 | cg13340335 |
| cg13119884 | cg13342441 |
| cg13120771 | cg13348059 |
| cg13121120 | cg13348155 |
| cg13127309 | cg13351117 |
| cg13131185 | cg13351830 |
| cg13132965 | cg13355047 |
| cg13133420 | cg13359699 |
| cg13135031 | cg13360562 |
| cg13137376 | cg13361393 |
| cg13137533 | cg13362540 |
| cg13140564 | cg13362637 |
| cg13149662 | cg13365761 |
| cg13158344 | cg13368085 |
| cg13161961 | cg13369164 |
| cg13165109 | cg13369291 |
| cg13165472 | cg13376290 |
| cg13168407 | cg13378886 |
| cg13168683 | cg13380624 |
| cg13173260 | cg13383019 |
| cg13177786 | cg13384453 |
| cg13179469 | cg13386176 |
| cg13180809 | cg13386351 |
| cg13181079 | cg13388111 |
| cg13181745 | cg13390743 |
| cg13185030 | cg13393601 |
| cg13186286 | cg13395035 |
| cg13192788 | cg13395410 |
| cg13194994 | cg13400018 |
| cg13195923 | cg13401831 |
| cg13197406 | cg13404421 |
| cg13204512 | cg13405293 |
| cg13207797 | cg13412066 |
| cg13210260 | cg13414916 |
| cg13210403 | cg13415207 |
| cg13215078 | cg13417268 |
| cg13217116 | cg13419713 |
| cg13223402 | cg13419791 |
| cg13227105 | cg13420848 |
| cg13227697 | cg13421439 |
| cg13231951 | cg13424209 |
| cg13233166 | cg13425637 |
| cg13235817 | cg13426138 |
| cg13236378 | cg13427834 |
| cg13247581 | cg13432744 |
| cg13247671 | cg13436055 |
| cg13251269 | cg13436799 |
| cg13253980 | cg13437337 |
| cg13254898 | cg13437361 |
| cg13255096 | cg13438334 |
| cg13258039 | cg13439181 |
| cg13258989 | cg13440083 |
| cg13259296 | cg13444964 |
| cg13262310 | cg13445199 |
| cg13264473 | cg13447915 |
| cg13264741 | cg13447927 |
| cg13266630 | cg13448814 |
| cg13268132 | cg13449295 |
| cg13285189 | cg13451025 |
| cg13285637 | cg13451222 |

TABLE I-continued

Pan Cancer Panel

| | |
|---|---|
| cg13455700 | cg13605988 |
| cg13458335 | cg13607835 |
| cg13462028 | cg13609667 |
| cg13462843 | cg13615338 |
| cg13463054 | cg13617204 |
| cg13463683 | cg13617889 |
| cg13464924 | cg13618596 |
| cg13465955 | cg13618906 |
| cg13467254 | cg13620096 |
| cg13468764 | cg13620744 |
| cg13470341 | cg13629999 |
| cg13472882 | cg13632230 |
| cg13475388 | cg13632876 |
| cg13483916 | cg13634713 |
| cg13484295 | cg13636404 |
| cg13484581 | cg13636408 |
| cg13487102 | cg13636880 |
| cg13488395 | cg13640626 |
| cg13491481 | cg13643376 |
| cg13491690 | cg13643814 |
| cg13492103 | cg13644629 |
| cg13495850 | cg13647349 |
| cg13499966 | cg13648312 |
| cg13501181 | cg13649886 |
| cg13501359 | cg13650104 |
| cg13501793 | cg13650149 |
| cg13504245 | cg13652445 |
| cg13504570 | cg13652513 |
| cg13507506 | cg13655570 |
| cg13510327 | cg13661131 |
| cg13512069 | cg13661211 |
| cg13514129 | cg13662093 |
| cg13516820 | cg13665266 |
| cg13517567 | cg13670601 |
| cg13518792 | cg13670911 |
| cg13521097 | cg13683125 |
| cg13521908 | cg13683218 |
| cg13522244 | cg13686589 |
| cg13523528 | cg13690354 |
| cg13525837 | cg13690989 |
| cg13529912 | cg13694746 |
| cg13530158 | cg13695877 |
| cg13530621 | cg13699804 |
| cg13535593 | cg13700897 |
| cg13536757 | cg13702942 |
| cg13536876 | cg13703584 |
| cg13537781 | cg13708218 |
| cg13538845 | cg13708497 |
| cg13541961 | cg13710037 |
| cg13542964 | cg13710703 |
| cg13548601 | cg13714039 |
| cg13550107 | cg13714067 |
| cg13552710 | cg13716829 |
| cg13554489 | cg13719188 |
| cg13554744 | cg13724379 |
| cg13554903 | cg13730743 |
| cg13556659 | cg13736068 |
| cg13561476 | cg13740698 |
| cg13562911 | cg13744663 |
| cg13563903 | cg13746315 |
| cg13565301 | cg13747794 |
| cg13568334 | cg13749494 |
| cg13568946 | cg13750123 |
| cg13570982 | cg13750967 |
| cg13574390 | cg13758646 |
| cg13577493 | cg13758712 |
| cg13578447 | cg13761375 |
| cg13579428 | cg13762060 |
| cg13580857 | cg13764828 |
| cg13582072 | cg13766030 |
| cg13588054 | cg13768269 |
| cg13589330 | cg13769223 |
| cg13590336 | cg13773705 |
| cg13593479 | cg13773914 |
| cg13595904 | cg13776340 |
| cg13601427 | cg13782728 |
| cg13604337 | cg13784621 |
| cg13604887 | cg13785718 |

TABLE I-continued

Pan Cancer Panel

| | |
|---|---|
| cg13786801 | cg13952656 |
| cg13787982 | cg13952745 |
| cg13788258 | cg13955436 |
| cg13788592 | cg13955512 |
| cg13789548 | cg13957721 |
| cg13789775 | cg13965724 |
| cg13792037 | cg13969239 |
| cg13792045 | cg13971154 |
| cg13795264 | cg13975009 |
| cg13795465 | cg13975625 |
| cg13797228 | cg13979305 |
| cg13802457 | cg13980528 |
| cg13803214 | cg13980570 |
| cg13807970 | cg13984623 |
| cg13808240 | cg13987972 |
| cg13816282 | cg13993336 |
| cg13818875 | cg13993853 |
| cg13821072 | cg13995101 |
| cg13822158 | cg13995769 |
| cg13822726 | cg13997864 |
| cg13823553 | cg14008500 |
| cg13826167 | cg14012112 |
| cg13828183 | cg14015503 |
| cg13829980 | cg14018731 |
| cg13830081 | cg14021564 |
| cg13831922 | cg14022137 |
| cg13836270 | cg14026459 |
| cg13837913 | cg14028892 |
| cg13845147 | cg14035550 |
| cg13846866 | cg14036923 |
| cg13847066 | cg14038484 |
| cg13848566 | cg14041778 |
| cg13849454 | cg14044057 |
| cg13852218 | cg14045486 |
| cg13852879 | cg14046986 |
| cg13854983 | cg14048874 |
| cg13856711 | cg14049461 |
| cg13861122 | cg14051592 |
| cg13861524 | cg14052221 |
| cg13868165 | cg14055374 |
| cg13872965 | cg14057961 |
| cg13875120 | cg14059420 |
| cg13876163 | cg14066751 |
| cg13876462 | cg14067419 |
| cg13879442 | cg14074052 |
| cg13885320 | cg14081631 |
| cg13885965 | cg14084176 |
| cg13887004 | cg14084312 |
| cg13894748 | cg14087806 |
| cg13899314 | cg14089512 |
| cg13901737 | cg14089984 |
| cg13903378 | cg14090923 |
| cg13905264 | cg14093886 |
| cg13911393 | cg14096353 |
| cg13911723 | cg14097019 |
| cg13912673 | cg14097171 |
| cg13915212 | cg14098468 |
| cg13916322 | cg14099335 |
| cg13917712 | cg14101302 |
| cg13921956 | cg14107807 |
| cg13924755 | cg14114517 |
| cg13930105 | cg14114673 |
| cg13930300 | cg14117643 |
| cg13931559 | cg14119437 |
| cg13932362 | cg14122696 |
| cg13932603 | cg14123923 |
| cg13936125 | cg14128634 |
| cg13938881 | cg14135025 |
| cg13945578 | cg14136927 |
| cg13945644 | cg14140647 |
| cg13946902 | cg14140881 |
| cg13947666 | cg14141331 |
| cg13947892 | cg14142965 |
| cg13950625 | cg14145593 |
| cg13951042 | cg14146583 |
| cg13951527 | cg14149680 |
| cg13951572 | cg14150327 |
| cg13952031 | cg14154651 |

TABLE I-continued

Pan Cancer Panel

| | |
|---|---|
| cg14156760 | cg14272275 |
| cg14157855 | cg14275457 |
| cg14157947 | cg14276323 |
| cg14159790 | cg14277392 |
| cg14161579 | cg14278575 |
| cg14162034 | cg14282137 |
| cg14162120 | cg14283380 |
| cg14163229 | cg14283569 |
| cg14163665 | cg14283602 |
| cg14163802 | cg14286439 |
| cg14172603 | cg14287868 |
| cg14174099 | cg14288330 |
| cg14174215 | cg14291066 |
| cg14176132 | cg14291622 |
| cg14180718 | cg14293362 |
| cg14181169 | cg14294629 |
| cg14183693 | cg14294793 |
| cg14183976 | cg14298966 |
| cg14184277 | cg14304761 |
| cg14190674 | cg14307443 |
| cg14190761 | cg14309384 |
| cg14191292 | cg14311471 |
| cg14192160 | cg14311608 |
| cg14192858 | cg14312959 |
| cg14193886 | cg14314818 |
| cg14194048 | cg14316898 |
| cg14195122 | cg14318946 |
| cg14199276 | cg14320054 |
| cg14200979 | cg14320593 |
| cg14202478 | cg14322429 |
| cg14202910 | cg14326413 |
| cg14203032 | cg14326460 |
| cg14204255 | cg14326885 |
| cg14207210 | cg14327951 |
| cg14207954 | cg14329441 |
| cg14209005 | cg14334286 |
| cg14209793 | cg14335782 |
| cg14210694 | cg14336879 |
| cg14212266 | cg14339043 |
| cg14212504 | cg14339599 |
| cg14214865 | cg14340610 |
| cg14215776 | cg14344315 |
| cg14216029 | cg14345980 |
| cg14218042 | cg14347989 |
| cg14218513 | cg14348439 |
| cg14219599 | cg14349843 |
| cg14220081 | cg14351528 |
| cg14220654 | cg14354472 |
| cg14221039 | cg14355192 |
| cg14222879 | cg14360865 |
| cg14223395 | cg14364356 |
| cg14224937 | cg14365570 |
| cg14225021 | cg14368881 |
| cg14231871 | cg14369405 |
| cg14232289 | cg14370784 |
| cg14233355 | cg14372333 |
| cg14233568 | cg14372394 |
| cg14235416 | cg14373456 |
| cg14237975 | cg14378848 |
| cg14239329 | cg14381390 |
| cg14241138 | cg14381972 |
| cg14241323 | cg14385175 |
| cg14242042 | cg14385337 |
| cg14242958 | cg14393469 |
| cg14244963 | cg14395787 |
| cg14246859 | cg14398275 |
| cg14247332 | cg14399078 |
| cg14250130 | cg14399851 |
| cg14251622 | cg14400631 |
| cg14254380 | cg14402472 |
| cg14257369 | cg14404812 |
| cg14261472 | cg14405753 |
| cg14262439 | cg14406256 |
| cg14263942 | cg14406628 |
| cg14265936 | cg14409559 |
| cg14266251 | cg14412416 |
| cg14267263 | cg14415214 |
| cg14270789 | cg14415616 |

TABLE I-continued

Pan Cancer Panel

| | |
|---|---|
| cg14415885 | cg14570307 |
| cg14417372 | cg14575484 |
| cg14419581 | cg14578525 |
| cg14421860 | cg14579819 |
| cg14424049 | cg14580982 |
| cg14425722 | cg14582226 |
| cg14425863 | cg14582929 |
| cg14426525 | cg14583869 |
| cg14426781 | cg14584031 |
| cg14430974 | cg14584529 |
| cg14431699 | cg14587446 |
| cg14443380 | cg14588896 |
| cg14444140 | cg14589148 |
| cg14447369 | cg14590817 |
| cg14449803 | cg14592406 |
| cg14453704 | cg14592830 |
| cg14455998 | cg14595275 |
| cg14457918 | cg14595911 |
| cg14458834 | cg14597534 |
| cg14458955 | cg14598143 |
| cg14460343 | cg14598950 |
| cg14461650 | cg14601136 |
| cg14464464 | cg14601938 |
| cg14464509 | cg14602341 |
| cg14465900 | cg14602640 |
| cg14469376 | cg14603040 |
| cg14471619 | cg14603466 |
| cg14472025 | cg14610853 |
| cg14473522 | cg14611892 |
| cg14475915 | cg14612785 |
| cg14477452 | cg14615868 |
| cg14477745 | cg14620039 |
| cg14489346 | cg14620549 |
| cg14489594 | cg14621784 |
| cg14494448 | cg14625631 |
| cg14494623 | cg14626375 |
| cg14494933 | cg14627760 |
| cg14497202 | cg14629287 |
| cg14497673 | cg14629509 |
| cg14497851 | cg14630839 |
| cg14497940 | cg14632002 |
| cg14500250 | cg14633426 |
| cg14503180 | cg14633783 |
| cg14510404 | cg14634210 |
| cg14512363 | cg14637067 |
| cg14514226 | cg14638988 |
| cg14517108 | cg14642298 |
| cg14519123 | cg14650464 |
| cg14519153 | cg14652031 |
| cg14519294 | cg14652629 |
| cg14519850 | cg14653643 |
| cg14522427 | cg14655649 |
| cg14523810 | cg14661159 |
| cg14526204 | cg14664764 |
| cg14528318 | cg14665414 |
| cg14530233 | cg14665716 |
| cg14532412 | cg14665813 |
| cg14536899 | cg14669514 |
| cg14537243 | cg14670303 |
| cg14539978 | cg14670974 |
| cg14541950 | cg14671526 |
| cg14543508 | cg14675211 |
| cg14543941 | cg14677681 |
| cg14545970 | cg14678099 |
| cg14549262 | cg14683738 |
| cg14552376 | cg14685095 |
| cg14552401 | cg14686012 |
| cg14553600 | cg14689953 |
| cg14554167 | cg14696535 |
| cg14557534 | cg14697835 |
| cg14558428 | cg14707092 |
| cg14562083 | cg14707269 |
| cg14562158 | cg14708847 |
| cg14563868 | cg14711866 |
| cg14567287 | cg14713933 |
| cg14567414 | cg14719076 |
| cg14568217 | cg14723344 |
| cg14569471 | cg14725151 |

TABLE I-continued

Pan Cancer Panel

| | |
|---|---|
| cg14730085 | cg14950855 |
| cg14738643 | cg14953397 |
| cg14739039 | cg14955300 |
| cg14741685 | cg14960592 |
| cg14743462 | cg14962363 |
| cg14743593 | cg14970096 |
| cg14750844 | cg14971597 |
| cg14751544 | cg14975184 |
| cg14759342 | cg14978307 |
| cg14772118 | cg14980060 |
| cg14774364 | cg14982133 |
| cg14776114 | cg14984246 |
| cg14777772 | cg14985481 |
| cg14780004 | cg14986699 |
| cg14784699 | cg14986962 |
| cg14786398 | cg14987048 |
| cg14791866 | cg14988503 |
| cg14793086 | cg14989642 |
| cg14795119 | cg14990333 |
| cg14806773 | cg14992155 |
| cg14808132 | cg14992232 |
| cg14808329 | cg14993820 |
| cg14808890 | cg14995036 |
| cg14809226 | cg14997226 |
| cg14811608 | cg14998713 |
| cg14814333 | cg15007391 |
| cg14816482 | cg15012766 |
| cg14823287 | cg15014826 |
| cg14826226 | cg15019790 |
| cg14831838 | cg15020425 |
| cg14831990 | cg15024936 |
| cg14834850 | cg15034135 |
| cg14841337 | cg15038664 |
| cg14847688 | cg15042080 |
| cg14850412 | cg15042995 |
| cg14851108 | cg15044073 |
| cg14855657 | cg15048660 |
| cg14856893 | cg15051226 |
| cg14859047 | cg15052854 |
| cg14859854 | cg15057150 |
| cg14860120 | cg15057442 |
| cg14865717 | cg15061981 |
| cg14867604 | cg15063322 |
| cg14868703 | cg15063355 |
| cg14869141 | cg15068050 |
| cg14870242 | cg15069758 |
| cg14876685 | cg15071611 |
| cg14883448 | cg15071854 |
| cg14883916 | cg15075170 |
| cg14895945 | cg15077376 |
| cg14897419 | cg15078013 |
| cg14898260 | cg15088000 |
| cg14898822 | cg15088777 |
| cg14900295 | cg15089487 |
| cg14900984 | cg15089892 |
| cg14901232 | cg15090202 |
| cg14902356 | cg15091323 |
| cg14905632 | cg15097584 |
| cg14906390 | cg15097762 |
| cg14910061 | cg15099632 |
| cg14910368 | cg15100227 |
| cg14914519 | cg15104702 |
| cg14914982 | cg15111475 |
| cg14916315 | cg15112395 |
| cg14921743 | cg15112775 |
| cg14922886 | cg15118872 |
| cg14929100 | cg15119076 |
| cg14929757 | cg15119377 |
| cg14930059 | cg15123035 |
| cg14931304 | cg15123881 |
| cg14932794 | cg15124968 |
| cg14933159 | cg15127661 |
| cg14937343 | cg15128200 |
| cg14940405 | cg15129823 |
| cg14943877 | cg15131414 |
| cg14944944 | cg15131977 |
| cg14946389 | cg15133344 |
| cg14948290 | cg15134628 |

TABLE I-continued

Pan Cancer Panel

| | |
|---|---|
| cg15137760 | cg15321298 |
| cg15138883 | cg15322430 |
| cg15139482 | cg15322570 |
| cg15139588 | cg15323252 |
| cg15139745 | cg15324424 |
| cg15140191 | cg15325978 |
| cg15144236 | cg15326320 |
| cg15145693 | cg15326795 |
| cg15147435 | cg15331902 |
| cg15147690 | cg15336997 |
| cg15151685 | cg15340644 |
| cg15154191 | cg15353061 |
| cg15156614 | cg15353444 |
| cg15158376 | cg15355118 |
| cg15160780 | cg15355420 |
| cg15160843 | cg15356923 |
| cg15164958 | cg15358633 |
| cg15167155 | cg15359501 |
| cg15167646 | cg15361065 |
| cg15170424 | cg15364537 |
| cg15170743 | cg15365320 |
| cg15173150 | cg15367082 |
| cg15174311 | cg15369512 |
| cg15174834 | cg15369743 |
| cg15174951 | cg15377586 |
| cg15177071 | cg15382497 |
| cg15179113 | cg15382696 |
| cg15179725 | cg15384856 |
| cg15179955 | cg15385562 |
| cg15185001 | cg15386368 |
| cg15185479 | cg15386964 |
| cg15190738 | cg15387132 |
| cg15193782 | cg15389490 |
| cg15195321 | cg15390554 |
| cg15201536 | cg15391499 |
| cg15208756 | cg15392269 |
| cg15210108 | cg15392489 |
| cg15211499 | cg15394350 |
| cg15211655 | cg15396395 |
| cg15212349 | cg15397448 |
| cg15218775 | cg15401067 |
| cg15219650 | cg15402399 |
| cg15226147 | cg15407528 |
| cg15232894 | cg15410253 |
| cg15233183 | cg15410276 |
| cg15240568 | cg15412736 |
| cg15245095 | cg15414833 |
| cg15247645 | cg15415545 |
| cg15248577 | cg15420387 |
| cg15249639 | cg15420692 |
| cg15257259 | cg15421606 |
| cg15257376 | cg15424054 |
| cg15258033 | cg15424250 |
| cg15258847 | cg15424739 |
| cg15264083 | cg15430464 |
| cg15264811 | cg15433056 |
| cg15267010 | cg15434569 |
| cg15269503 | cg15438497 |
| cg15270697 | cg15442262 |
| cg15278646 | cg15442811 |
| cg15279950 | cg15442988 |
| cg15282018 | cg15444978 |
| cg15283062 | cg15446670 |
| cg15289427 | cg15447479 |
| cg15292101 | cg15448907 |
| cg15301489 | cg15450734 |
| cg15306209 | cg15454726 |
| cg15308062 | cg15454895 |
| cg15308664 | cg15461105 |
| cg15310637 | cg15461888 |
| cg15311382 | cg15462174 |
| cg15312298 | cg15462457 |
| cg15313226 | cg15463628 |
| cg15316583 | cg15471079 |
| cg15318396 | cg15471812 |
| cg15318690 | cg15472210 |
| cg15319517 | cg15472403 |
| cg15320948 | cg15473325 |

TABLE I-continued

Pan Cancer Panel

| | |
|---|---|
| cg15473751 | cg15646782 |
| cg15475080 | cg15648026 |
| cg15475576 | cg15651650 |
| cg15476279 | cg15653282 |
| cg15479068 | cg15658487 |
| cg15480095 | cg15664899 |
| cg15481636 | cg15672146 |
| cg15482792 | cg15674129 |
| cg15485323 | cg15679144 |
| cg15486374 | cg15684724 |
| cg15488251 | cg15684917 |
| cg15490840 | cg15685268 |
| cg15490944 | cg15685943 |
| cg15491911 | cg15689967 |
| cg15493051 | cg15692239 |
| cg15494405 | cg15692535 |
| cg15496005 | cg15698568 |
| cg15496063 | cg15699267 |
| cg15498349 | cg15700487 |
| cg15504677 | cg15704369 |
| cg15528091 | cg15705469 |
| cg15533075 | cg15710245 |
| cg15540596 | cg15713801 |
| cg15542798 | cg15717066 |
| cg15542994 | cg15717808 |
| cg15543919 | cg15718162 |
| cg15545624 | cg15722404 |
| cg15546187 | cg15724773 |
| cg15546607 | cg15726314 |
| cg15547669 | cg15732502 |
| cg15554007 | cg15734706 |
| cg15554438 | cg15736338 |
| cg15558982 | cg15736978 |
| cg15562399 | cg15737365 |
| cg15562912 | cg15739717 |
| cg15564428 | cg15745385 |
| cg15571277 | cg15745619 |
| cg15571330 | cg15748470 |
| cg15572012 | cg15748490 |
| cg15573925 | cg15757271 |
| cg15575982 | cg15758138 |
| cg15578015 | cg15759056 |
| cg15583014 | cg15759616 |
| cg15584445 | cg15770728 |
| cg15586779 | cg15773137 |
| cg15591513 | cg15774465 |
| cg15592187 | cg15777964 |
| cg15592945 | cg15778012 |
| cg15595044 | cg15786541 |
| cg15597257 | cg15787284 |
| cg15598442 | cg15792252 |
| cg15599946 | cg15799279 |
| cg15601228 | cg15804105 |
| cg15603957 | cg15804767 |
| cg15611279 | cg15808558 |
| cg15612063 | cg15809694 |
| cg15612845 | cg15811719 |
| cg15615350 | cg15819171 |
| cg15616946 | cg15820273 |
| cg15617019 | cg15822346 |
| cg15617847 | cg15824316 |
| cg15620146 | cg15825116 |
| cg15620384 | cg15825186 |
| cg15621338 | cg15830431 |
| cg15622672 | cg15837382 |
| cg15623249 | cg15840419 |
| cg15623480 | cg15842116 |
| cg15623503 | cg15843401 |
| cg15623573 | cg15846316 |
| cg15627078 | cg15846643 |
| cg15628498 | cg15847198 |
| cg15631323 | cg15847614 |
| cg15632325 | cg15852572 |
| cg15637095 | cg15860695 |
| cg15642792 | cg15863148 |
| cg15643885 | cg15863924 |
| cg15645220 | cg15864491 |
| cg15645634 | cg15869383 |

TABLE I-continued

Pan Cancer Panel cg15871647
cg15873303
cg15875437
cg15879316
cg15879949
cg15885628
cg15889017
cg15889804
cg15890274
cg15891422
cg15892839
cg15893070
cg15896339
cg15897970
cg15900320
cg15900657
cg15904764
cg15906409
cg15907310
cg15909933
cg15910486
cg15914011
cg15914589
cg15915129
cg15916166
cg15916192
cg15917116
cg15919045
cg15919396
cg15920867
cg15921240
cg15924577
cg15924985
cg15925383
cg15928538
cg15929693
cg15931721
cg15933823
cg15934415
cg15934994
cg15939253
cg15940724
cg15942481
cg15946212
cg15946251
cg15946259
cg15947940
cg15955291
cg15955731
cg15958576
cg15963563
cg15965542
cg15966876
cg15968604
cg15969216
cg15971888
cg15974272
cg15976650
cg15977719
cg15978014
cg15981995
cg15987088
cg15991262
cg15991471
cg15996043
cg15996499
cg15999899
cg16005828
cg16005847
cg16006242
cg16007619
cg16008609
cg16008616
cg16011583
cg16011800
cg16012041
cg16012111
cg16014770

TABLE I-continued

Pan Cancer Panel cg16016176
cg16019856
cg16019898
cg16021775
cg16024834
cg16026627
cg16030427
cg16034881
cg16040495
cg16040504
cg16048372
cg16048568
cg16049364
cg16049707
cg16056105
cg16056849
cg16057262
cg16060486
cg16061012
cg16063519
cg16064478
cg16068063
cg16070123
cg16079396
cg16079958
cg16080450
cg16082336
cg16083800
cg16088123
cg16093752
cg16094298
cg16095615
cg16095951
cg16096796
cg16098064
cg16101148
cg16110940
cg16112844
cg16113298
cg16114640
cg16117248
cg16117910
cg16126280
cg16127719
cg16128701
cg16129172
cg16132520
cg16134800
cg16136098
cg16139934
cg16140432
cg16141316
cg16144193
cg16146177
cg16149238
cg16150677
cg16154689
cg16159491
cg16162324
cg16162668
cg16169604
cg16172313
cg16172408
cg16172657
cg16173736
cg16174274
cg16176048
cg16176568
cg16178625
cg16179047
cg16180217
cg16181043
cg16185831
cg16187092
cg16189024
cg16189346
cg16190350
cg16195569

TABLE I-continued

Pan Cancer Panel cg16196984
cg16200496
cg16203801
cg16208507
cg16216704
cg16219491
cg16219810
cg16226745
cg16229376
cg16230141
cg16232979
cg16234029
cg16235861
cg16236766
cg16238795
cg16246366
cg16246961
cg16248783
cg16250330
cg16250461
cg16253259
cg16254764
cg16257681
cg16263224
cg16266453
cg16267579
cg16268214
cg16268778
cg16268848
cg16271017
cg16274199
cg16275739
cg16276070
cg16276153
cg16277128
cg16285203
cg16285380
cg16288248
cg16291962
cg16292168
cg16293631
cg16296290
cg16296826
cg16297938
cg16300317
cg16306190
cg16307409
cg16313278
cg16315928
cg16317459
cg16318768
cg16319691
cg16321523
cg16328251
cg16329784
cg16330517
cg16331920
cg16334629
cg16335926
cg16339096
cg16347317
cg16351364
cg16354201
cg16354296
cg16358446
cg16359169
cg16365799
cg16366473
cg16368442
cg16370586
cg16372625
cg16373769
cg16374471
cg16375948
cg16379337
cg16382256
cg16384885
cg16391783

TABLE I-continued

Pan Cancer Panel cg16395486
cg16403669
cg16404460
cg16405637
cg16406225
cg16406833
cg16409838
cg16409840
cg16410706
cg16416045
cg16417447
cg16418684
cg16419066
cg16423505
cg16424178
cg16424326
cg16426482
cg16430510
cg16430572
cg16430909
cg16433211
cg16434547
cg16438397
cg16440629
cg16443424
cg16443970
cg16446408
cg16447652
cg16452086
cg16458671
cg16460359
cg16466899
cg16469099
cg16470309
cg16471850
cg16473511
cg16475705
cg16475755
cg16478774
cg16480132
cg16487794
cg16489895
cg16492707
cg16494477
cg16496687
cg16496895
cg16497277
cg16503618
cg16504335
cg16506703
cg16508199
cg16512570
cg16515523
cg16519173
cg16521245
cg16522462
cg16523137
cg16524830
cg16531271
cg16532600
cg16532755
cg16533373
cg16533495
cg16534233
cg16534499
cg16535332
cg16537756
cg16538178
cg16541852
cg16544887
cg16545496
cg16546016
cg16547110
cg16549389
cg16551483
cg16557944
cg16558908
cg16564710

TABLE I-continued

Pan Cancer Panel

| | |
|---|---|
| cg16564802 | cg16703914 |
| cg16564842 | cg16704678 |
| cg16568036 | cg16704739 |
| cg16570019 | cg16704802 |
| cg16573136 | cg16705351 |
| cg16573178 | cg16705383 |
| cg16573328 | cg16705665 |
| cg16573542 | cg16707062 |
| cg16576620 | cg16712637 |
| cg16577002 | cg16713262 |
| cg16579555 | cg16715162 |
| cg16580934 | cg16717099 |
| cg16583330 | cg16718445 |
| cg16584595 | cg16718942 |
| cg16585911 | cg16718986 |
| cg16586442 | cg16728223 |
| cg16588061 | cg16729160 |
| cg16589663 | cg16732469 |
| cg16590005 | cg16733654 |
| cg16595261 | cg16733855 |
| cg16596102 | cg16740476 |
| cg16600119 | cg16740905 |
| cg16601893 | cg16741308 |
| cg16602799 | cg16743811 |
| cg16611581 | cg16749570 |
| cg16612379 | cg16750914 |
| cg16612742 | cg16751623 |
| cg16619071 | cg16751732 |
| cg16622511 | cg16753409 |
| cg16624692 | cg16754678 |
| cg16624787 | cg16758662 |
| cg16627646 | cg16761549 |
| cg16628372 | cg16762077 |
| cg16630791 | cg16763192 |
| cg16632280 | cg16764580 |
| cg16633750 | cg16765006 |
| cg16633901 | cg16768441 |
| cg16638266 | cg16772035 |
| cg16641818 | cg16776231 |
| cg16644177 | cg16777057 |
| cg16645133 | cg16780890 |
| cg16652651 | cg16782935 |
| cg16652790 | cg16785690 |
| cg16654143 | cg16790239 |
| cg16654152 | cg16796590 |
| cg16654732 | cg16797300 |
| cg16655084 | cg16797714 |
| cg16655338 | cg16800028 |
| cg16655805 | cg16800708 |
| cg16655905 | cg16800851 |
| cg16658099 | cg16801093 |
| cg16658130 | cg16801720 |
| cg16658719 | cg16802027 |
| cg16661554 | cg16802151 |
| cg16662989 | cg16803141 |
| cg16663344 | cg16805065 |
| cg16663570 | cg16805150 |
| cg16663900 | cg16813053 |
| cg16672925 | cg16814399 |
| cg16673106 | cg16817229 |
| cg16675644 | cg16818909 |
| cg16675700 | cg16818993 |
| cg16675708 | cg16821694 |
| cg16678602 | cg16822189 |
| cg16682989 | cg16822216 |
| cg16689800 | cg16822474 |
| cg16691033 | cg16832551 |
| cg16692923 | cg16836995 |
| cg16692998 | cg16838838 |
| cg16693872 | cg16844403 |
| cg16696021 | cg16844989 |
| cg16696536 | cg16848054 |
| cg16696645 | cg16848116 |
| cg16697731 | cg16848624 |
| cg16698835 | cg16853034 |
| cg16699174 | cg16858615 |
| cg16699861 | cg16859924 |
| cg16703576 | cg16862295 |

TABLE I-continued

Pan Cancer Panel

| | |
|---|---|
| cg16862624 | cg17078980 |
| cg16863718 | cg17081644 |
| cg16863990 | cg17081778 |
| cg16868994 | cg17088631 |
| cg16871994 | cg17091793 |
| cg16874579 | cg17092624 |
| cg16876647 | cg17093212 |
| cg16879222 | cg17093995 |
| cg16882226 | cg17094378 |
| cg16883282 | cg17097950 |
| cg16884042 | cg17100218 |
| cg16884569 | cg17100322 |
| cg16885107 | cg17105013 |
| cg16885296 | cg17106175 |
| cg16887890 | cg17106222 |
| cg16891895 | cg17107459 |
| cg16895792 | cg17108748 |
| cg16897885 | cg17114257 |
| cg16899280 | cg17125477 |
| cg16899486 | cg17127587 |
| cg16903605 | cg17128349 |
| cg16906712 | cg17128996 |
| cg16909109 | cg17130063 |
| cg16914151 | cg17131030 |
| cg16914989 | cg17136126 |
| cg16919771 | cg17142743 |
| cg16921310 | cg17143192 |
| cg16922058 | cg17145587 |
| cg16925307 | cg17146291 |
| cg16927253 | cg17146640 |
| cg16934685 | cg17147995 |
| cg16936581 | cg17150306 |
| cg16938614 | cg17152789 |
| cg16944092 | cg17152869 |
| cg16953473 | cg17154605 |
| cg16958716 | cg17155612 |
| cg16962970 | cg17159473 |
| cg16963683 | cg17161743 |
| cg16966815 | cg17164747 |
| cg16967640 | cg17167076 |
| cg16968865 | cg17169289 |
| cg16970851 | cg17169566 |
| cg16974909 | cg17170568 |
| cg16977570 | cg17171962 |
| cg16978797 | cg17174375 |
| cg16983817 | cg17177755 |
| cg16984332 | cg17178280 |
| cg16991768 | cg17182507 |
| cg16994506 | cg17183414 |
| cg16995983 | cg17185401 |
| cg16998537 | cg17186727 |
| cg17003293 | cg17188147 |
| cg17009433 | cg17188901 |
| cg17014953 | cg17191919 |
| cg17015511 | cg17192115 |
| cg17016932 | cg17194182 |
| cg17018527 | cg17198587 |
| cg17022437 | cg17200447 |
| cg17023776 | cg17204213 |
| cg17025142 | cg17204394 |
| cg17026879 | cg17205316 |
| cg17027195 | cg17210604 |
| cg17031478 | cg17215449 |
| cg17034030 | cg17217189 |
| cg17035091 | cg17218628 |
| cg17036833 | cg17222234 |
| cg17042926 | cg17225222 |
| cg17043284 | cg17234305 |
| cg17045804 | cg17241016 |
| cg17046890 | cg17243637 |
| cg17049889 | cg17245188 |
| cg17052813 | cg17246382 |
| cg17052926 | cg17250302 |
| cg17057514 | cg17251034 |
| cg17059853 | cg17252605 |
| cg17061505 | cg17255947 |
| cg17068985 | cg17259656 |
| cg17070611 | cg17268276 |

TABLE I-continued

Pan Cancer Panel

| | |
|---|---|
| cg17269277 | cg17456266 |
| cg17270520 | cg17459431 |
| cg17271180 | cg17460095 |
| cg17277729 | cg17465133 |
| cg17277949 | cg17468312 |
| cg17278573 | cg17468987 |
| cg17279338 | cg17470837 |
| cg17283601 | cg17473382 |
| cg17284384 | cg17482197 |
| cg17285325 | cg17483297 |
| cg17287725 | cg17485454 |
| cg17287767 | cg17491947 |
| cg17290076 | cg17494781 |
| cg17291435 | cg17498803 |
| cg17291521 | cg17500103 |
| cg17293641 | cg17500189 |
| cg17296166 | cg17507573 |
| cg17298489 | cg17509349 |
| cg17299935 | cg17512353 |
| cg17304222 | cg17515747 |
| cg17304496 | cg17517900 |
| cg17306638 | cg17521338 |
| cg17318632 | cg17522907 |
| cg17318990 | cg17526300 |
| cg17321214 | cg17526812 |
| cg17323027 | cg17527574 |
| cg17323409 | cg17528648 |
| cg17325959 | cg17530977 |
| cg17327184 | cg17532976 |
| cg17327401 | cg17533458 |
| cg17328790 | cg17534770 |
| cg17329249 | cg17536603 |
| cg17332338 | cg17546469 |
| cg17334978 | cg17549121 |
| cg17345188 | cg17557106 |
| cg17345480 | cg17558973 |
| cg17346177 | cg17560327 |
| cg17352157 | cg17564074 |
| cg17354190 | cg17573068 |
| cg17354785 | cg17575811 |
| cg17355083 | cg17584804 |
| cg17355294 | cg17585197 |
| cg17356181 | cg17585343 |
| cg17360650 | cg17587023 |
| cg17372745 | cg17589079 |
| cg17376957 | cg17592734 |
| cg17379799 | cg17599471 |
| cg17383940 | cg17607368 |
| cg17384056 | cg17615007 |
| cg17384898 | cg17617527 |
| cg17387989 | cg17618595 |
| cg17398233 | cg17619993 |
| cg17399352 | cg17620121 |
| cg17404915 | cg17621259 |
| cg17406148 | cg17625506 |
| cg17411913 | cg17640322 |
| cg17412258 | cg17641046 |
| cg17412602 | cg17651693 |
| cg17416280 | cg17651973 |
| cg17417193 | cg17652435 |
| cg17418463 | cg17655978 |
| cg17419241 | cg17656165 |
| cg17420983 | cg17660078 |
| cg17428043 | cg17666096 |
| cg17428324 | cg17671608 |
| cg17431401 | cg17676607 |
| cg17432022 | cg17679608 |
| cg17432453 | cg17679781 |
| cg17432620 | cg17683390 |
| cg17434043 | cg17684296 |
| cg17435266 | cg17687528 |
| cg17438432 | cg17689925 |
| cg17439093 | cg17690832 |
| cg17441778 | cg17691292 |
| cg17442482 | cg17691309 |
| cg17445007 | cg17699947 |
| cg17445044 | cg17703990 |
| cg17445120 | cg17705658 |

TABLE I-continued

Pan Cancer Panel

| | |
|---|---|
| cg17707984 | cg17887593 |
| cg17708016 | cg17887993 |
| cg17710868 | cg17888837 |
| cg17712828 | cg17891194 |
| cg17715556 | cg17893474 |
| cg17716617 | cg17896129 |
| cg17718302 | cg17902573 |
| cg17718457 | cg17903544 |
| cg17727989 | cg17904852 |
| cg17728851 | cg17905084 |
| cg17730484 | cg17909311 |
| cg17731261 | cg17910679 |
| cg17735983 | cg17910969 |
| cg17737146 | cg17913259 |
| cg17739038 | cg17927777 |
| cg17745088 | cg17929997 |
| cg17748329 | cg17930878 |
| cg17752015 | cg17935875 |
| cg17755907 | cg17940251 |
| cg17755923 | cg17942925 |
| cg17759086 | cg17945419 |
| cg17764507 | cg17947546 |
| cg17764989 | cg17953520 |
| cg17765304 | cg17957827 |
| cg17767542 | cg17958384 |
| cg17767945 | cg17958423 |
| cg17769463 | cg17960051 |
| cg17771515 | cg17967970 |
| cg17773020 | cg17971531 |
| cg17773349 | cg17972708 |
| cg17773763 | cg17975002 |
| cg17774347 | cg17976576 |
| cg17777708 | cg17978562 |
| cg17778441 | cg17984375 |
| cg17779790 | cg17985124 |
| cg17780956 | cg17990532 |
| cg17783982 | cg17990771 |
| cg17784528 | cg17995867 |
| cg17793527 | cg17996329 |
| cg17799295 | cg17997310 |
| cg17800473 | cg18003214 |
| cg17805404 | cg18003762 |
| cg17807528 | cg18007850 |
| cg17808823 | cg18022777 |
| cg17815252 | cg18023401 |
| cg17820890 | cg18028711 |
| cg17824240 | cg18029521 |
| cg17825384 | cg18032744 |
| cg17826375 | cg18035537 |
| cg17829673 | cg18040241 |
| cg17831137 | cg18042229 |
| cg17838029 | cg18043078 |
| cg17838765 | cg18044385 |
| cg17839008 | cg18049676 |
| cg17839237 | cg18050543 |
| cg17839259 | cg18051461 |
| cg17839314 | cg18058532 |
| cg17839359 | cg18058994 |
| cg17840061 | cg18064474 |
| cg17846785 | cg18064852 |
| cg17849956 | cg18066271 |
| cg17853504 | cg18068240 |
| cg17853707 | cg18070061 |
| cg17860381 | cg18071006 |
| cg17861551 | cg18071147 |
| cg17864044 | cg18072629 |
| cg17870408 | cg18073970 |
| cg17871739 | cg18077391 |
| cg17874478 | cg18078305 |
| cg17876581 | cg18078387 |
| cg17880199 | cg18085998 |
| cg17880859 | cg18088494 |
| cg17881660 | cg18088653 |
| cg17883067 | cg18096253 |
| cg17885062 | cg18100007 |
| cg17885806 | cg18108008 |
| cg17886028 | cg18108362 |
| cg17887537 | cg18109777 |

TABLE I-continued

Pan Cancer Panel

| | |
|---|---|
| cg18110535 | cg18287975 |
| cg18111139 | cg18293833 |
| cg18113107 | cg18300848 |
| cg18113780 | cg18304472 |
| cg18113994 | cg18304969 |
| cg18114235 | cg18308176 |
| cg18117228 | cg18310412 |
| cg18121355 | cg18312997 |
| cg18123319 | cg18315695 |
| cg18125479 | cg18319921 |
| cg18125549 | cg18320379 |
| cg18127204 | cg18323466 |
| cg18132916 | cg18324126 |
| cg18137427 | cg18325992 |
| cg18137931 | cg18326610 |
| cg18138147 | cg18326657 |
| cg18139020 | cg18328206 |
| cg18139254 | cg18329349 |
| cg18140683 | cg18331004 |
| cg18142615 | cg18333921 |
| cg18143243 | cg18335176 |
| cg18144285 | cg18335243 |
| cg18144296 | cg18344922 |
| cg18146873 | cg18345826 |
| cg18147366 | cg18349835 |
| cg18149653 | cg18354742 |
| cg18149689 | cg18354948 |
| cg18152871 | cg18357526 |
| cg18153124 | cg18357908 |
| cg18156793 | cg18362509 |
| cg18159850 | cg18371506 |
| cg18161100 | cg18373944 |
| cg18167179 | cg18375586 |
| cg18169128 | cg18379780 |
| cg18169385 | cg18382422 |
| cg18172823 | cg18384926 |
| cg18175036 | cg18387399 |
| cg18175880 | cg18387516 |
| cg18176922 | cg18388891 |
| cg18180107 | cg18390181 |
| cg18181323 | cg18395675 |
| cg18182358 | cg18399321 |
| cg18190030 | cg18403606 |
| cg18191418 | cg18411103 |
| cg18194354 | cg18411550 |
| cg18195080 | cg18411800 |
| cg18200760 | cg18413587 |
| cg18202861 | cg18414618 |
| cg18206459 | cg18415585 |
| cg18209835 | cg18416022 |
| cg18217145 | cg18416881 |
| cg18219563 | cg18418651 |
| cg18221467 | cg18419164 |
| cg18223947 | cg18420512 |
| cg18228326 | cg18424064 |
| cg18233405 | cg18424968 |
| cg18233416 | cg18425877 |
| cg18234709 | cg18427336 |
| cg18235026 | cg18428373 |
| cg18235573 | cg18429863 |
| cg18236665 | cg18430156 |
| cg18239372 | cg18430208 |
| cg18240143 | cg18434848 |
| cg18244289 | cg18438124 |
| cg18244915 | cg18438546 |
| cg18245460 | cg18440316 |
| cg18245660 | cg18440902 |
| cg18245890 | cg18442587 |
| cg18248022 | cg18443378 |
| cg18249625 | cg18444347 |
| cg18251612 | cg18449734 |
| cg18252360 | cg18449997 |
| cg18253802 | cg18451274 |
| cg18254147 | cg18453621 |
| cg18274325 | cg18461950 |
| cg18277508 | cg18463001 |
| cg18279751 | cg18465515 |
| cg18285309 | cg18466674 |

TABLE I-continued

Pan Cancer Panel

| | |
|---|---|
| cg18466859 | cg18652367 |
| cg18468394 | cg18654377 |
| cg18470710 | cg18655441 |
| cg18473090 | cg18655782 |
| cg18473652 | cg18658397 |
| cg18476049 | cg18669346 |
| cg18481137 | cg18670721 |
| cg18483529 | cg18671997 |
| cg18484034 | cg18676082 |
| cg18484166 | cg18676237 |
| cg18488430 | cg18680346 |
| cg18492647 | cg18682423 |
| cg18493027 | cg18689666 |
| cg18495307 | cg18696692 |
| cg18497550 | cg18697982 |
| cg18499667 | cg18702108 |
| cg18499839 | cg18703913 |
| cg18503381 | cg18704768 |
| cg18504015 | cg18705240 |
| cg18511445 | cg18711394 |
| cg18512156 | cg18713809 |
| cg18513970 | cg18714498 |
| cg18522413 | cg18721673 |
| cg18522518 | cg18729886 |
| cg18524952 | cg18744458 |
| cg18527133 | cg18746451 |
| cg18528082 | cg18750086 |
| cg18530075 | cg18750167 |
| cg18530251 | cg18750433 |
| cg18532190 | cg18751588 |
| cg18532727 | cg18753811 |
| cg18533833 | cg18754389 |
| cg18534992 | cg18759693 |
| cg18542177 | cg18760621 |
| cg18542829 | cg18760835 |
| cg18542992 | cg18762243 |
| cg18547611 | cg18762485 |
| cg18555069 | cg18762849 |
| cg18556179 | cg18763720 |
| cg18560502 | cg18764015 |
| cg18562663 | cg18764513 |
| cg18562689 | cg18768453 |
| cg18563326 | cg18775012 |
| cg18564099 | cg18782736 |
| cg18564808 | cg18784420 |
| cg18565473 | cg18786479 |
| cg18567992 | cg18787914 |
| cg18568653 | cg18789841 |
| cg18575209 | cg18791121 |
| cg18575770 | cg18795395 |
| cg18576158 | cg18795469 |
| cg18577280 | cg18796531 |
| cg18583563 | cg18798248 |
| cg18584747 | cg18798264 |
| cg18585722 | cg18798750 |
| cg18586470 | cg18798922 |
| cg18586919 | cg18798995 |
| cg18588052 | cg18799048 |
| cg18592273 | cg18800161 |
| cg18602314 | cg18800479 |
| cg18603154 | cg18801599 |
| cg18607529 | cg18809855 |
| cg18608369 | cg18810347 |
| cg18608389 | cg18811597 |
| cg18610423 | cg18812668 |
| cg18610889 | cg18812980 |
| cg18616418 | cg18813353 |
| cg18619591 | cg18815779 |
| cg18621091 | cg18818834 |
| cg18624348 | cg18821633 |
| cg18634060 | cg18828883 |
| cg18637244 | cg18832632 |
| cg18639180 | cg18833573 |
| cg18642499 | cg18834712 |
| cg18643445 | cg18839746 |
| cg18647881 | cg18845832 |
| cg18649745 | cg18846140 |
| cg18649939 | cg18846362 |

TABLE I-continued

Pan Cancer Panel

| | |
|---|---|
| cg18849621 | cg19070841 |
| cg18849840 | cg19075346 |
| cg18851831 | cg19079546 |
| cg18852765 | cg19081437 |
| cg18853935 | cg19083459 |
| cg18855836 | cg19083779 |
| cg18859763 | cg19083871 |
| cg18867659 | cg19085463 |
| cg18867902 | cg19089073 |
| cg18870712 | cg19089314 |
| cg18873530 | cg19089337 |
| cg18875716 | cg19096424 |
| cg18876786 | cg19099850 |
| cg18877969 | cg19109608 |
| cg18879160 | cg19110523 |
| cg18881873 | cg19113326 |
| cg18882060 | cg19113641 |
| cg18884940 | cg19115805 |
| cg18894054 | cg19116006 |
| cg18900649 | cg19116429 |
| cg18901116 | cg19117365 |
| cg18902978 | cg19118212 |
| cg18904891 | cg19118812 |
| cg18909973 | cg19121462 |
| cg18911592 | cg19132762 |
| cg18923197 | cg19135230 |
| cg18925548 | cg19135706 |
| cg18925923 | cg19141563 |
| cg18932809 | cg19148866 |
| cg18934496 | cg19157162 |
| cg18935660 | cg19157243 |
| cg18938674 | cg19162106 |
| cg18940113 | cg19165854 |
| cg18940588 | cg19170589 |
| cg18943599 | cg19174706 |
| cg18946117 | cg19176453 |
| cg18946478 | cg19177465 |
| cg18948743 | cg19177783 |
| cg18950617 | cg19181244 |
| cg18956706 | cg19184963 |
| cg18958684 | cg19187185 |
| cg18960642 | cg19190217 |
| cg18961230 | cg19191454 |
| cg18964732 | cg19191500 |
| cg18985581 | cg19201719 |
| cg18993701 | cg19202687 |
| cg18996590 | cg19208331 |
| cg19001794 | cg19214222 |
| cg19006060 | cg19216563 |
| cg19008809 | cg19217692 |
| cg19009323 | cg19219577 |
| cg19013262 | cg19221959 |
| cg19015909 | cg19226872 |
| cg19016289 | cg19229344 |
| cg19019371 | cg19233518 |
| cg19021328 | cg19235095 |
| cg19021466 | cg19238531 |
| cg19022827 | cg19239848 |
| cg19026207 | cg19245371 |
| cg19027571 | cg19246266 |
| cg19027852 | cg19247228 |
| cg19029747 | cg19247350 |
| cg19033035 | cg19248242 |
| cg19036153 | cg19250101 |
| cg19037327 | cg19257356 |
| cg19037480 | cg19263700 |
| cg19038690 | cg19267325 |
| cg19040026 | cg19267760 |
| cg19040163 | cg19268498 |
| cg19040667 | cg19274837 |
| cg19041648 | cg19275050 |
| cg19042950 | cg19282714 |
| cg19047942 | cg19285217 |
| cg19053664 | cg19287220 |
| cg19055936 | cg19287277 |
| cg19058495 | cg19287823 |
| cg19067897 | cg19289599 |
| cg19068071 | cg19294653 |

TABLE I-continued

Pan Cancer Panel

| | |
|---|---|
| cg19301658 | cg19511590 |
| cg19302722 | cg19511664 |
| cg19302831 | cg19512521 |
| cg19304410 | cg19515317 |
| cg19306047 | cg19523118 |
| cg19306496 | cg19523213 |
| cg19313015 | cg19523287 |
| cg19314945 | cg19526626 |
| cg19317413 | cg19529326 |
| cg19317517 | cg19530176 |
| cg19318095 | cg19530551 |
| cg19320275 | cg19532257 |
| cg19320564 | cg19533530 |
| cg19320816 | cg19534879 |
| cg19321991 | cg19536404 |
| cg19323374 | cg19538890 |
| cg19326622 | cg19539421 |
| cg19335954 | cg19540689 |
| cg19342109 | cg19540702 |
| cg19348622 | cg19544459 |
| cg19354750 | cg19546232 |
| cg19355186 | cg19551232 |
| cg19356117 | cg19554555 |
| cg19358349 | cg19557340 |
| cg19359398 | cg19557518 |
| cg19360562 | cg19557537 |
| cg19363466 | cg19559519 |
| cg19365062 | cg19564877 |
| cg19367540 | cg19570171 |
| cg19370980 | cg19571046 |
| cg19375296 | cg19580847 |
| cg19376090 | cg19584530 |
| cg19378602 | cg19586132 |
| cg19381368 | cg19587654 |
| cg19381780 | cg19589919 |
| cg19382545 | cg19590063 |
| cg19396601 | cg19590834 |
| cg19397703 | cg19592942 |
| cg19399402 | cg19594156 |
| cg19410738 | cg19594691 |
| cg19416050 | cg19595107 |
| cg19423014 | cg19595234 |
| cg19427757 | cg19595835 |
| cg19429323 | cg19596204 |
| cg19429466 | cg19597776 |
| cg19430897 | cg19600750 |
| cg19431241 | cg19603847 |
| cg19431448 | cg19605258 |
| cg19435033 | cg19610370 |
| cg19435381 | cg19611175 |
| cg19439810 | cg19611817 |
| cg19442495 | cg19613400 |
| cg19444950 | cg19614698 |
| cg19445996 | cg19618483 |
| cg19446018 | cg19621580 |
| cg19446838 | cg19623237 |
| cg19450036 | cg19625088 |
| cg19450714 | cg19628038 |
| cg19452853 | cg19630440 |
| cg19452953 | cg19631064 |
| cg19455142 | cg19634213 |
| cg19458485 | cg19635869 |
| cg19461392 | cg19636656 |
| cg19470159 | cg19639530 |
| cg19484319 | cg19639622 |
| cg19486482 | cg19641582 |
| cg19488260 | cg19643211 |
| cg19491151 | cg19645410 |
| cg19494762 | cg19646327 |
| cg19499754 | cg19649564 |
| cg19504308 | cg19649746 |
| cg19507527 | cg19650197 |
| cg19508191 | cg19651223 |
| cg19508683 | cg19653161 |
| cg19509715 | cg19654209 |
| cg19509763 | cg19657814 |
| cg19510038 | cg19659987 |
| cg19510792 | cg19660063 |

TABLE I-continued

Pan Cancer Panel

| | |
|---|---|
| cg19660239 | cg19844581 |
| cg19666937 | cg19847643 |
| cg19670870 | cg19850348 |
| cg19670923 | cg19850565 |
| cg19671026 | cg19851242 |
| cg19672497 | cg19851715 |
| cg19674065 | cg19853229 |
| cg19675664 | cg19853516 |
| cg19677203 | cg19853927 |
| cg19677522 | cg19856145 |
| cg19684323 | cg19859515 |
| cg19688887 | cg19863210 |
| cg19690766 | cg19863319 |
| cg19694978 | cg19864007 |
| cg19698348 | cg19868007 |
| cg19704348 | cg19871631 |
| cg19710444 | cg19875368 |
| cg19712965 | cg19876775 |
| cg19714957 | cg19877419 |
| cg19716887 | cg19878516 |
| cg19717235 | cg19884345 |
| cg19719133 | cg19891817 |
| cg19719311 | cg19891951 |
| cg19721115 | cg19894747 |
| cg19722720 | cg19895124 |
| cg19732605 | cg19895492 |
| cg19734015 | cg19896612 |
| cg19734255 | cg19899882 |
| cg19734779 | cg19907326 |
| cg19737664 | cg19908534 |
| cg19737972 | cg19908577 |
| cg19741704 | cg19909712 |
| cg19741945 | cg19910201 |
| cg19742538 | cg19910780 |
| cg19746861 | cg19913430 |
| cg19752094 | cg19913934 |
| cg19752627 | cg19918005 |
| cg19753230 | cg19918758 |
| cg19753526 | cg19923798 |
| cg19753794 | cg19925054 |
| cg19754190 | cg19926395 |
| cg19758151 | cg19927510 |
| cg19760323 | cg19929189 |
| cg19761115 | cg19932227 |
| cg19763319 | cg19934709 |
| cg19763809 | cg19936032 |
| cg19767215 | cg19936436 |
| cg19769164 | cg19936912 |
| cg19769850 | cg19939262 |
| cg19769920 | cg19940065 |
| cg19774315 | cg19950090 |
| cg19776201 | cg19950455 |
| cg19777105 | cg19956166 |
| cg19777900 | cg19956712 |
| cg19778944 | cg19958866 |
| cg19779670 | cg19962565 |
| cg19781248 | cg19963768 |
| cg19784910 | cg19967492 |
| cg19788429 | cg19967800 |
| cg19788600 | cg19969873 |
| cg19789653 | cg19974445 |
| cg19790568 | cg19975936 |
| cg19791003 | cg19977494 |
| cg19791395 | cg19978209 |
| cg19792316 | cg19981263 |
| cg19793697 | cg19984781 |
| cg19799744 | cg19987611 |
| cg19802241 | cg19990182 |
| cg19805311 | cg19993316 |
| cg19806750 | cg20006924 |
| cg19814400 | cg20009641 |
| cg19816938 | cg20010012 |
| cg19821582 | cg20012008 |
| cg19830192 | cg20018912 |
| cg19835478 | cg20019019 |
| cg19839347 | cg20022589 |
| cg19840484 | cg20023354 |
| cg19841276 | cg20024192 |

TABLE I-continued

Pan Cancer Panel

| | |
|---|---|
| cg20028058 | cg20234947 |
| cg20028291 | cg20235051 |
| cg20034091 | cg20237707 |
| cg20038789 | cg20239740 |
| cg20039407 | cg20251161 |
| cg20041567 | cg20252022 |
| cg20043291 | cg20254725 |
| cg20043969 | cg20259398 |
| cg20046964 | cg20259674 |
| cg20047732 | cg20263839 |
| cg20048050 | cg20267521 |
| cg20052718 | cg20267922 |
| cg20053454 | cg20275132 |
| cg20055841 | cg20276585 |
| cg20062650 | cg20279673 |
| cg20064106 | cg20280350 |
| cg20065569 | cg20283582 |
| cg20074142 | cg20284440 |
| cg20077155 | cg20285514 |
| cg20078119 | cg20289609 |
| cg20078466 | cg20291779 |
| cg20079899 | cg20294320 |
| cg20089538 | cg20296001 |
| cg20090551 | cg20296461 |
| cg20090558 | cg20298895 |
| cg20092102 | cg20303232 |
| cg20094085 | cg20309565 |
| cg20094282 | cg20312821 |
| cg20094610 | cg20319091 |
| cg20097650 | cg20324884 |
| cg20098332 | cg20329084 |
| cg20102397 | cg20331595 |
| cg20103107 | cg20334252 |
| cg20110591 | cg20337021 |
| cg20111643 | cg20338300 |
| cg20111875 | cg20341942 |
| cg20113619 | cg20342628 |
| cg20115051 | cg20344434 |
| cg20120070 | cg20346165 |
| cg20122470 | cg20353070 |
| cg20123891 | cg20353465 |
| cg20126635 | cg20353496 |
| cg20126980 | cg20354430 |
| cg20129313 | cg20360212 |
| cg20134241 | cg20361600 |
| cg20136584 | cg20363904 |
| cg20137045 | cg20364024 |
| cg20138711 | cg20366601 |
| cg20140398 | cg20367329 |
| cg20145610 | cg20367852 |
| cg20145692 | cg20369763 |
| cg20147819 | cg20375220 |
| cg20156450 | cg20382233 |
| cg20163166 | cg20383078 |
| cg20164253 | cg20387387 |
| cg20166532 | cg20390702 |
| cg20170831 | cg20391764 |
| cg20172280 | cg20392240 |
| cg20173072 | cg20392585 |
| cg20174277 | cg20402000 |
| cg20176285 | cg20402552 |
| cg20187670 | cg20405584 |
| cg20188733 | cg20406635 |
| cg20194811 | cg20410810 |
| cg20196129 | cg20413471 |
| cg20199629 | cg20414262 |
| cg20200385 | cg20414996 |
| cg20200553 | cg20419623 |
| cg20209956 | cg20421191 |
| cg20211422 | cg20430063 |
| cg20213228 | cg20432589 |
| cg20214853 | cg20439288 |
| cg20215622 | cg20445950 |
| cg20216802 | cg20450979 |
| cg20220436 | cg20452212 |
| cg20224751 | cg20459111 |
| cg20227255 | cg20463033 |
| cg20227976 | cg20463862 |

TABLE I-continued

Pan Cancer Panel

| | |
|---|---|
| cg20465143 | cg20650802 |
| cg20466166 | cg20651988 |
| cg20467502 | cg20655405 |
| cg20468063 | cg20656261 |
| cg20473379 | cg20660627 |
| cg20473895 | cg20661176 |
| cg20474370 | cg20662616 |
| cg20475917 | cg20665459 |
| cg20480233 | cg20666492 |
| cg20486897 | cg20675505 |
| cg20489541 | cg20678442 |
| cg20492121 | cg20679955 |
| cg20492951 | cg20680592 |
| cg20499861 | cg20680754 |
| cg20500237 | cg20681578 |
| cg20500248 | cg20693580 |
| cg20502003 | cg20696478 |
| cg20506550 | cg20696912 |
| cg20509675 | cg20696985 |
| cg20516472 | cg20699497 |
| cg20521527 | cg20702935 |
| cg20522401 | cg20710842 |
| cg20523393 | cg20716311 |
| cg20524425 | cg20717205 |
| cg20526672 | cg20718214 |
| cg20528183 | cg20718350 |
| cg20529489 | cg20718643 |
| cg20530585 | cg20718724 |
| cg20531392 | cg20718727 |
| cg20531781 | cg20718816 |
| cg20534596 | cg20725157 |
| cg20536263 | cg20735365 |
| cg20536512 | cg20736997 |
| cg20536716 | cg20738807 |
| cg20537507 | cg20743280 |
| cg20538314 | cg20749730 |
| cg20540942 | cg20749916 |
| cg20541238 | cg20751795 |
| cg20546002 | cg20752795 |
| cg20550224 | cg20752818 |
| cg20553394 | cg20752903 |
| cg20554228 | cg20753294 |
| cg20559000 | cg20753954 |
| cg20559608 | cg20755820 |
| cg20568196 | cg20757519 |
| cg20568227 | cg20762044 |
| cg20570410 | cg20766467 |
| cg20573396 | cg20767025 |
| cg20578175 | cg20770339 |
| cg20587543 | cg20771178 |
| cg20590617 | cg20771287 |
| cg20591405 | cg20772101 |
| cg20593831 | cg20776240 |
| cg20594401 | cg20777247 |
| cg20597013 | cg20777920 |
| cg20598560 | cg20779944 |
| cg20603260 | cg20788479 |
| cg20603609 | cg20792512 |
| cg20603637 | cg20795569 |
| cg20606062 | cg20797142 |
| cg20607331 | cg20800844 |
| cg20607769 | cg20801056 |
| cg20612002 | cg20804700 |
| cg20617956 | cg20811266 |
| cg20620147 | cg20811804 |
| cg20620700 | cg20813081 |
| cg20621715 | cg20813965 |
| cg20622089 | cg20814574 |
| cg20623371 | cg20817465 |
| cg20624451 | cg20817483 |
| cg20626099 | cg20819218 |
| cg20627835 | cg20822109 |
| cg20636912 | cg20823742 |
| cg20638626 | cg20835725 |
| cg20642710 | cg20841596 |
| cg20643237 | cg20841906 |
| cg20646950 | cg20844545 |
| cg20649951 | cg20846212 |

TABLE I-continued

Pan Cancer Panel

| | |
|---|---|
| cg20847625 | cg21053015 |
| cg20852605 | cg21056992 |
| cg20852890 | cg21057228 |
| cg20856064 | cg21057435 |
| cg20857455 | cg21057613 |
| cg20860638 | cg21057907 |
| cg20861607 | cg21062931 |
| cg20864389 | cg21064080 |
| cg20868518 | cg21064182 |
| cg20869501 | cg21067341 |
| cg20873718 | cg21067540 |
| cg20875887 | cg21068911 |
| cg20877313 | cg21073859 |
| cg20879085 | cg21074855 |
| cg20880234 | cg21076935 |
| cg20884939 | cg21079345 |
| cg20884984 | cg21080140 |
| cg20885078 | cg21085190 |
| cg20885578 | cg21088534 |
| cg20890313 | cg21088686 |
| cg20891565 | cg21088896 |
| cg20892135 | cg21092303 |
| cg20896631 | cg21092867 |
| cg20901246 | cg21099488 |
| cg20910102 | cg21102477 |
| cg20912211 | cg21106899 |
| cg20914464 | cg21107549 |
| cg20918484 | cg21108220 |
| cg20919556 | cg21116267 |
| cg20919922 | cg21117673 |
| cg20923716 | cg21119525 |
| cg20927059 | cg21121336 |
| cg20927575 | cg21122656 |
| cg20930060 | cg21127268 |
| cg20936013 | cg21128610 |
| cg20937016 | cg21138752 |
| cg20938157 | cg21139392 |
| cg20940153 | cg21142738 |
| cg20941820 | cg21153697 |
| cg20948024 | cg21155380 |
| cg20950465 | cg21155461 |
| cg20950724 | cg21164440 |
| cg20954537 | cg21167167 |
| cg20954960 | cg21167628 |
| cg20954975 | cg21172814 |
| cg20959523 | cg21174533 |
| cg20961469 | cg21176048 |
| cg20966551 | cg21176475 |
| cg20971220 | cg21177599 |
| cg20973347 | cg21179457 |
| cg20973396 | cg21182454 |
| cg20974077 | cg21182461 |
| cg20981058 | cg21188989 |
| cg20981182 | cg21195037 |
| cg20984053 | cg21197973 |
| cg20984663 | cg21204904 |
| cg20991347 | cg21205071 |
| cg21007190 | cg21210985 |
| cg21007414 | cg21212277 |
| cg21010450 | cg21217886 |
| cg21011425 | cg21218082 |
| cg21012362 | cg21220536 |
| cg21022732 | cg21226534 |
| cg21026553 | cg21227040 |
| cg21026663 | cg21231789 |
| cg21029201 | cg21234195 |
| cg21029403 | cg21237313 |
| cg21029447 | cg21239691 |
| cg21035222 | cg21240441 |
| cg21037314 | cg21240762 |
| cg21038156 | cg21241317 |
| cg21039652 | cg21241839 |
| cg21039778 | cg21243939 |
| cg21041580 | cg21244846 |
| cg21046967 | cg21246783 |
| cg21048422 | cg21250296 |
| cg21051989 | cg21253692 |
| cg21052325 | cg21254450 |

TABLE I-continued

Pan Cancer Panel

| | |
|---|---|
| cg21256706 | cg21455939 |
| cg21257950 | cg21460402 |
| cg21258057 | cg21463740 |
| cg21259253 | cg21465360 |
| cg21262300 | cg21474955 |
| cg21264227 | cg21478177 |
| cg21270074 | cg21482403 |
| cg21271681 | cg21483700 |
| cg21273703 | cg21486944 |
| cg21276197 | cg21487923 |
| cg21278102 | cg21490561 |
| cg21278806 | cg21495139 |
| cg21281951 | cg21504815 |
| cg21284880 | cg21504961 |
| cg21285525 | cg21509551 |
| cg21285895 | cg21514086 |
| cg21287489 | cg21517320 |
| cg21291896 | cg21518432 |
| cg21292337 | cg21518938 |
| cg21293611 | cg21520042 |
| cg21294424 | cg21521784 |
| cg21294471 | cg21526173 |
| cg21294935 | cg21529405 |
| cg21296037 | cg21530552 |
| cg21296749 | cg21533806 |
| cg21302562 | cg21535106 |
| cg21303803 | cg21537230 |
| cg21305471 | cg21540437 |
| cg21309100 | cg21541030 |
| cg21310689 | cg21542248 |
| cg21311023 | cg21543150 |
| cg21317132 | cg21546671 |
| cg21325732 | cg21548032 |
| cg21326301 | cg21548414 |
| cg21331473 | cg21548719 |
| cg21332729 | cg21549294 |
| cg21337826 | cg21553524 |
| cg21338532 | cg21555796 |
| cg21340148 | cg21556309 |
| cg21344989 | cg21563078 |
| cg21346925 | cg21569090 |
| cg21348210 | cg21573601 |
| cg21348533 | cg21574404 |
| cg21348752 | cg21574435 |
| cg21351102 | cg21576698 |
| cg21356535 | cg21578322 |
| cg21356837 | cg21581531 |
| cg21357621 | cg21581821 |
| cg21364562 | cg21583160 |
| cg21370527 | cg21583226 |
| cg21379008 | cg21585733 |
| cg21380341 | cg21586412 |
| cg21385047 | cg21589191 |
| cg21388527 | cg21591173 |
| cg21389901 | cg21593941 |
| cg21395152 | cg21594642 |
| cg21399685 | cg21595039 |
| cg21400015 | cg21595503 |
| cg21401647 | cg21596317 |
| cg21401951 | cg21600537 |
| cg21410080 | cg21602557 |
| cg21415643 | cg21606777 |
| cg21421098 | cg21606780 |
| cg21421278 | cg21607453 |
| cg21424120 | cg21610368 |
| cg21424782 | cg21612046 |
| cg21425749 | cg21612207 |
| cg21426387 | cg21614408 |
| cg21433912 | cg21616552 |
| cg21435336 | cg21617058 |
| cg21437481 | cg21620778 |
| cg21437521 | cg21621906 |
| cg21445541 | cg21623748 |
| cg21446511 | cg21624739 |
| cg21448788 | cg21627760 |
| cg21451378 | cg21634064 |
| cg21452805 | cg21637763 |
| cg21454231 | cg21639387 |

TABLE I-continued

Pan Cancer Panel

| | |
|---|---|
| cg21640587 | cg21859434 |
| cg21642176 | cg21860629 |
| cg21644830 | cg21864259 |
| cg21645164 | cg21864996 |
| cg21649051 | cg21868134 |
| cg21653132 | cg21868211 |
| cg21653558 | cg21868774 |
| cg21655844 | cg21870776 |
| cg21656801 | cg21873251 |
| cg21657876 | cg21873817 |
| cg21658235 | cg21875437 |
| cg21660960 | cg21877656 |
| cg21662160 | cg21881273 |
| cg21662494 | cg21884905 |
| cg21662807 | cg21886612 |
| cg21667796 | cg21890726 |
| cg21671020 | cg21901718 |
| cg21673646 | cg21903324 |
| cg21678388 | cg21904937 |
| cg21681396 | cg21908208 |
| cg21685266 | cg21908638 |
| cg21686379 | cg21908706 |
| cg21692936 | cg21913630 |
| cg21701531 | cg21915639 |
| cg21702128 | cg21916655 |
| cg21702506 | cg21921619 |
| cg21709909 | cg21922468 |
| cg21712019 | cg21923442 |
| cg21715963 | cg21926402 |
| cg21725265 | cg21932368 |
| cg21725976 | cg21934564 |
| cg21726284 | cg21940042 |
| cg21727178 | cg21949747 |
| cg21730448 | cg21951425 |
| cg21732915 | cg21953346 |
| cg21733154 | cg21962423 |
| cg21735376 | cg21962603 |
| cg21741689 | cg21963643 |
| cg21742923 | cg21968324 |
| cg21746851 | cg21968580 |
| cg21747958 | cg21972318 |
| cg21760146 | cg21972430 |
| cg21761844 | cg21973449 |
| cg21768566 | cg21981706 |
| cg21773967 | cg21985559 |
| cg21781600 | cg21986225 |
| cg21781828 | cg21986422 |
| cg21782376 | cg21989213 |
| cg21784768 | cg21992350 |
| cg21785847 | cg21994267 |
| cg21786334 | cg21995919 |
| cg21788396 | cg22002075 |
| cg21789044 | cg22007163 |
| cg21789898 | cg22008625 |
| cg21793948 | cg22009488 |
| cg21805221 | cg22010743 |
| cg21806022 | cg22014661 |
| cg21808250 | cg22021178 |
| cg21810188 | cg22021756 |
| cg21810621 | cg22023952 |
| cg21814278 | cg22027897 |
| cg21816336 | cg22028542 |
| cg21816532 | cg22029189 |
| cg21817720 | cg22030419 |
| cg21818749 | cg22031336 |
| cg21825027 | cg22031392 |
| cg21826900 | cg22037077 |
| cg21831898 | cg22037648 |
| cg21835622 | cg22038579 |
| cg21837443 | cg22043720 |
| cg21838880 | cg22049732 |
| cg21839138 | cg22052291 |
| cg21844316 | cg22054918 |
| cg21850038 | cg22058708 |
| cg21850254 | cg22058855 |
| cg21851151 | cg22062265 |
| cg21852439 | cg22062659 |
| cg21857363 | cg22063966 |

TABLE I-continued

Pan Cancer Panel

| |
|---|
| cg22065733 |
| cg22066230 |
| cg22072935 |
| cg22084563 |
| cg22085335 |
| cg22086322 |
| cg22087390 |
| cg22087450 |
| cg22087659 |
| cg22090773 |
| cg22090863 |
| cg22091297 |
| cg22093503 |
| cg22094750 |
| cg22096450 |
| cg22101924 |
| cg22105512 |
| cg22106401 |
| cg22108864 |
| cg22109064 |
| cg22114393 |
| cg22124479 |
| cg22124493 |
| cg22124678 |
| cg22125569 |
| cg22127901 |
| cg22129906 |
| cg22131825 |
| cg22135941 |
| cg22140378 |
| cg22143569 |
| cg22145401 |
| cg22151941 |
| cg22152328 |
| cg22154024 |
| cg22154616 |
| cg22157239 |
| cg22162404 |
| cg22163056 |
| cg22168369 |
| cg22170732 |
| cg22174088 |
| cg22174693 |
| cg22174841 |
| cg22174844 |
| cg22176353 |
| cg22178761 |
| cg22185268 |
| cg22185451 |
| cg22188495 |
| cg22189307 |
| cg22190028 |
| cg22190438 |
| cg22196952 |
| cg22199615 |
| cg22207272 |
| cg22208012 |
| cg22212238 |
| cg22214565 |
| cg22219248 |
| cg22221222 |
| cg22225105 |
| cg22225673 |
| cg22231908 |
| cg22234897 |
| cg22239483 |
| cg22241593 |
| cg22243662 |
| cg22247277 |
| cg22250498 |
| cg22254299 |
| cg22255664 |
| cg22259606 |
| cg22260952 |
| cg22264975 |
| cg22277271 |
| cg22277431 |
| cg22287067 |
| cg22287624 |
| cg22297146 |
| cg22301073 |
| cg22308501 |
| cg22313495 |
| cg22319682 |
| cg22321089 |
| cg22321237 |
| cg22322828 |
| cg22322863 |
| cg22326903 |
| cg22329423 |
| cg22330492 |
| cg22331017 |
| cg22333836 |
| cg22334000 |
| cg22335490 |
| cg22337605 |
| cg22339356 |
| cg22340072 |
| cg22346581 |
| cg22349506 |
| cg22349573 |
| cg22352717 |
| cg22356339 |
| cg22356934 |
| cg22357700 |
| cg22359664 |
| cg22361914 |
| cg22363670 |
| cg22364262 |
| cg22366214 |
| cg22366350 |
| cg22367989 |
| cg22370379 |
| cg22371845 |
| cg22376465 |
| cg22377142 |
| cg22379207 |
| cg22380033 |
| cg22380533 |
| cg22380652 |
| cg22385719 |
| cg22385764 |
| cg22388982 |
| cg22389279 |
| cg22389730 |
| cg22392276 |
| cg22395192 |
| cg22396033 |
| cg22396057 |
| cg22396792 |
| cg22401066 |
| cg22402852 |
| cg22404450 |
| cg22409420 |
| cg22410750 |
| cg22411407 |
| cg22411784 |
| cg22415969 |
| cg22416074 |
| cg22416253 |
| cg22426944 |
| cg22433285 |
| cg22435300 |
| cg22435982 |
| cg22438525 |
| cg22439359 |
| cg22441533 |
| cg22447539 |
| cg22454660 |
| cg22456785 |
| cg22457984 |
| cg22462193 |
| cg22466425 |
| cg22466550 |
| cg22470850 |
| cg22471230 |

TABLE I-continued

Pan Cancer Panel

| | |
|---|---|
| cg22473312 | cg22684008 |
| cg22478210 | cg22684968 |
| cg22478591 | cg22685123 |
| cg22481535 | cg22685245 |
| cg22485350 | cg22685975 |
| cg22487177 | cg22687239 |
| cg22488268 | cg22690294 |
| cg22488998 | cg22693978 |
| cg22489277 | cg22694153 |
| cg22489583 | cg22694480 |
| cg22493809 | cg22696982 |
| cg22494001 | cg22698996 |
| cg22496665 | cg22699044 |
| cg22496968 | cg22699279 |
| cg22497313 | cg22700091 |
| cg22498996 | cg22702331 |
| cg22499565 | cg22702707 |
| cg22500428 | cg22704326 |
| cg22509189 | cg22706420 |
| cg22510582 | cg22709082 |
| cg22512464 | cg22709563 |
| cg22513924 | cg22710306 |
| cg22516651 | cg22710840 |
| cg22517656 | cg22711621 |
| cg22521696 | cg22711679 |
| cg22528685 | cg22712329 |
| cg22529861 | cg22715021 |
| cg22535307 | cg22718431 |
| cg22535359 | cg22719559 |
| cg22539985 | cg22724500 |
| cg22541378 | cg22725460 |
| cg22541911 | cg22727304 |
| cg22546686 | cg22728534 |
| cg22549268 | cg22731064 |
| cg22549986 | cg22736718 |
| cg22555744 | cg22737001 |
| cg22557029 | cg22737282 |
| cg22559669 | cg22744680 |
| cg22560190 | cg22745781 |
| cg22560410 | cg22748740 |
| cg22561889 | cg22750155 |
| cg22564317 | cg22753515 |
| cg22569523 | cg22758700 |
| cg22577136 | cg22761704 |
| cg22578125 | cg22762180 |
| cg22581219 | cg22762844 |
| cg22582113 | cg22778421 |
| cg22582862 | cg22781950 |
| cg22587602 | cg22782191 |
| cg22588307 | cg22783358 |
| cg22593554 | cg22784589 |
| cg22609576 | cg22789900 |
| cg22610211 | cg22790257 |
| cg22614355 | cg22790973 |
| cg22615158 | cg22791632 |
| cg22623967 | cg22794494 |
| cg22628500 | cg22795212 |
| cg22631459 | cg22795590 |
| cg22632069 | cg22797164 |
| cg22633988 | cg22797570 |
| cg22634689 | cg22798201 |
| cg22636429 | cg22800581 |
| cg22637507 | cg22806837 |
| cg22637594 | cg22808175 |
| cg22638185 | cg22812733 |
| cg22639895 | cg22814737 |
| cg22647810 | cg22815953 |
| cg22648949 | cg22816621 |
| cg22652406 | cg22819502 |
| cg22657536 | cg22819616 |
| cg22658660 | cg22822824 |
| cg22663545 | cg22826936 |
| cg22664307 | cg22828045 |
| cg22665276 | cg22829821 |
| cg22669058 | cg22831269 |
| cg22669787 | cg22834096 |
| cg22678708 | cg22834653 |
| cg22683038 | cg22835852 |

TABLE I-continued

Pan Cancer Panel

| |
|---|
| cg22841258 |
| cg22845037 |
| cg22845159 |
| cg22847691 |
| cg22849482 |
| cg22853371 |
| cg22853986 |
| cg22854679 |
| cg22856512 |
| cg22861279 |
| cg22862480 |
| cg22863209 |
| cg22864416 |
| cg22865286 |
| cg22865582 |
| cg22865720 |
| cg22866835 |
| cg22870899 |
| cg22874046 |
| cg22874858 |
| cg22880757 |
| cg22886237 |
| cg22886512 |
| cg22889755 |
| cg22892328 |
| cg22896991 |
| cg22902177 |
| cg22902535 |
| cg22905274 |
| cg22906273 |
| cg22906700 |
| cg22907739 |
| cg22909769 |
| cg22913249 |
| cg22913933 |
| cg22919784 |
| cg22920665 |
| cg22922289 |
| cg22923827 |
| cg22924838 |
| cg22927510 |
| cg22927696 |
| cg22929692 |
| cg22929808 |
| cg22931738 |
| cg22934970 |
| cg22935262 |
| cg22935432 |
| cg22935821 |
| cg22936457 |
| cg22936975 |
| cg22937891 |
| cg22938308 |
| cg22939193 |
| cg22939802 |
| cg22943762 |
| cg22944461 |
| cg22944662 |
| cg22945872 |
| cg22946876 |
| cg22947959 |
| cg22948236 |
| cg22949149 |
| cg22951056 |
| cg22952210 |
| cg22955973 |
| cg22956410 |
| cg22960185 |
| cg22960186 |
| cg22961275 |
| cg22963915 |
| cg22972972 |
| cg22973319 |
| cg22974804 |
| cg22976979 |
| cg22977876 |
| cg22987590 |
| cg22991959 |
| cg22994808 |
| cg22995684 |
| cg22996534 |
| cg22998421 |
| cg23000811 |
| cg23003258 |
| cg23003534 |
| cg23007898 |
| cg23008047 |
| cg23008646 |
| cg23009315 |
| cg23015949 |
| cg23017840 |
| cg23021477 |
| cg23023820 |
| cg23025942 |
| cg23027521 |
| cg23027583 |
| cg23029526 |
| cg23032045 |
| cg23033785 |
| cg23033906 |
| cg23037648 |
| cg23042796 |
| cg23045258 |
| cg23045719 |
| cg23046903 |
| cg23048068 |
| cg23048455 |
| cg23051578 |
| cg23052615 |
| cg23057706 |
| cg23057732 |
| cg23061718 |
| cg23062425 |
| cg23067281 |
| cg23068731 |
| cg23069167 |
| cg23070026 |
| cg23070111 |
| cg23071808 |
| cg23076299 |
| cg23079217 |
| cg23080179 |
| cg23081580 |
| cg23083315 |
| cg23084951 |
| cg23089764 |
| cg23091984 |
| cg23093462 |
| cg23095615 |
| cg23096553 |
| cg23096644 |
| cg23097143 |
| cg23097155 |
| cg23097985 |
| cg23100152 |
| cg23103993 |
| cg23107161 |
| cg23108125 |
| cg23109721 |
| cg23116322 |
| cg23116658 |
| cg23117778 |
| cg23123909 |
| cg23127249 |
| cg23129170 |
| cg23130076 |
| cg23131007 |
| cg23134869 |
| cg23138678 |
| cg23139473 |
| cg23140554 |
| cg23143233 |
| cg23149560 |
| cg23151421 |
| cg23151862 |
| cg23152885 |

TABLE I-continued

Pan Cancer Panel

| | |
|---|---|
| cg23156742 | cg23344452 |
| cg23164203 | cg23345097 |
| cg23164681 | cg23345500 |
| cg23168000 | cg23347273 |
| cg23171203 | cg23353893 |
| cg23181844 | cg23354716 |
| cg23183469 | cg23355674 |
| cg23183906 | cg23356993 |
| cg23185921 | cg23357265 |
| cg23186104 | cg23358710 |
| cg23190994 | cg23359276 |
| cg23191118 | cg23359706 |
| cg23192644 | cg23360190 |
| cg23197935 | cg23361355 |
| cg23198529 | cg23361368 |
| cg23198902 | cg23363014 |
| cg23204296 | cg23363911 |
| cg23206311 | cg23370536 |
| cg23207710 | cg23372128 |
| cg23209255 | cg23372936 |
| cg23210365 | cg23391006 |
| cg23211714 | cg23393521 |
| cg23220551 | cg23397571 |
| cg23221885 | cg23400883 |
| cg23224120 | cg23402444 |
| cg23225690 | cg23407507 |
| cg23226129 | cg23409774 |
| cg23227355 | cg23410069 |
| cg23228540 | cg23410627 |
| cg23232563 | cg23411725 |
| cg23232615 | cg23413066 |
| cg23233141 | cg23416197 |
| cg23236404 | cg23418339 |
| cg23240013 | cg23419328 |
| cg23242697 | cg23421262 |
| cg23245297 | cg23423382 |
| cg23246978 | cg23424273 |
| cg23248007 | cg23424766 |
| cg23250910 | cg23426054 |
| cg23252261 | cg23429507 |
| cg23256664 | cg23429696 |
| cg23257840 | cg23431892 |
| cg23261102 | cg23433527 |
| cg23264625 | cg23433607 |
| cg23267450 | cg23434186 |
| cg23268677 | cg23435746 |
| cg23274680 | cg23437733 |
| cg23275673 | cg23448584 |
| cg23276878 | cg23455517 |
| cg23278267 | cg23456144 |
| cg23281215 | cg23458341 |
| cg23282051 | cg23460835 |
| cg23282585 | cg23461800 |
| cg23291136 | cg23463144 |
| cg23291305 | cg23463742 |
| cg23294388 | cg23464032 |
| cg23295127 | cg23465990 |
| cg23296010 | cg23468897 |
| cg23296408 | cg23469706 |
| cg23300289 | cg23473285 |
| cg23300368 | cg23474794 |
| cg23306832 | cg23477406 |
| cg23310850 | cg23479561 |
| cg23317907 | cg23481605 |
| cg23318713 | cg23482397 |
| cg23318786 | cg23486345 |
| cg23319285 | cg23491124 |
| cg23324824 | cg23493510 |
| cg23326228 | cg23497217 |
| cg23326811 | cg23497767 |
| cg23331220 | cg23498273 |
| cg23333513 | cg23498748 |
| cg23333878 | cg23498771 |
| cg23335390 | cg23501467 |
| cg23337116 | cg23502565 |
| cg23338170 | cg23504463 |
| cg23338503 | cg23508052 |
| cg23341163 | cg23508667 |

TABLE I-continued

Pan Cancer Panel

| | |
|---|---|
| cg23511613 | cg23705973 |
| cg23513318 | cg23710492 |
| cg23513690 | cg23715700 |
| cg23514110 | cg23718026 |
| cg23514324 | cg23718924 |
| cg23515325 | cg23719207 |
| cg23516634 | cg23721712 |
| cg23520075 | cg23722428 |
| cg23522427 | cg23728669 |
| cg23524341 | cg23730260 |
| cg23525853 | cg23730436 |
| cg23526973 | cg23733133 |
| cg23528625 | cg23733525 |
| cg23530053 | cg23737229 |
| cg23532246 | cg23738624 |
| cg23532765 | cg23743449 |
| cg23533198 | cg23752691 |
| cg23537193 | cg23753247 |
| cg23543123 | cg23758016 |
| cg23543615 | cg23760165 |
| cg23547515 | cg23761820 |
| cg23549225 | cg23763424 |
| cg23553119 | cg23764381 |
| cg23556533 | cg23773266 |
| cg23563443 | cg23773809 |
| cg23565749 | cg23782001 |
| cg23570590 | cg23782616 |
| cg23572228 | cg23782734 |
| cg23574053 | cg23789846 |
| cg23581656 | cg23791611 |
| cg23584332 | cg23791764 |
| cg23585337 | cg23792245 |
| cg23587805 | cg23799276 |
| cg23593537 | cg23801012 |
| cg23596620 | cg23801021 |
| cg23599104 | cg23801029 |
| cg23599559 | cg23807354 |
| cg23601066 | cg23811464 |
| cg23604012 | cg23812393 |
| cg23607033 | cg23813514 |
| cg23609571 | cg23833588 |
| cg23609905 | cg23836621 |
| cg23612557 | cg23841903 |
| cg23614229 | cg23847701 |
| cg23614979 | cg23849078 |
| cg23618638 | cg23849311 |
| cg23620052 | cg23851476 |
| cg23620228 | cg23851860 |
| cg23623270 | cg23855030 |
| cg23634087 | cg23855505 |
| cg23634711 | cg23867081 |
| cg23637314 | cg23868141 |
| cg23642766 | cg23872082 |
| cg23647191 | cg23872756 |
| cg23651323 | cg23877401 |
| cg23651502 | cg23881902 |
| cg23658326 | cg23882234 |
| cg23658744 | cg23883409 |
| cg23662501 | cg23889086 |
| cg23664459 | cg23890800 |
| cg23665973 | cg23891251 |
| cg23668806 | cg23892336 |
| cg23669159 | cg23893997 |
| cg23670599 | cg23896874 |
| cg23674469 | cg23897733 |
| cg23677039 | cg23900774 |
| cg23680282 | cg23901063 |
| cg23680448 | cg23904854 |
| cg23684074 | cg23905374 |
| cg23684807 | cg23905542 |
| cg23685151 | cg23910786 |
| cg23687194 | cg23912231 |
| cg23690804 | cg23912239 |
| cg23695485 | cg23921342 |
| cg23695687 | cg23922718 |
| cg23698058 | cg23928824 |
| cg23700044 | cg23931421 |
| cg23702412 | cg23933381 |

TABLE I-continued

Pan Cancer Panel

| | |
|---|---|
| cg23934533 | cg24087403 |
| cg23936023 | cg24088775 |
| cg23937586 | cg24089133 |
| cg23939037 | cg24092470 |
| cg23942980 | cg24095353 |
| cg23943360 | cg24096925 |
| cg23947039 | cg24098927 |
| cg23951198 | cg24098938 |
| cg23952189 | cg24100726 |
| cg23952663 | cg24101560 |
| cg23954057 | cg24102241 |
| cg23954629 | cg24102266 |
| cg23956966 | cg24102726 |
| cg23957915 | cg24103837 |
| cg23963136 | cg24106943 |
| cg23966569 | cg24111955 |
| cg23967540 | cg24113782 |
| cg23967742 | cg24116259 |
| cg23973417 | cg24117376 |
| cg23974921 | cg24119079 |
| cg23974944 | cg24120847 |
| cg23975375 | cg24122218 |
| cg23977631 | cg24128066 |
| cg23977954 | cg24128130 |
| cg23980468 | cg24130774 |
| cg23982678 | cg24131748 |
| cg23986470 | cg24132791 |
| cg23989053 | cg24133836 |
| cg23990723 | cg24134219 |
| cg23991039 | cg24134479 |
| cg23991622 | cg24140030 |
| cg23992449 | cg24148719 |
| cg23994051 | cg24150232 |
| cg23994917 | cg24158594 |
| cg23996123 | cg24161615 |
| cg23996829 | cg24163616 |
| cg24003542 | cg24164873 |
| cg24004478 | cg24166694 |
| cg24009736 | cg24167118 |
| cg24014143 | cg24167603 |
| cg24016939 | cg24176678 |
| cg24018609 | cg24182470 |
| cg24024176 | cg24182831 |
| cg24025896 | cg24184687 |
| cg24029414 | cg24186750 |
| cg24033330 | cg24188073 |
| cg24034347 | cg24188919 |
| cg24035210 | cg24190127 |
| cg24036126 | cg24190415 |
| cg24037629 | cg24193383 |
| cg24037897 | cg24193855 |
| cg24039019 | cg24199987 |
| cg24041269 | cg24201964 |
| cg24044288 | cg24205633 |
| cg24045482 | cg24212855 |
| cg24050511 | cg24216220 |
| cg24050613 | cg24217844 |
| cg24053587 | cg24218295 |
| cg24056307 | cg24219929 |
| cg24059115 | cg24227728 |
| cg24065044 | cg24229589 |
| cg24067214 | cg24231037 |
| cg24068708 | cg24231716 |
| cg24070213 | cg24236085 |
| cg24072311 | cg24236887 |
| cg24072474 | cg24238564 |
| cg24072819 | cg24239014 |
| cg24075738 | cg24241129 |
| cg24077593 | cg24241429 |
| cg24078363 | cg24242082 |
| cg24078451 | cg24244270 |
| cg24078985 | cg24251048 |
| cg24080313 | cg24253255 |
| cg24082730 | cg24255728 |
| cg24083324 | cg24265747 |
| cg24083817 | cg24265806 |
| cg24084504 | cg24266238 |
| cg24085719 | cg24269434 |

TABLE I-continued

Pan Cancer Panel

| | |
|---|---|
| cg24278138 | cg24447438 |
| cg24280645 | cg24450494 |
| cg24283621 | cg24450582 |
| cg24284436 | cg24456130 |
| cg24287438 | cg24457126 |
| cg24290286 | cg24458474 |
| cg24293044 | cg24461964 |
| cg24295125 | cg24463006 |
| cg24298255 | cg24468105 |
| cg24304249 | cg24468682 |
| cg24305381 | cg24474130 |
| cg24306353 | cg24481381 |
| cg24306585 | cg24482021 |
| cg24310038 | cg24482053 |
| cg24311947 | cg24482234 |
| cg24313597 | cg24487076 |
| cg24319718 | cg24488059 |
| cg24321030 | cg24488602 |
| cg24323031 | cg24491766 |
| cg24325204 | cg24494316 |
| cg24326232 | cg24495982 |
| cg24327262 | cg24496978 |
| cg24330818 | cg24497541 |
| cg24331598 | cg24505307 |
| cg24333469 | cg24507144 |
| cg24334111 | cg24508611 |
| cg24334243 | cg24509668 |
| cg24334304 | cg24510700 |
| cg24334809 | cg24516147 |
| cg24335138 | cg24517380 |
| cg24336278 | cg24519084 |
| cg24337151 | cg24521848 |
| cg24339193 | cg24524308 |
| cg24339897 | cg24525509 |
| cg24341498 | cg24525913 |
| cg24341944 | cg24526702 |
| cg24344214 | cg24528447 |
| cg24344662 | cg24532523 |
| cg24352971 | cg24533678 |
| cg24361849 | cg24540521 |
| cg24365518 | cg24542441 |
| cg24369746 | cg24546984 |
| cg24370755 | cg24548682 |
| cg24371216 | cg24548754 |
| cg24371225 | cg24553364 |
| cg24372550 | cg24561572 |
| cg24374861 | cg24564088 |
| cg24377330 | cg24568842 |
| cg24382801 | cg24569637 |
| cg24383902 | cg24573719 |
| cg24385334 | cg24575245 |
| cg24385694 | cg24577420 |
| cg24385733 | cg24577594 |
| cg24386906 | cg24578679 |
| cg24396358 | cg24581326 |
| cg24400921 | cg24583766 |
| cg24402603 | cg24588375 |
| cg24404479 | cg24592207 |
| cg24405179 | cg24593694 |
| cg24405617 | cg24594177 |
| cg24407243 | cg24596027 |
| cg24407308 | cg24597158 |
| cg24407327 | cg24599205 |
| cg24409356 | cg24604604 |
| cg24415565 | cg24606935 |
| cg24419856 | cg24613083 |
| cg24422297 | cg24615528 |
| cg24425021 | cg24616138 |
| cg24427504 | cg24623497 |
| cg24427993 | cg24625128 |
| cg24432048 | cg24626079 |
| cg24434959 | cg24629122 |
| cg24435401 | cg24630201 |
| cg24437429 | cg24631970 |
| cg24437625 | cg24633756 |
| cg24438313 | cg24634422 |
| cg24441185 | cg24635156 |
| cg24444188 | cg24635468 |

TABLE I-continued

Pan Cancer Panel

| | |
|---|---|
| cg24638647 | cg24791380 |
| cg24638668 | cg24794347 |
| cg24641522 | cg24797187 |
| cg24641993 | cg24799047 |
| cg24648594 | cg24802771 |
| cg24650522 | cg24804172 |
| cg24651706 | cg24804544 |
| cg24653100 | cg24806963 |
| cg24660030 | cg24807106 |
| cg24663663 | cg24808223 |
| cg24664861 | cg24809072 |
| cg24668364 | cg24810439 |
| cg24678700 | cg24810741 |
| cg24679395 | cg24814784 |
| cg24685601 | cg24817430 |
| cg24692068 | cg24818145 |
| cg24695316 | cg24824266 |
| cg24699519 | cg24824417 |
| cg24700222 | cg24825262 |
| cg24700663 | cg24826867 |
| cg24701809 | cg24832140 |
| cg24703168 | cg24837680 |
| cg24703717 | cg24838654 |
| cg24706932 | cg24843474 |
| cg24707051 | cg24855943 |
| cg24709718 | cg24856140 |
| cg24710320 | cg24863791 |
| cg24710870 | cg24867142 |
| cg24713878 | cg24868134 |
| cg24714666 | cg24868201 |
| cg24718729 | cg24870497 |
| cg24718846 | cg24871132 |
| cg24718866 | cg24876786 |
| cg24719487 | cg24877195 |
| cg24720571 | cg24878071 |
| cg24720583 | cg24880024 |
| cg24722346 | cg24884207 |
| cg24727133 | cg24884572 |
| cg24731635 | cg24885126 |
| cg24732574 | cg24886770 |
| cg24732929 | cg24887139 |
| cg24733262 | cg24887416 |
| cg24733530 | cg24890043 |
| cg24734586 | cg24890054 |
| cg24738779 | cg24895258 |
| cg24740026 | cg24895834 |
| cg24740509 | cg24896860 |
| cg24740531 | cg24899571 |
| cg24740568 | cg24906525 |
| cg24742512 | cg24908499 |
| cg24742832 | cg24910410 |
| cg24743639 | cg24913324 |
| cg24745633 | cg24914278 |
| cg24746100 | cg24917627 |
| cg24748867 | cg24917799 |
| cg24753200 | cg24919790 |
| cg24753473 | cg24922817 |
| cg24758426 | cg24924091 |
| cg24759994 | cg24924560 |
| cg24760848 | cg24928995 |
| cg24760922 | cg24929737 |
| cg24765016 | cg24930223 |
| cg24768974 | cg24933173 |
| cg24769513 | cg24935773 |
| cg24769821 | cg24937696 |
| cg24770596 | cg24942272 |
| cg24770985 | cg24954684 |
| cg24771349 | cg24957657 |
| cg24772828 | cg24965937 |
| cg24775172 | cg24973289 |
| cg24776469 | cg24975662 |
| cg24777065 | cg24976104 |
| cg24778383 | cg24980893 |
| cg24783322 | cg24980994 |
| cg24785946 | cg24984301 |
| cg24788053 | cg24984523 |
| cg24789348 | cg24985459 |
| cg24789487 | cg24994173 |

TABLE I-continued

Pan Cancer Panel

| | |
|---|---|
| cg24997589 | cg25203704 |
| cg24997989 | cg25204440 |
| cg24999255 | cg25204543 |
| cg25008346 | cg25208479 |
| cg25010146 | cg25208969 |
| cg25010361 | cg25211525 |
| cg25012864 | cg25213928 |
| cg25014117 | cg25214923 |
| cg25014411 | cg25215340 |
| cg25015504 | cg25217365 |
| cg25016127 | cg25220460 |
| cg25024676 | cg25220625 |
| cg25026703 | cg25221442 |
| cg25031380 | cg25223355 |
| cg25033139 | cg25224568 |
| cg25037730 | cg25226768 |
| cg25038060 | cg25227274 |
| cg25038283 | cg25229114 |
| cg25042239 | cg25230111 |
| cg25049387 | cg25232660 |
| cg25049597 | cg25236324 |
| cg25052970 | cg25241964 |
| cg25053531 | cg25244476 |
| cg25057269 | cg25246092 |
| cg25062812 | cg25248628 |
| cg25066040 | cg25251738 |
| cg25066490 | cg25253217 |
| cg25067153 | cg25255293 |
| cg25071520 | cg25255795 |
| cg25072436 | cg25262044 |
| cg25073829 | cg25263140 |
| cg25074071 | cg25267765 |
| cg25074185 | cg25268754 |
| cg25075147 | cg25270670 |
| cg25087487 | cg25272554 |
| cg25089142 | cg25275166 |
| cg25092328 | cg25276412 |
| cg25092681 | cg25280092 |
| cg25094411 | cg25283609 |
| cg25097514 | cg25285794 |
| cg25098208 | cg25291355 |
| cg25103850 | cg25291387 |
| cg25104716 | cg25297849 |
| cg25115993 | cg25300214 |
| cg25116125 | cg25300584 |
| cg25121332 | cg25301406 |
| cg25122590 | cg25303599 |
| cg25122820 | cg25307691 |
| cg25129152 | cg25308231 |
| cg25130672 | cg25308427 |
| cg25130993 | cg25310909 |
| cg25137030 | cg25314902 |
| cg25137687 | cg25315855 |
| cg25141069 | cg25317664 |
| cg25141957 | cg25318301 |
| cg25147139 | cg25320115 |
| cg25151274 | cg25322095 |
| cg25151353 | cg25325038 |
| cg25152368 | cg25325588 |
| cg25152631 | cg25326896 |
| cg25153601 | cg25327452 |
| cg25155846 | cg25328795 |
| cg25157280 | cg25330361 |
| cg25158678 | cg25330514 |
| cg25160286 | cg25331703 |
| cg25160978 | cg25332377 |
| cg25161976 | cg25333258 |
| cg25164495 | cg25337705 |
| cg25166381 | cg25338262 |
| cg25167838 | cg25338766 |
| cg25178399 | cg25339408 |
| cg25179291 | cg25344133 |
| cg25184481 | cg25346193 |
| cg25192419 | cg25347098 |
| cg25195415 | cg25351036 |
| cg25202131 | cg25353930 |
| cg25202298 | cg25358770 |
| cg25202636 | cg25360929 |

TABLE I-continued

Pan Cancer Panel

| |
|---|
| cg25361907 |
| cg25365565 |
| cg25365746 |
| cg25367905 |
| cg25369168 |
| cg25371950 |
| cg25372335 |
| cg25372568 |
| cg25373063 |
| cg25373100 |
| cg25375340 |
| cg25381667 |
| cg25381711 |
| cg25386820 |
| cg25389261 |
| cg25389470 |
| cg25395413 |
| cg25402610 |
| cg25402685 |
| cg25404025 |
| cg25405984 |
| cg25406166 |
| cg25406735 |
| cg25406872 |
| cg25411849 |
| cg25421903 |
| cg25422351 |
| cg25423755 |
| cg25426776 |
| cg25428398 |
| cg25433267 |
| cg25436849 |
| cg25437410 |
| cg25438415 |
| cg25438963 |
| cg25439973 |
| cg25442239 |
| cg25445612 |
| cg25449542 |
| cg25449655 |
| cg25450449 |
| cg25450450 |
| cg25451874 |
| cg25452974 |
| cg25454116 |
| cg25454890 |
| cg25463470 |
| cg25464457 |
| cg25465938 |
| cg25468863 |
| cg25471365 |
| cg25471478 |
| cg25475603 |
| cg25480117 |
| cg25485192 |
| cg25492350 |
| cg25497529 |
| cg25502618 |
| cg25503881 |
| cg25504443 |
| cg25506797 |
| cg25506879 |
| cg25508217 |
| cg25510643 |
| cg25511237 |
| cg25511332 |
| cg25513173 |
| cg25514947 |
| cg25518386 |
| cg25521086 |
| cg25522355 |
| cg25530246 |
| cg25530601 |
| cg25532501 |
| cg25532925 |
| cg25533096 |
| cg25533556 |
| cg25537962 |
| cg25538602 |
| cg25544146 |
| cg25547957 |
| cg25549230 |
| cg25555336 |
| cg25555424 |
| cg25560333 |
| cg25561440 |
| cg25563233 |
| cg25565138 |
| cg25565383 |
| cg25567337 |
| cg25568243 |
| cg25571757 |
| cg25572367 |
| cg25574812 |
| cg25577023 |
| cg25578609 |
| cg25583128 |
| cg25583491 |
| cg25587181 |
| cg25587535 |
| cg25590392 |
| cg25594636 |
| cg25594899 |
| cg25598530 |
| cg25598672 |
| cg25602490 |
| cg25605601 |
| cg25607321 |
| cg25608973 |
| cg25611476 |
| cg25616216 |
| cg25618087 |
| cg25619607 |
| cg25623721 |
| cg25623934 |
| cg25626312 |
| cg25628481 |
| cg25629572 |
| cg25635144 |
| cg25643819 |
| cg25645687 |
| cg25649038 |
| cg25655799 |
| cg25660010 |
| cg25667335 |
| cg25670839 |
| cg25672142 |
| cg25678532 |
| cg25679366 |
| cg25681618 |
| cg25681688 |
| cg25682653 |
| cg25687071 |
| cg25689079 |
| cg25693289 |
| cg25701418 |
| cg25705836 |
| cg25714069 |
| cg25720022 |
| cg25721451 |
| cg25724441 |
| cg25726414 |
| cg25726789 |
| cg25727572 |
| cg25729826 |
| cg25734420 |
| cg25734490 |
| cg25734572 |
| cg25741578 |
| cg25741731 |
| cg25741953 |
| cg25742540 |
| cg25745651 |
| cg25749267 |
| cg25756166 |
| cg25756435 |

TABLE I-continued

Pan Cancer Panel

| | |
|---|---|
| cg25756853 | cg25934680 |
| cg25758217 | cg25938977 |
| cg25760229 | cg25942031 |
| cg25765619 | cg25946952 |
| cg25767504 | cg25947544 |
| cg25767985 | cg25950369 |
| cg25771677 | cg25951582 |
| cg25774276 | cg25954223 |
| cg25775832 | cg25955837 |
| cg25776555 | cg25958857 |
| cg25776856 | cg25966893 |
| cg25782003 | cg25968571 |
| cg25783173 | cg25970618 |
| cg25786436 | cg25973895 |
| cg25789216 | cg25975626 |
| cg25793521 | cg25976563 |
| cg25793630 | cg25977958 |
| cg25794153 | cg25982140 |
| cg25794402 | cg25988717 |
| cg25796631 | cg25989216 |
| cg25798122 | cg25989719 |
| cg25799020 | cg25990647 |
| cg25800082 | cg25996614 |
| cg25800170 | cg25999722 |
| cg25803642 | cg26002713 |
| cg25804018 | cg26002784 |
| cg25804470 | cg26005082 |
| cg25804860 | cg26005761 |
| cg25805709 | cg26008007 |
| cg25808577 | cg26012941 |
| cg25808892 | cg26015176 |
| cg25808906 | cg26015401 |
| cg25809635 | cg26016484 |
| cg25817261 | cg26020635 |
| cg25823419 | cg26025543 |
| cg25824543 | cg26031047 |
| cg25826913 | cg26031255 |
| cg25830048 | cg26031541 |
| cg25831204 | cg26032101 |
| cg25832771 | cg26033293 |
| cg25834869 | cg26035323 |
| cg25835225 | cg26036993 |
| cg25835669 | cg26037945 |
| cg25836094 | cg26039848 |
| cg25837710 | cg26040332 |
| cg25840208 | cg26045220 |
| cg25841943 | cg26049726 |
| cg25846285 | cg26049744 |
| cg25848557 | cg26056104 |
| cg25851842 | cg26056348 |
| cg25859141 | cg26063563 |
| cg25868286 | cg26075208 |
| cg25868769 | cg26075747 |
| cg25868998 | cg26076412 |
| cg25870025 | cg26076750 |
| cg25872752 | cg26079699 |
| cg25874034 | cg26080444 |
| cg25874421 | cg26087678 |
| cg25875316 | cg26090855 |
| cg25876509 | cg26097011 |
| cg25885108 | cg26099766 |
| cg25887236 | cg26100711 |
| cg25889711 | cg26101410 |
| cg25901204 | cg26105156 |
| cg25910314 | cg26107850 |
| cg25912580 | cg26108678 |
| cg25912827 | cg26111157 |
| cg25917510 | cg26111761 |
| cg25917621 | cg26113636 |
| cg25918303 | cg26114642 |
| cg25920483 | cg26118408 |
| cg25921512 | cg26119367 |
| cg25924096 | cg26124242 |
| cg25924911 | cg26125811 |
| cg25925764 | cg26126052 |
| cg25927164 | cg26129310 |
| cg25928603 | cg26131754 |
| cg25931385 | cg26131803 |

TABLE I-continued

Pan Cancer Panel

| |
|---|
| cg26132084 |
| cg26135012 |
| cg26135506 |
| cg26137971 |
| cg26144437 |
| cg26146542 |
| cg26147351 |
| cg26147657 |
| cg26149167 |
| cg26150071 |
| cg26151087 |
| cg26154342 |
| cg26154670 |
| cg26161849 |
| cg26162932 |
| cg26180126 |
| cg26186613 |
| cg26187876 |
| cg26198463 |
| cg26202915 |
| cg26205131 |
| cg26207201 |
| cg26209058 |
| cg26211360 |
| cg26212496 |
| cg26219095 |
| cg26220298 |
| cg26220773 |
| cg26224223 |
| cg26224915 |
| cg26225694 |
| cg26226802 |
| cg26228351 |
| cg26232715 |
| cg26233374 |
| cg26237168 |
| cg26240185 |
| cg26243894 |
| cg26245302 |
| cg26245667 |
| cg26246411 |
| cg26248878 |
| cg26256158 |
| cg26256916 |
| cg26258845 |
| cg26258944 |
| cg26261793 |
| cg26261973 |
| cg26263773 |
| cg26268636 |
| cg26268866 |
| cg26269703 |
| cg26270362 |
| cg26273150 |
| cg26274596 |
| cg26276294 |
| cg26277730 |
| cg26281453 |
| cg26282655 |
| cg26284638 |
| cg26284982 |
| cg26286805 |
| cg26288577 |
| cg26293015 |
| cg26297688 |
| cg26298979 |
| cg26302094 |
| cg26307820 |
| cg26308113 |
| cg26309111 |
| cg26313152 |
| cg26316082 |
| cg26322231 |
| cg26324132 |
| cg26325209 |
| cg26325806 |
| cg26327071 |
| cg26327118 |
| cg26331625 |
| cg26332534 |
| cg26333513 |
| cg26333822 |
| cg26333837 |
| cg26335281 |
| cg26337020 |
| cg26337123 |
| cg26338195 |
| cg26339484 |
| cg26344233 |
| cg26349375 |
| cg26349672 |
| cg26355004 |
| cg26365299 |
| cg26366048 |
| cg26366107 |
| cg26367591 |
| cg26370608 |
| cg26375461 |
| cg26376168 |
| cg26384031 |
| cg26386846 |
| cg26386852 |
| cg26387473 |
| cg26391350 |
| cg26392989 |
| cg26394825 |
| cg26396617 |
| cg26400840 |
| cg26404669 |
| cg26408235 |
| cg26410121 |
| cg26410483 |
| cg26412722 |
| cg26422059 |
| cg26425669 |
| cg26426142 |
| cg26428136 |
| cg26429856 |
| cg26433722 |
| cg26436315 |
| cg26436330 |
| cg26444995 |
| cg26445292 |
| cg26448406 |
| cg26448489 |
| cg26450740 |
| cg26457761 |
| cg26458288 |
| cg26459419 |
| cg26459700 |
| cg26460816 |
| cg26464411 |
| cg26464889 |
| cg26465214 |
| cg26466323 |
| cg26466856 |
| cg26473651 |
| cg26477844 |
| cg26478074 |
| cg26478485 |
| cg26482665 |
| cg26485174 |
| cg26487082 |
| cg26487948 |
| cg26489994 |
| cg26494225 |
| cg26495865 |
| cg26498020 |
| cg26499055 |
| cg26517151 |
| cg26519745 |
| cg26520120 |
| cg26520722 |
| cg26522240 |
| cg26523670 |
| cg26524541 |

TABLE I-continued

Pan Cancer Panel

| | |
|---|---|
| cg26528620 | cg26705553 |
| cg26529911 | cg26708548 |
| cg26532253 | cg26708817 |
| cg26533949 | cg26709356 |
| cg26534508 | cg26709950 |
| cg26535805 | cg26713507 |
| cg26538529 | cg26715571 |
| cg26539524 | cg26717983 |
| cg26539593 | cg26717995 |
| cg26541920 | cg26720389 |
| cg26542888 | cg26725153 |
| cg26544277 | cg26725274 |
| cg26546557 | cg26729197 |
| cg26548288 | cg26731119 |
| cg26549326 | cg26732691 |
| cg26551211 | cg26744375 |
| cg26551897 | cg26745332 |
| cg26560928 | cg26745551 |
| cg26561148 | cg26745770 |
| cg26564040 | cg26754826 |
| cg26566415 | cg26756506 |
| cg26569144 | cg26757053 |
| cg26569469 | cg26768712 |
| cg26571942 | cg26770917 |
| cg26573321 | cg26774079 |
| cg26575690 | cg26776069 |
| cg26575738 | cg26781150 |
| cg26577201 | cg26784596 |
| cg26577454 | cg26785250 |
| cg26580421 | cg26785617 |
| cg26580801 | cg26788916 |
| cg26582768 | cg26789332 |
| cg26583041 | cg26789732 |
| cg26592281 | cg26789869 |
| cg26597539 | cg26790372 |
| cg26599209 | cg26791905 |
| cg26600608 | cg26792080 |
| cg26600954 | cg26792116 |
| cg26605406 | cg26792755 |
| cg26605467 | cg26795730 |
| cg26606184 | cg26796283 |
| cg26606256 | cg26797372 |
| cg26612362 | cg26797585 |
| cg26613140 | cg26798879 |
| cg26615127 | cg26799802 |
| cg26618965 | cg26800162 |
| cg26620450 | cg26800371 |
| cg26625629 | cg26802053 |
| cg26626525 | cg26802291 |
| cg26635208 | cg26815291 |
| cg26635845 | cg26820118 |
| cg26640467 | cg26822161 |
| cg26642510 | cg26823584 |
| cg26644059 | cg26824467 |
| cg26647219 | cg26825751 |
| cg26647312 | cg26825934 |
| cg26649005 | cg26826871 |
| cg26652447 | cg26831241 |
| cg26653400 | cg26832509 |
| cg26654790 | cg26834887 |
| cg26654994 | cg26838995 |
| cg26660414 | cg26839117 |
| cg26660801 | cg26840598 |
| cg26664090 | cg26843430 |
| cg26664797 | cg26847805 |
| cg26667720 | cg26851796 |
| cg26672104 | cg26853987 |
| cg26672688 | cg26857911 |
| cg26673436 | cg26859900 |
| cg26674800 | cg26861593 |
| cg26675876 | cg26862527 |
| cg26678852 | cg26864834 |
| cg26680047 | cg26870192 |
| cg26680520 | cg26872138 |
| cg26681211 | cg26873311 |
| cg26685735 | cg26877715 |
| cg26691604 | cg26878816 |
| cg26705425 | cg26881527 |

TABLE I-continued

Pan Cancer Panel

| | |
|---|---|
| cg26886307 | cg27037103 |
| cg26886972 | cg27040423 |
| cg26887632 | cg27041875 |
| cg26891924 | cg27042000 |
| cg26892444 | cg27046492 |
| cg26896668 | cg27051954 |
| cg26899113 | cg27052403 |
| cg26904700 | cg27056599 |
| cg26904914 | cg27060622 |
| cg26908611 | cg27061115 |
| cg26908755 | cg27062573 |
| cg26909954 | cg27062617 |
| cg26910092 | cg27063138 |
| cg26912242 | cg27064266 |
| cg26912984 | cg27066284 |
| cg26915774 | cg27068170 |
| cg26917673 | cg27068490 |
| cg26918442 | cg27070869 |
| cg26919818 | cg27072012 |
| cg26922444 | cg27072749 |
| cg26923908 | cg27073079 |
| cg26924294 | cg27078812 |
| cg26928603 | cg27080194 |
| cg26929012 | cg27080211 |
| cg26929348 | cg27082486 |
| cg26932552 | cg27084026 |
| cg26933063 | cg27084903 |
| cg26942943 | cg27085904 |
| cg26943708 | cg27086020 |
| cg26948603 | cg27086773 |
| cg26953462 | cg27087057 |
| cg26954625 | cg27088830 |
| cg26955196 | cg27090492 |
| cg26957677 | cg27093143 |
| cg26958597 | cg27099166 |
| cg26958806 | cg27099274 |
| cg26963029 | cg27099500 |
| cg26966630 | cg27101125 |
| cg26966707 | cg27108362 |
| cg26967167 | cg27109877 |
| cg26967579 | cg27111970 |
| cg26968387 | cg27112897 |
| cg26970841 | cg27116061 |
| cg26970847 | cg27116819 |
| cg26972058 | cg27116888 |
| cg26973488 | cg27117639 |
| cg26982364 | cg27121584 |
| cg26984626 | cg27123533 |
| cg26986911 | cg27123665 |
| cg26987855 | cg27125972 |
| cg26988146 | cg27128984 |
| cg26988215 | cg27133864 |
| cg26988406 | cg27134223 |
| cg26988692 | cg27136241 |
| cg26988895 | cg27138195 |
| cg26990660 | cg27139933 |
| cg26992213 | cg27140220 |
| cg26995744 | cg27143938 |
| cg26995992 | cg27147871 |
| cg26998900 | cg27151812 |
| cg26999505 | cg27154391 |
| cg27002185 | cg27162464 |
| cg27003849 | cg27164044 |
| cg27004639 | cg27166527 |
| cg27009208 | cg27173322 |
| cg27011620 | cg27175294 |
| cg27014927 | cg27178940 |
| cg27015174 | cg27180880 |
| cg27016990 | cg27182172 |
| cg27018185 | cg27192597 |
| cg27023953 | cg27194921 |
| cg27025752 | cg27197380 |
| cg27028168 | cg27199872 |
| cg27029179 | cg27204739 |
| cg27030612 | cg27209110 |
| cg27031632 | cg27212234 |
| cg27032142 | cg27213352 |
| cg27036581 | cg27220968 |

TABLE I-continued

Pan Cancer Panel

| |
|---|
| cg27222172 |
| cg27223727 |
| cg27225570 |
| cg27229407 |
| cg27230038 |
| cg27233989 |
| cg27240775 |
| cg27242945 |
| cg27243389 |
| cg27244585 |
| cg27249178 |
| cg27250841 |
| cg27253670 |
| cg27254295 |
| cg27257566 |
| cg27258025 |
| cg27258933 |
| cg27266382 |
| cg27269940 |
| cg27275523 |
| cg27276115 |
| cg27279904 |
| cg27286572 |
| cg27293549 |
| cg27295197 |
| cg27295781 |
| cg27299538 |
| cg27303430 |
| cg27304043 |
| cg27304516 |
| cg27306119 |
| cg27307206 |
| cg27308557 |
| cg27310163 |
| cg27311227 |
| cg27313572 |
| cg27315243 |
| cg27319192 |
| cg27323154 |
| cg27326642 |
| cg27326687 |
| cg27326823 |
| cg27327588 |
| cg27331401 |
| cg27333693 |
| cg27335720 |
| cg27336178 |
| cg27338377 |
| cg27339550 |
| cg27340350 |
| cg27346528 |
| cg27347140 |
| cg27351780 |
| cg27352765 |
| cg27355739 |
| cg27358097 |
| cg27359731 |
| cg27360003 |
| cg27361727 |
| cg27362103 |
| cg27362222 |
| cg27363741 |
| cg27364874 |
| cg27371984 |
| cg27372898 |
| cg27375072 |
| cg27380218 |
| cg27380819 |
| cg27382164 |
| cg27383277 |
| cg27386292 |
| cg27388983 |
| cg27391396 |
| cg27392850 |
| cg27395666 |
| cg27395939 |
| cg27405644 |
| cg27405960 |
| cg27410952 |
| cg27412987 |
| cg27413430 |
| cg27417717 |
| cg27418586 |
| cg27420520 |
| cg27421939 |
| cg27422496 |
| cg27425719 |
| cg27425996 |
| cg27430961 |
| cg27432847 |
| cg27433451 |
| cg27434954 |
| cg27434993 |
| cg27436264 |
| cg27437806 |
| cg27443310 |
| cg27445400 |
| cg27447053 |
| cg27447689 |
| cg27447868 |
| cg27448015 |
| cg27449131 |
| cg27449352 |
| cg27451672 |
| cg27453606 |
| cg27457941 |
| cg27462418 |
| cg27464311 |
| cg27465275 |
| cg27465717 |
| cg27466237 |
| cg27469783 |
| cg27475076 |
| cg27476262 |
| cg27476576 |
| cg27478700 |
| cg27479418 |
| cg27482605 |
| cg27486637 |
| cg27487839 |
| cg27492749 |
| cg27496650 |
| cg27502066 |
| cg27504805 |
| cg27506082 |
| cg27506462 |
| cg27507700 |
| cg27511208 |
| cg27511255 |
| cg27517702 |
| cg27519691 |
| cg27525037 |
| cg27530629 |
| cg27533019 |
| cg27534281 |
| cg27536453 |
| cg27538026 |
| cg27545919 |
| cg27546065 |
| cg27546736 |
| cg27546949 |
| cg27549834 |
| cg27552287 |
| cg27555382 |
| cg27558479 |
| cg27558594 |
| cg27559724 |
| cg27560922 |
| cg27564875 |
| cg27565366 |
| cg27565555 |
| cg27569040 |
| cg27569822 |
| cg27576755 |
| cg27577527 |
| cg27579532 |

TABLE I-continued

Pan Cancer Panel cg27584828
cg27586581
cg27586588
cg27591375
cg27594756
cg27597110
cg27599958
cg27604626
cg27606464
cg27607338
cg27612364
cg27619163
cg27627570
cg27629771
cg27632050
cg27633530
cg27635394
cg27636310
cg27637930
cg27637948
cg27638597
cg27641141
cg27646469
cg27647384
cg27650778
cg27654641
cg27655921
cg27658416
cg27659841
cg27665925

TABLE II

CRC Panel

| | | | | | |
|---|---|---|---|---|---|
| cg20295442 | cg20463526 | cg26122980 | cg09822538 | cg26212877 | cg20560075 |
| cg16601494 | cg27555582 | cg10864878 | cg03384825 | cg22538054 | cg11017065 |
| cg13405887 | cg09022943 | cg19651223 | cg16476975 | cg17228900 | cg05527869 |
| cg01051310 | cg12348588 | cg20329153 | cg02970696 | cg02259324 | cg15778437 |
| cg07703462 | cg25088758 | cg04537567 | cg17222500 | cg15490715 | cg20219457 |
| cg16300300 | cg11979589 | cg05051043 | cg12940822 | cg01563031 | cg22065614 |
| cg13024709 | cg15467646 | cg18120376 | cg19939997 | cg19824907 | cg18683604 |
| cg07188591 | cg14175690 | cg15658945 | cg01938650 | cg20556517 | cg13726682 |
| cg06952671 | cg06913330 | cg22834653 | cg05046525 | cg17035091 | cg03419885 |
| cg10512745 | cg03976877 | cg09667303 | cg03401096 | cg01883425 | cg17287235 |
| cg02173749 | cg11501438 | cg04897742 | cg14236735 | cg11855526 | cg17768491 |
| cg09498146 | cg25730685 | cg10236452 | cg04184836 | cg04198308 | cg10362542 |
| cg14348439 | cg17470837 | cg11281641 | cg17698295 | cg11666087 | cg18587340 |
| cg25798987 | cg07976064 | cg13101087 | cg09975620 | cg23217126 | cg10457056 |
| cg22623967 | cg08430489 | cg09740671 | cg02043600 | cg24392818 | cg25975712 |
| cg03225817 | cg26820055 | cg18638914 | cg00421139 | cg21672843 | cg15384598 |
| cg18884037 | cg01419567 | cg13554086 | cg07974511 | cg07700514 | cg23272632 |
| cg16993043 | cg01394819 | cg23300368 | cg16556906 | cg12816961 | cg01947130 |
| cg02604524 | cg24487076 | cg06528267 | cg21938148 | cg03356747 | cg16334314 |
| cg20864608 | cg03640756 | cg13223402 | cg04125371 | cg05209770 | cg00843236 |
| cg00662647 | cg20079899 | cg17029156 | cg08558397 | cg08452658 | cg01261798 |
| cg04904331 | cg03571927 | cg08189989 | cg15699267 | cg04790084 | cg10058779 |
| cg16918905 | cg27200446 | cg22879515 | cg16638385 | cg02511156 | |
| cg02455397 | cg27442308 | cg20631014 | cg00817367 | cg22474464 | cg09802835 |
| cg22871668 | cg19875368 | cg14098681 | cg15779837 | cg08354093 | cg14794428 |
| cg15825786 | cg12417685 | cg04272632 | cg21039708 | cg24033330 | cg14485004 |
| cg13690864 | cg20012008 | cg03133266 | cg26274580 | cg20686234 | cg03957481 |
| cg04718428 | cg14473327 | cg15207742 | cg12907379 | cg12042659 | cg05374412 |
| cg16676492 | cg03755177 | cg21314480 | cg16230141 | cg10453425 | cg26495865 |
| cg05522774 | cg10293925 | cg10002178 | cg02583633 | cg02539855 | cg20443778 |
| cg25012919 | cg18786873 | cg15461516 | cg13867865 | cg09239744 | cg09155997 |
| cg09462445 | cg14648916 | cg13557668 | cg09461837 | cg14936269 | cg23697417 |
| cg05171952 | cg14409941 | cg11428724 | cg23932491 | cg05344430 | cg19497031 |
| cg16520288 | cg09495977 | cg14568217 | cg21329599 | cg27111463 | cg05758094 |
| cg21875802 | cg18355902 | cg06997381 | cg08434234 | cg19178853 | cg07017374 |
| cg02842227 | cg15424739 | cg21176643 | cg23215729 | cg10096161 | cg02483484 |
| cg11859584 | cg02174225 | cg06651311 | cg20450979 | cg06266613 | cg15286044 |
| cg17771605 | cg09683824 | cg16899920 | cg07821427 | cg12859211 | cg12686317 |
| cg00625334 | cg22284043 | cg01878345 | cg26990102 | cg24686074 | cg16332256 |
| cg04453180 | cg24521633 | cg16584573 | cg05178576 | cg22878622 | cg16729832 |
| cg27264249 | cg19752627 | cg24773418 | cg01419831 | cg18646207 | cg16514543 |
| cg18762727 | cg03257575 | cg13776340 | cg16474297 | cg03698948 | cg02058731 |
| cg16482474 | cg27364741 | cg13562911 | cg24305584 | cg15261247 | cg26365854 |
| cg11878331 | cg04058593 | cg18607529 | cg06630204 | cg27101125 | cg14725151 |
| cg18759960 | cg07057177 | cg26615127 | cg07068756 | cg11253514 | cg24886267 |
| cg27317433 | cg24262066 | cg18623980 | cg11677857 | cg02869459 | cg13619824 |
| cg22138430 | cg14657517 | cg01579950 | cg06172475 | cg16307705 | cg23201032 |
| cg14535068 | cg07752026 | cg24403845 | cg01501819 | cg27493301 | cg00114029 |
| cg26739280 | cg26818735 | cg21901946 | cg19320476 | cg26684946 | cg23359394 |
| cg27510832 | cg00100121 | cg26834169 | cg00017221 | cg06319822 | cg15409931 |
| cg24876960 | cg07078225 | cg05562381 | cg04156369 | cg07060006 | cg16485558 |
| cg07495363 | cg17386213 | cg07283152 | cg11689407 | cg13432708 | cg24599249 |
| cg25767985 | cg21678377 | cg13464448 | cg18406197 | cg11107669 | cg16366473 |
| cg07628404 | cg14256587 | cg14667871 | cg23719318 | cg11732619 | cg11821817 |
| cg14965220 | cg05228284 | cg04171539 | cg13368519 | cg07627556 | cg20593611 |

TABLE II-continued

CRC Panel

| | | | | | |
|---|---|---|---|---|---|
| cg17847723 | cg11881754 | cg06393563 | cg19769760 | cg17483297 | cg23978504 |
| cg19924619 | cg17263061 | cg04100696 | cg13652513 | cg12865552 | cg26156687 |
| cg07283114 | cg02966153 | cg09912350 | cg20665002 | cg08157228 | cg26232818 |
| cg21583226 | cg15344220 | cg08460041 | cg21325154 | cg14218042 | cg03142956 |
| cg13670601 | cg05332960 | cg26892444 | cg25184481 | cg04689080 | cg24134479 |
| cg26547924 | cg23462956 | cg13882278 | cg19003797 | cg11771234 | cg04245057 |
| cg13713293 | cg02650317 | cg01755562 | cg10036918 | cg26029736 | cg05710997 |
| cg15867939 | cg20168412 | cg12424694 | cg04549333 | cg22604123 | cg11912330 |
| cg23649435 | cg06752260 | cg16332936 | cg18122419 | cg19631064 | cg27541454 |
| cg08708747 | cg09849405 | cg00854242 | cg10417567 | cg01138867 | cg07600871 |
| cg01278387 | cg01056653 | cg23820770 | cg05141147 | cg01505767 | cg03324821 |
| cg20611276 | cg27308329 | cg24870497 | cg06978388 | cg19697475 | cg23091984 |
| cg12210736 | cg16741041 | cg26802291 | cg09571420 | cg10173182 | cg08386091 |
| cg13353699 | cg06499647 | cg10188823 | cg03336086 | cg16440629 | cg22841810 |
| cg27100436 | cg25964032 | cg09010323 | cg09642925 | cg08095852 | cg01135780 |
| cg24034005 | cg06500120 | cg08105352 | cg20949845 | cg11953272 | cg13025668 |
| cg16882226 | cg26686277 | cg04130185 | cg06738356 | cg13796804 | cg08311610 |
| cg11161828 | cg14018731 | cg17958315 | cg06554120 | cg07003632 | cg08726248 |
| cg27513573 | cg17457560 | cg26464221 | cg13689003 | cg11733675 | cg12850078 |
| cg16589214 | cg16434547 | cg02979001 | cg14602341 | cg21472506 | cg09295081 |
| cg01616178 | cg12804010 | cg27018185 | cg00069860 | cg12993163 | cg20401551 |
| cg22898797 | cg05127821 | cg07244354 | cg13643376 | cg08042975 | cg16236766 |
| cg00592781 | cg17507573 | cg10031614 | cg20232102 | cg22723056 | cg06480695 |
| cg22147084 | cg02629281 | cg04242021 | cg09628601 | cg17898329 | cg14059768 |
| cg16921310 | cg13742526 | cg08793877 | cg05291069 | cg05624214 | cg17838029 |
| cg23048481 | cg23226129 | cg23582408 | cg09424526 | cg15963563 | cg05372242 |
| cg16202470 | cg24037897 | cg17846334 | cg24899571 | cg11911648 | cg25987194 |
| cg18147366 | cg25649038 | cg25905674 | cg16478774 | cg11775528 | cg04548336 |
| cg07491495 | cg09441363 | cg03132773 | cg21233688 | cg13448814 | cg20642710 |
| cg18013519 | cg19519310 | cg05619587 | cg04215672 | cg11021744 | cg26105156 |
| cg26298979 | cg02370417 | cg23657299 | cg24461964 | cg14088357 | cg22403293 |
| cg05812269 | cg07559273 | cg21098557 | cg10903451 | cg07701191 | cg26917673 |
| cg01108106 | cg23288962 | cg09807215 | cg12745764 | cg07204550 | cg20276585 |
| cg08592707 | cg23108709 | cg12661206 | cg15927682 | cg07455757 | cg08943428 |
| cg13911723 | cg13482432 | cg06371502 | cg22685369 | cg08867893 | cg26306372 |
| cg00745606 | cg14867604 | cg20803857 | cg15245095 | cg11642382 | cg15363487 |
| cg13207797 | cg13768269 | cg26858268 | cg22260952 | cg20072442 | cg01154046 |
| cg13443605 | cg08172445 | cg25616216 | cg16303846 | cg06164660 | cg01003015 |
| cg27047243 | cg11497952 | cg18645133 | cg12510981 | cg27326452 | cg27313572 |
| cg07482935 | cg26515460 | cg07721203 | cg08511440 | cg20650138 | cg23991622 |
| cg10254000 | cg26077100 | cg14042851 | cg00024472 | cg15462174 | cg02746869 |
| cg06256858 | cg13914094 | cg20772101 | cg13258563 | cg20536716 | cg18514820 |
| cg15991072 | cg22685245 | cg02825977 | cg09342766 | cg21864259 | cg20319091 |
| cg12630714 | cg06959514 | cg15212349 | cg27557378 | cg02655972 | cg20018469 |
| cg04205107 | cg26729197 | cg11257429 | cg26985666 | cg18996590 | cg14898116 |
| cg08700032 | cg12639324 | cg04679031 | cg16899351 | cg17293936 | cg27147718 |
| cg17498773 | cg25130672 | cg17999686 | cg16482314 | cg18800085 | cg01466678 |
| cg06714320 | cg03825010 | cg07729537 | cg22396057 | cg02975107 | cg11306587 |
| cg15602740 | cg07085962 | cg04282138 | cg26370226 | cg15803122 | cg13031432 |
| cg22587479 | cg06530338 | cg12874092 | cg25165358 | cg01349858 | cg08791131 |
| cg18175808 | cg11244340 | cg05338433 | cg13420848 | cg26072759 | cg02040433 |
| cg15852572 | cg23964057 | cg14765646 | cg14517743 | cg06270802 | cg00984694 |
| cg16086373 | cg12097080 | cg27230784 | cg11163901 | cg10779644 | cg04797985 |
| cg00266322 | cg16341592 | cg27498114 | cg11109374 | cg05627441 | cg00262031 |
| cg26444995 | cg20686479 | cg16805150 | cg04028634 | cg03840467 | cg06650115 |
| cg09324514 | cg12584684 | cg17108819 | cg18488855 | cg02829680 | cg15343461 |
| cg06841192 | cg04610224 | cg07852757 | cg20209009 | cg02576219 | cg11278204 |
| cg07622696 | cg08247376 | cg04190807 | cg01626326 | cg04819760 | cg05245861 |
| cg00758881 | cg05006349 | cg00095976 | cg11189837 | cg10918202 | cg15749748 |
| cg10383447 | cg13238990 | cg05961935 | cg24723331 | cg12975779 | cg07224914 |
| cg08092105 | cg02588107 | cg03696327 | cg25622036 | cg08145617 | cg08828403 |
| cg00581595 | cg02361557 | cg07952047 | cg07034660 | cg25602490 | cg00557354 |
| cg04194840 | cg11698244 | cg27376683 | cg18255353 | cg06223466 | cg04882995 |
| cg12973591 | cg01258201 | cg08521987 | cg22370480 | cg05203877 | cg11137615 |
| cg20230721 | cg13631916 | cg00584713 | cg19025435 | cg00279790 | cg14101302 |
| cg24531255 | cg24851364 | cg14470398 | cg04838988 | cg21252914 | cg14361033 |
| cg17338208 | cg20915632 | cg11724516 | cg10205753 | cg26215967 | cg04279973 |
| cg14775114 | cg02756106 | cg26256401 | cg06078334 | cg05874561 | cg11226148 |
| cg16934178 | cg22289831 | cg00238770 | cg10756127 | cg12644264 | cg05588496 |
| cg22441533 | cg16098981 | cg15802898 | cg21008602 | cg05525743 | cg21187769 |
| cg18302726 | cg05238517 | cg13769223 | cg19265970 | cg13721429 | cg03038003 |
| cg13096260 | cg02030008 | cg12169536 | cg02327123 | cg06412358 | cg22149516 |
| cg08979737 | cg24280540 | cg05932408 | cg23282559 | cg02795515 | cg03091010 |
| cg16935295 | cg18565783 | cg16120828 | cg13761440 | cg05235761 | cg22932815 |
| cg07146119 | cg05293738 | cg26341102 | cg14449051 | cg04626565 | cg08085954 |
| cg20594401 | cg02707869 | cg07005294 | cg00053373 | cg19918758 | cg23089549 |
| cg06531379 | cg04336836 | cg15308062 | cg08372619 | cg01090834 | cg09547173 |
| cg14657834 | cg15087147 | cg22975913 | cg01978558 | cg13565575 | cg08739576 |

TABLE II-continued

CRC Panel

| | | | | | |
|---|---|---|---|---|---|
| cg24424545 | cg13485685 | cg12478381 | cg27034576 | cg19123296 | cg05082965 |
| cg07748540 | cg18233786 | cg20513548 | cg25664438 | cg07071978 | cg10556384 |
| cg23749856 | cg18237607 | cg06639332 | cg13346411 | cg09553380 | cg22583333 |
| cg25299895 | cg01946574 | cg05142765 | cg05484788 | cg22871002 | cg07135732 |
| cg02500300 | cg20250080 | cg01562349 | cg02855633 | cg19439399 | cg10143067 |
| cg13643796 | cg02139871 | cg10160975 | cg19819145 | cg15647515 | cg09479015 |
| cg10416527 | cg03004999 | cg21219996 | cg19523085 | cg17883458 | cg17475987 |
| cg03352776 | cg14374754 | cg17350006 | cg18736279 | cg12741994 | cg06976395 |
| cg01259029 | cg06459000 | cg26525127 | cg07557790 | cg03912954 | cg01791410 |
| cg07991951 | cg06124528 | cg02732202 | cg24488602 | cg03802461 | cg04207385 |
| cg13436799 | cg03774520 | cg24141863 | cg02753362 | cg18220921 | cg18496247 |
| cg17304222 | cg20341985 | cg13869401 | cg04534926 | cg08980837 | cg25468723 |
| cg18714412 | cg24813176 | cg26756083 | cg01190692 | cg22130145 | cg22376688 |
| cg22675486 | cg06498720 | cg00057434 | cg10694781 | cg11292593 | cg22795590 |
| cg24354581 | cg01018701 | cg01466288 | cg00651020 | cg27155954 | cg18928153 |
| cg13285637 | cg04144226 | cg13767755 | cg25923450 | cg25214789 | cg23589617 |
| cg16793187 | cg14242042 | cg05310249 | cg02489958 | cg02136132 | cg05991314 |
| cg20052751 | cg16673106 | cg26985446 | cg14455998 | cg10737195 | cg24732574 |
| cg06392318 | cg13652557 | cg01463565 | cg19096571 | cg24862668 | cg06025835 |
| cg03350814 | cg01775414 | cg09198448 | cg25302419 | cg17968795 | cg03766620 |
| cg27573591 | cg02908587 | cg27138584 | cg00854166 | cg26756506 | cg01001098 |
| cg06357925 | cg01826682 | cg05273205 | cg25584626 | cg19540689 | cg07749724 |
| cg24588375 | cg20985635 | cg00752628 | cg02875118 | cg25999867 | cg24805239 |
| cg23040064 | cg19635869 | cg01134282 | cg15565872 | cg05423529 | cg24593272 |
| cg17434309 | cg00235933 | cg25749267 | cg06166932 | cg01582473 | cg19661610 |
| cg22015128 | cg25249613 | cg07994622 | cg07765161 | cg04856292 | cg18379780 |
| cg04010684 | cg09717526 | cg25990363 | cg11399100 | cg05245226 | cg07997493 |
| cg22794494 | cg13843613 | cg13376598 | cg22849427 | cg14670435 | cg16465502 |
| cg22349506 | cg06384463 | cg23475625 | cg26832142 | cg24709718 | cg11195082 |
| cg03725852 | cg01693063 | cg20956278 | cg26393713 | cg22679003 | cg06374307 |
| cg10571951 | cg09276565 | cg14598976 | cg12158272 | cg25922637 | cg25542041 |
| cg06457317 | cg12278754 | cg04802694 | cg04043591 | cg24368902 | cg13045310 |
| cg02084669 | cg02648941 | cg14956197 | cg21604803 | cg12144689 | cg15496063 |
| cg25834415 | cg17491091 | cg01733438 | cg23912429 | cg05725404 | cg27496965 |
| cg19575759 | cg10290373 | cg05729480 | cg11973177 | cg04484415 | cg01329309 |
| cg26916297 | cg15577178 | cg21437548 | cg26983469 | cg11640773 | cg26777303 |
| cg13870510 | cg06085011 | cg18853199 | cg12155165 | cg27102864 | cg23858558 |
| cg27103296 | cg11235663 | cg25810857 | cg13414916 | cg01084435 | cg18719750 |
| cg13875133 | cg10737663 | cg11468193 | cg26063719 | cg05222604 | cg25070637 |
| cg11897314 | cg08804846 | cg10857221 | cg14260889 | cg00785042 | cg14538332 |
| cg14868994 | cg27372162 | cg25715035 | cg19170009 | cg05129348 | cg04261408 |
| cg03247892 | cg24482234 | cg20631104 | cg00687686 | cg08229468 | cg14625631 |
| cg01375976 | cg11117108 | cg02621694 | cg04942472 | cg09217878 | cg10292139 |
| cg02101773 | cg23067351 | cg01049530 | cg05469759 | cg26514728 | cg16673702 |
| cg03167496 | cg03954411 | cg01941671 | cg08384171 | cg18024479 | cg03276479 |
| cg17503456 | cg13165472 | cg05718036 | cg04005075 | cg19784477 | cg23356017 |
| cg09639622 | cg17870792 | cg26699569 | cg16812519 | cg22799321 | cg27517823 |
| cg21527132 | cg17965926 | cg01285706 | cg26824423 | cg23141855 | cg24862252 |
| cg02134353 | cg03840647 | cg05069909 | cg04858398 | cg23686014 | cg10303967 |
| cg07501233 | cg14424049 | cg07523148 | cg05622686 | cg26739865 | cg18030776 |
| cg01578987 | cg00723271 | cg07321467 | cg10146880 | cg14377593 | cg14942501 |
| cg05528102 | cg12566138 | cg19675063 | cg05201312 | cg15649801 | cg26842303 |
| cg26988406 | cg10886442 | cg10790685 | cg02036364 | cg10539069 | cg15980656 |
| cg08937573 | cg09470640 | cg23821329 | cg01733271 | cg24084681 | cg22137815 |
| cg05931096 | cg23214267 | cg02236650 | cg08367638 | cg07380959 | cg14830748 |
| cg02486351 | cg14046986 | cg19111999 | cg02830555 | cg03333330 | cg16962683 |
| cg00187933 | cg22082709 | cg20198108 | cg04808179 | cg09558850 | cg14408978 |
| cg19207487 | cg09679945 | cg06460869 | cg26668272 | cg19854521 | cg00446722 |
| cg16404040 | cg11989011 | cg05151811 | cg05333442 | cg13328713 | cg12190613 |
| cg08614481 | cg03167951 | cg08918274 | cg01343363 | cg19103770 | |
| cg06254440 | cg15090727 | cg00146951 | cg27113419 | cg07603382 | |

The selection of a hypermethylated site according to the present method is defined as follows. For each clinical sample of a specific cancer type in a database, e.g., The Cancer Genome Atlas, the methylation level is determined for each methylation site i from a starting set of sites as described in the preceding paragraph. For instance, for each clinical sample from a set of colon adenocarcinoma samples in The Cancer Genome Atlas, the methylation state at each of the CpG sites listed in Tables I and II is determined, and the mean methylation level at each site i calculated as described elsewhere in this application. In some embodiments, the methylation level can be determined as the fraction of 'C' bases out of 'C'+'U' total bases at a target CpG site i following the bisulfite treatment. In other embodiments, the methylation level can be determined as the fraction of 'C' bases out of 'C'+'T' total bases at site i following the bisulfite treatment and subsequent nucleic acid amplification. The mean methylation level at each site is then evaluated to determine if one or more threshold is met. In some embodiments, a threshold selects those sites having the highest-ranked mean methylation values for a specific cancer type. For example, the threshold can be those sites having a mean methylation level that is the top 50%, the top 40%, the top 30%, the top 20%, the top 10%, the top 5%, the top 4%, the top 3%, the top 2%, or the top 1% of mean methylation levels across all sites i tested for a specific cancer type, e.g., colon adenocarcinoma. Alternatively, the threshold can be those sites having a mean methylation level that is at a percentile rank greater than or equivalent to 50, 60, 70, 80, 90, 95, 96, 97, 98, or 99. In other embodiments, a threshold can be based on the absolute value of the mean methylation level. For instance, the threshold can be those sites having a mean methylation level that is greater than 99%, greater than 98%, greater than 97%, greater than 96%, greater than 95%, greater than 90%, greater than 80%, greater than 70%, greater than 60%, greater than 50%, greater than 40%, greater than 30%, greater than 20%, greater than 10%, greater than 9%, greater than 8%, greater than 7%, greater than 6%, greater than 5%, greater than 4%, greater than 3%, or greater than 2%. The relative and absolute thresholds can be applied to the mean methylation level at each site i individually or in combination. As an illustration of a combined threshold application, one may select a subset of sites that are in the top 3% of all sites tested by mean methylation level and also have an absolute mean methylation level of greater than 6%. The result of this selection process is a plurality of lists, one for each cancer type, of specific hypermethylated sites (e.g., CpG sites) that are considered the most informative for that cancer type. These lists are then used to identify or classify a test genomic DNA sample from a test organism, i.e. to determine whether the test organism has a specific cancer type.

In the next step of the present method, a test genomic DNA sample from a test organism is analyzed by determining the methylation levels at each site i on the list of hypermethylated sites for each cancer type, and these methylation levels for each site are then averaged to calculate the average methylation level across the hypermethylated sites for each cancer type. For instance, for each hypermethylated site i for colon adenocarcinoma, the methylation level at each site i on the list of hypermethylated sites for colon adenocarcinoma is determined, and these methylation levels are then averaged to provide a single average methylation level. This process is repeated using the previously defined lists of hypermethylated sites for each of the cancer types, and results in a set of average methylation levels, each corresponding to a different cancer type. The average methylation levels are then ranked from lowest to highest. The cancer type corresponding to the highest average methylation level is considered to be associated with the test genomic DNA, i.e. the cancer type is deemed to be present in the test organism. It is understood that the normalized methylation difference or z-score also can be used in the present method instead of the methylation level at each CpG site.

For cancer screening or detection, the determination of a methylation level of a plasma (or other biologic) sample can be used in conjunction with other modalities for cancer screening or detection such as prostate specific antigen measurement (e.g. for prostate cancer), carcinoembryonic antigen (e.g. for colorectal carcinoma, gastric carcinoma, pancreatic carcinoma, lung carcinoma, breast carcinoma, medullary thyroid carcinoma), alpha fetoprotein (e.g. for liver cancer or germ cell tumors) and CA19-9 (e.g. for pancreatic carcinoma).

Useful methylation sites that can be detected in a method set forth herein, for example, to evaluate cancer are include those present in the Cancer Genome Atlas (see, for example, Cancer Genome Atlas Research Network et al., *Nature Genetics* 45:1113-1120 (2013)) or the selected CpG sites of the Pan Cancer Panel set forth in Table I (the listed methylation sites are from Genome Build 37). Further examples of CpG sites that can be useful, for example, to identify or monitor colorectal cancer, are described in Worthley et al. *Oncogene* 29, 1653-1662 (2010) or set forth in Table II (the listed methylation sites are from Genome Build 37). Useful methylation markers for detection of ovarian cancer are set forth in US Pat. App. Pub. No. 2008/0166728 A1, which is incorporated herein by reference. All or a subset of the markers set forth herein and/or listed in a reference above can be used in a method set forth herein. For example, at least 10, 25, 50, 100, $1\times10^3$, $1\times10^4$ or more of the markers can be used.

Analysis of the methylation, prognosis or diagnosis information derived from a method set forth herein can conveniently be performed using various computer executed algorithms and programs. Therefore, certain embodiments employ processes involving data stored in or transferred through one or more computer systems or other processing systems. Embodiments of the invention also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as a "cloud." A particularly useful cloud is one that is configured and administered to store and analyze genetic data such as the BaseSpace™ service (Illumina, Inc. San Diego Calif.), or cloud services described in US Pat. App. Pub. Nos. 2013/0275486 A1 or 2014/0214579 A1 (each of which is incorporated herein by reference). Examples of program instructions include both machine code, such as produced by a compiler, and files containing higher level code that may be executed by the computer using an interpreter.

In some embodiments, the data or information employed in the disclosed methods and apparatus is provided in an electronic format. Such data or information may include reads derived from a nucleic acid sample, reference sequences, methylation states, patterns of methylation states, methylation difference scores, normalized methylation difference scores, aggregate coverage-weighted normalized methylation difference scores, methylation scores, coverage-weighted methylation scores, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In addition, certain embodiments relate to tangible and/or non-transitory computer readable media or computer program products that include instructions and/or data (including data structures) for performing various computer-implemented operations. One or more of the steps of a method set forth herein can be carried out by a computer program that is present in tangible and/or non-transitory computer readable media, or carried out using computer hardware.

For example, a computer program product is provided and it comprises a non-transitory computer readable medium on which is provided program instructions for steps of (a) obtaining a test data set that includes (i) methylation states for a plurality of sites from test genomic DNA from at least one test organism, and (ii) coverage at each of the sites for detection of the methylation states; (b) obtaining methylation states for the plurality of sites in reference genomic DNA from one or more reference individual organisms, (c) determining, for each of the sites, the methylation difference between the test genomic DNA and the reference genomic DNA, thereby providing a normalized methylation difference for each site; (d) weighting the normalized methylation difference for each site by the coverage at each of the sites, thereby determining an aggregate coverage-weighted normalized methylation difference score, and (e) storing or transmitting the aggregate coverage-weighted normalized methylation difference score.

Methods disclosed herein can also be performed using a computer processing system which is adapted or configured to perform a method for identifying methylation states or other characteristics of nucleic acids. Thus, in one embodiment, the invention provides a computer processing system which is adapted or configured to perform a method as described herein. In one embodiment, the apparatus comprises a nucleic acid detection device, such as a nucleic acid sequencing device, adapted or configured to determine methylation states and/or other characteristics of nucleic acids. The apparatus may also include components for processing a sample from a test organism and/or reference organism. Such components are described elsewhere herein.

Nucleic acid sequence, methylation state, methylation pattern, or other data, can be input into a computer or stored on a computer readable medium either directly or indirectly. In one embodiment, a computer system is directly coupled to a nucleic acid detection device (e.g. sequencing device) that determines methylation states of nucleic acids from samples. Data or other information from such tools are provided via interface in the computer system. Alternatively, the methylation data processed by systems are provided from a data storage source such as a database or other repository. Once available to the processing apparatus, a memory device or mass storage device buffers or stores, at least temporarily, methylation states or other characteristics of the nucleic acids. In addition, the memory device may store methylation differences, normalized methylation differences, aggregate weighted normalized methylation differences, methylation scores, or coverage-weighted methylation scores as described herein. The memory may also store various routines and/or programs for analyzing or presenting such information. Such programs/routines may include programs for performing statistical analyses, etc.

In one example, a user provides a sample to a nucleic acid sequencing apparatus. Data is collected and/or analyzed by the sequencing apparatus which is connected to a computer. Software on the computer allows for data collection and/or analysis. Data can be stored, displayed (e.g. via a monitor or other similar device), and/or sent to another location. The computer may be connected to the internet which is used to transmit data to a handheld device and/or cloud environment utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to, a building, city, state, country or continent.

In some embodiments, the methods also include collecting data regarding a plurality of polynucleotide sequences (e.g., reads, tags and/or methylation states) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data that has been collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following: reads obtained by sequencing nucleic acids in a test sample, methylation states for sites in the nucleic acids, one or more reference genome or sequence, methylation difference score, normalized methylation difference score, aggregate coverage-weighted normalized methylation difference score, methylation score, or coverage-weighted methylation score as described herein.

These various types of data may be obtained, stored, transmitted, analyzed, and/or manipulated at one or more locations using distinct apparatus. The processing options span a wide spectrum. Toward one end of the spectrum, all or much of this information is stored and used at the location where the test sample is processed, e.g., a doctor's office or other clinical setting. Toward another extreme, the sample is obtained at one location, it is processed (e.g. prepared, detected or sequenced) at a second location, data is analyzed (e.g. sequencing reads are aligned) and methylation characteristics are determined at a third location (or several locations), and diagnoses, recommendations, and/or plans are prepared at a fourth location (or the location where the sample was obtained).

In various embodiments, the methylation data are generated on a nucleic acid detection apparatus (e.g. sequencing apparatus) and then transmitted to a remote site where they are processed to determine methylation characteristics. At this remote location, as an example, methylation difference score, normalized methylation difference score, aggregate coverage-weighted normalized methylation difference score, methylation score, or coverage-weighted methylation score can be determined. Also at the remote location, the methylation characteristics can be evaluated to make a prognostic or diagnostic determination.

Any one or more of these operations may be automated as described elsewhere herein. Typically, the detection of nucleic acids and the analyzing of sequence data will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to methylation detection may be performed include health practitioners' offices, clinics, patients' homes (where a sample processing apparatus or kit is provided), mobile health care vehicles, and facilities of nucleic acid analysis providers. Examples of locations where nucleic acid detection (e.g. sequencing) may be performed include health practitioners' offices, clinics, health practitioners' offices, clinics, patients' homes (where a sample sequencing apparatus and/or kit is provided), mobile health care vehicles, and facilities of nucleic acid analysis providers. The location where the nucleic acid detection takes place may be provided with a dedicated network connection for transmitting sequence data (typically reads) in an electronic format. Such connection may be wired or wireless and may be configured to send the data to a site where the data can be processed and/or aggregated prior to transmission to a processing site. Data aggregators can be maintained by health organizations such as Health Maintenance Organizations (HMOs).

The analyzing operations may be performed at any of the foregoing locations or alternatively at a further remote site dedicated to computation and/or the service of analyzing nucleic acid sequence data. Such locations include for example, clusters such as general purpose server farms, the facilities of a genetic analysis service business, and the like. In some embodiments, the computational apparatus employed to perform the analysis is leased or rented. The computational resources may be part of an internet accessible collection of processors such as processing resources colloquially known as the "cloud", examples of which are provided elsewhere herein. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., determination that the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, Internet sites accessible by computers, handheld devices, etc.

In some embodiments, the sample collection, sample processing, and methylation state detection operations are performed at a first location and the analyzing and deriving operation is performed at a second location. However, in some cases, the sample collection is collected at one location (e.g., a health practitioner's office or clinic) and the sample processing and methylation state detecting is performed at a different location that is optionally the same location where the analyzing and deriving take place.

In various embodiments, a sequence of the above-listed operations may be triggered by a user or entity initiating sample collection, sample processing and/or methylation state detection. After one or more of these operations have begun execution the other operations may naturally follow. For example, a nucleic acid sequencing operation may cause reads to be automatically collected and sent to a processing apparatus which then conducts, often automatically and possibly without further user intervention, the methylation state analysis and determination of methylation difference score, normalized methylation difference score, aggregate coverage-weighted normalized methylation difference score, methylation score, or coverage-weighted methylation score. In some implementations, the result of this processing operation is then automatically delivered, possibly with reformatting as a diagnosis, to a system component or entity that processes or reports the information to a health professional and/or patient. As explained, such information can also be automatically processed to produce a treatment, testing, and/or monitoring plan, possibly along with counseling information. Thus, initiating an early stage operation can trigger an end to end process in which the health professional, patient or other concerned party is provided with a diagnosis, a plan, counseling and/or other information useful for acting on a physical condition. This is accomplished even though parts of the overall system are physically separated and possibly remote from the location of, e.g., the sample collection and nucleic acid detection apparatus.

In some embodiments the results of a method set forth herein will be communicated to an individual by a genetic counselor, physician (e.g., primary physician, obstetrician, etc.), or other qualified medical professional. In certain embodiments the counseling is provided face-to-face, however, it is recognized that in certain instances, the counseling can be provided through remote access (e.g., via text, cell phone, cell phone app, tablet app, internet, and the like).

In some embodiments, disclosure of results to a medical professional or to a patient can be delivered by a computer system. For example, "smart advice" systems can be provided that in response to test results, instructions from a medical care provider, and/or in response to queries (e.g., from a patient) provide genetic counseling information. In certain embodiments the information will be specific to clinical information provided by the physician, healthcare system, and/or patient. In certain embodiments the information can be provided in an iterative manner. Thus, for example, the patient can provide "what if" inquiries and the system can return information such as diagnostic options, risk factors, timing, and implication of various outcomes.

In particular embodiments, the results or other information generated in a method set forth herein can be provided in a transitory manner (e.g., presented on a computer screen). In certain embodiments, the information can be provided in a non-transitory manner. Thus, for example, the information can be printed out (e.g., as a list of options and/or recommendations optionally with associated timing, etc.) and/or stored on computer readable media (e.g., magnetic media such as a local hard drive, a server, etc., optical media, flash memory, and the like).

It will be appreciated that typically such systems will be configured to provide adequate security such that patient privacy is maintained, e.g., according to prevailing standards in the medical field.

The foregoing discussion of genetic counseling is intended to be illustrative and not limiting. Genetic counseling is a well-established branch of medical science and incorporation of a counseling component with respect to the methods described herein is within the scope and skill of the practitioner. Moreover, it is recognized that as the field progresses, the nature of genetic counseling and associated information and recommendations is likely to alter.

Example I

Analytical Sensitivity of ctDNA Methylation-Based Cancer Detection Using Aggregate Normalized Coverage-Weighted Methylation Differences This example describes a highly sensitive assay for detecting methylation in circulating tumor DNA (ctDNA). Aberrant DNA methylation is a widespread phenomenon in cancer and may be among the earliest changes to occur during oncogenesis. The assay described in this example can be useful for cancer screening.

The general approach applied here includes targeted methylation sequencing for multiple CpG sites affected in cancer.

Technical challenges addressed by the approach include providing ultra-high sensitivity and specificity that benefits screening applications, providing a protocol for targeted methyl-seq from low input ctDNA, and providing bioinformatics algorithms for analysis of methylation levels across a large number of targeted sites.

Targeted Capture Probe Design

Two targeted methylation panels were developed. The Pan-Cancer Panel targets 9,921 affected CpG sites in 20 major cancer types as selected from The Cancer Genome Atlas Database. The CpG sites included in the Pan-Cancer Panel are listed in Table I. The CRC Panel targets 1,162 affected CpG sites in colorectal cancer. The CpG sites included in the CRC Panel are listed in Table II. The CpG sites listed in Table I and Table II refer to Genome Build 37.

The probe sequences for the CpG sites were selected from the Infinium HM450 array (Illumina, Inc., San Diego, Calif.). Design principles for the probes are shown in FIG. 1. Two probes were used for targets having greater than 4 CpG sites, including a completely methylated probe (having a G nucleotides that complements the C position of each CpG site) and completely unmethylated probe (having an A nucleotide that complements the U that is expected to result from bisulfite conversion of each of the C positions of a CpG site) as shown in FIG. 1. In contrast, only one probe was used for targets having 4 or fewer CpG sites (the probe includes degenerate nucleotide R, complementary to U or C, at the C position of each CpG site).

Isolation and Extraction of cfDNA from Plasma

Figure 2:
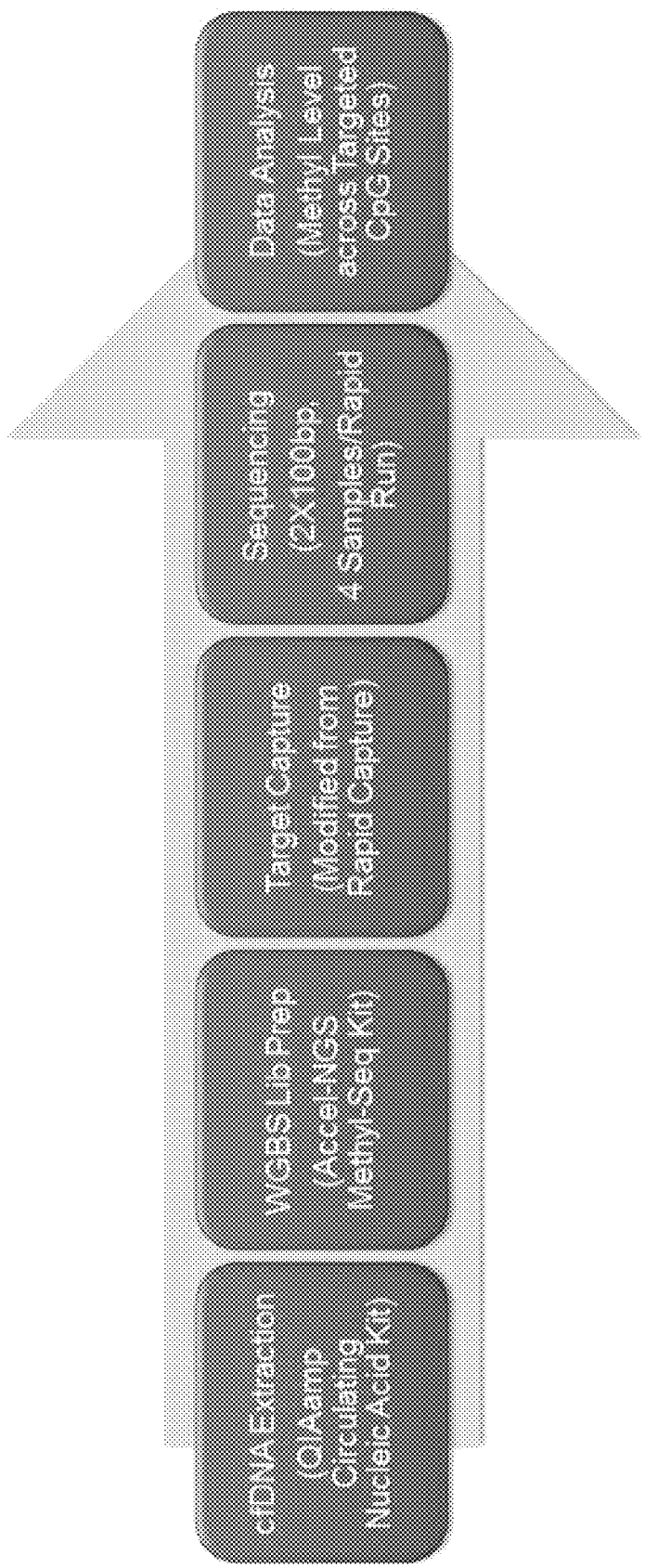
FIG. 2 shows a workflow for targeted circulating tumor DNA (ctDNA) methylation sequencing.

Plasma samples were obtained from human blood draws. Cell free DNA (cfDNA) was extracted using the QIAamp Circulating Nucleic Acid Kit (Qiagen, Hilden, Germany). Targeted ctDNA methylation sequencing was carried out according to the workflow shown in FIG. 2, and as set forth below in the context of evaluating titration and detection sensitivity.

Titration and Detection Sensitivity

NA12878 genomic DNA was purchased from Coriell Institute (Coriell Institute, Camden, N.J.), and LS1034 genomic DNA was purchased from ATCC (ATCC, Manassas, Va.). Genomic DNA was fragmented using Covaris M200 (Covaris, Woburn, Mass.) and size-selected to 130-250 bp using BluePippin (Sage Science, Beverly, Mass.) to simulate the size distribution of cfDNA. DNA quantification was performance using Quant-iT™ PicoGreen® dsDNA Assay Kit (ThermoFisher Scientific, Grand Island, N.Y.). 10%, 1%, or 0.1% LS1034 DNA was spiked into NA12878 DNA background to make the DNA mixtures. 30 ng of each mixture, 100% NA12878, or 100% LS1034 DNA was used in library preparation. Three replicated libraries were generated for each titration level. A set of six replicates of NA12878 was used as the baseline reference genome.

Extracted cfDNA or sheared and size-selected genomic DNA was bisulfite treated and purified using EZ DNA Methylation-Lightning Kit (Zymo Research, Irvine, Calif.).

Bisulfite-seq Libraries were prepared using the Accel-NGS® Methyl-Seq DNA Library Kit (Swift Biosciences, Ann Arbor, Mich.).

Targeted capture was carried out on the bisulfite-seq libraries using probes that were complementary to fragments having the CpG sites listed in Table I or Table II. Capture probes were synthesized and biotinylated at Illumina, Inc. Target capture was performed using Illumina TruSight™ Rapid Capture Kit according to manufacturer's instructions except that customized capture probes were used, and hybridization and wash steps were performed at 48 C.

The products of the capture step were sequenced on an Illumina HiSeq 2500 Sequencer using 2×100 cycle runs, with four samples in rapid run mode, according to manufacturer's instructions.

Bioinformatic Analysis

FASTQ sequences were demultiplexed followed by in silico demethylation whereby all C's on read 1 were converted to T's and all G's on read 2 were converted to A's. Subsequently, these "demethylated" FASTQ sequences were aligned using BWA (v 0.7.10-r789) to an index comprising a "demethylated" hg19 genome. BWA alignment is described in Li and Durbin (2010) Fast and accurate long-read alignment with Burrows-Wheeler Transform. Bioinformatics, Epub. [PMID: 20080505], which is incorporated herein by reference. Following alignment, the "demethylated" FASTQ sequences were replaced with the original FASTQ sequences. Methylation levels were calculated as the fraction of 'C' bases at a target CpG site out of 'C'+'T' total bases.

Following calculation of methylation levels at each CpG site for each sample and replicate, aggregate coverage-weighted normalized methylation difference z-scores were calculated as follows.

(1) the methylation level at each CpG site was normalized by subtracting the mean methylation level in baseline and dividing by the standard deviation of methylation levels in baseline to obtain a per-site z-score. Specifically, the normalized methylation difference at each CpG site was determined according to the formula:

$$Z_i = \frac{\chi_i - \mu_i}{\sigma_i}$$

where $Z_i$ represents a normalized methylation difference for a particular site identified as i, $\chi_i$ represents the methylation level at site i in the test genomic DNA, $\mu_i$ represents the mean methylation level at site i in the reference genome, and $\sigma_i$ represents the standard deviation of methylation levels at site i in the reference genomic DNA.

(2) the z-score at each CpG site was multiplied by the coverage observed at the CpG site, and the coverage-weighted z-score was then summed across all CpG sites and then divided by the sum of the coverage squared at each CpG site. More specifically, an aggregate coverage-weighted methylation difference z-score (an example of an aggregate coverage-weighted normalized methylation difference score, A) was determined according to the formula:

$$A = \frac{\sum_{i=1}^{k} w_i Z_i}{\sqrt{\sum_{i=1}^{k} w_i^2}}$$

where $w_i$ represents the coverage at site i and k represents the total number of sites.

Results

Figure 3:
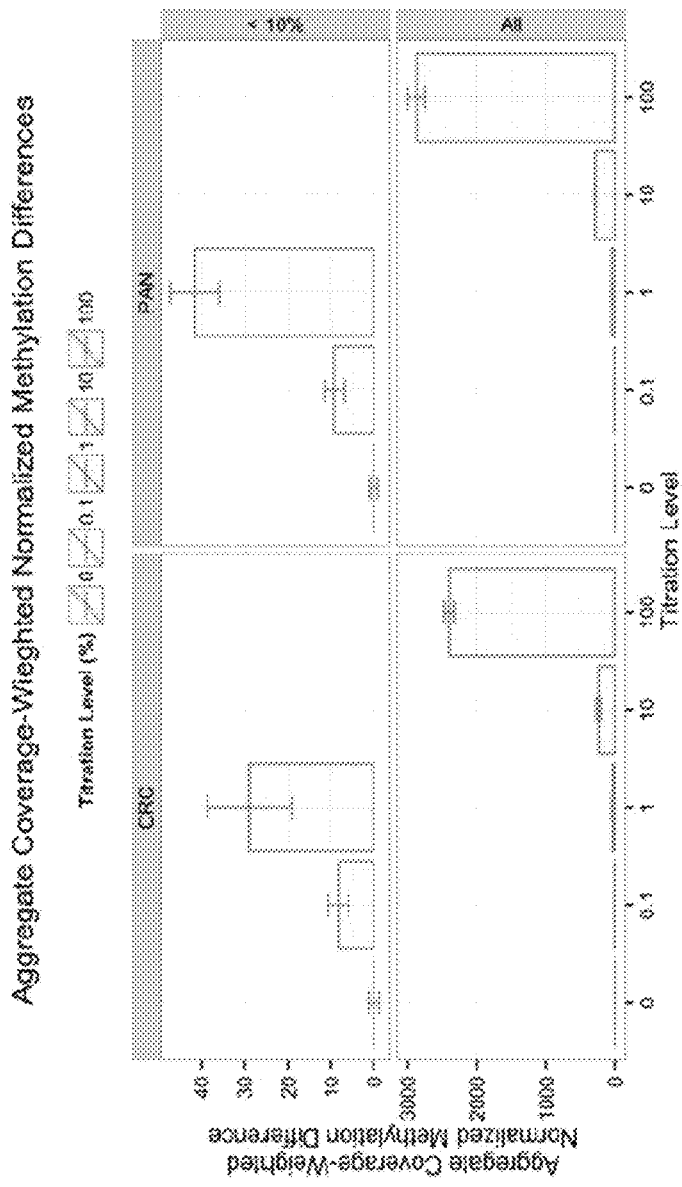
FIG. 3 shows aggregate coverage-weighted normalized methylation differences (z-scores) determined as described herein for various cancer samples at various titration levels.

A titration experiment was performed to demonstrate analytical sensitivity using a colorectal cancer cell line LS1034 and a normal cell line NA12878. Namely, targeted ctDNA methylation sequencing was performed in triplicates using both the Pan-Cancer and CRC panels on 0.1%, 1%, and 10% titrations of LS1034 into NA12878 along with pure LS1034 and pure NA12878. For each of the 15 sample replicates, the aggregate coverage-weighted methylation difference z-scores were calculated using the normal NA12878 samples as the baseline (FIG. 3). The results indicate that the within sample variation is far less than the variation between titration levels. In particular, the clear separation of the 0.1% titration of LS1034 into NA12878 from the NA12878 sample indicates the assay and accompanying aggregate coverage-weighted methylation difference z-score can achieve a 0.1% limit of detection.

Results obtained using the methods of this example provide high sensitivity evaluation of the cumulative effect of multiple affected CpG sites across the genome. By providing a method for detecting methylation patterns the methods of this example can provide improved cancer diagnosis than methods that rely on detection of somatic mutations, as evidenced by the improved concordance in alternations between CRC tissue and corresponding plasma when evaluating DNA methylation markers compared to somatic mutations (see, for example, Danese et al., "Comparison of Genetic and Epigenetic Alterations of Primary Tumors and Matched Plasma Samples in Patients with Colorectal Cancer" PLoS ONE 10(5):e0126417. doi: 10.1371/journal.pone.0126417 (2015), which is incorporated herein by reference). The methods described in this example also provide identification of tissue origin for cancer. Specifically, tissue specific methylation markers have been shown to be useful to trace the tissue origin of particular ctDNA sequences (see, for example, Sun et al. "Plasma DNA tissue mapping by genome-wide methylation sequencing for noninvasive prenatal, cancer, and transplantation assessments" Proc. Natl. Acad. Sci, USA 112 (40) E5503-E5512 (2015), which is incorporated herein by reference).

Example II

Analytical Sensitivity of ctDNA Methylation-Based Cancer Detection Using Coverage-Weighted Methylation Scores This example describes an alternative highly sensitive assay for detecting methylation in circulating tumor DNA (ctDNA). The assay described in this example also can be useful for cancer screening, monitoring disease progression, or evaluating a patient's response to a therapeutic treatment.

Targeted Capture Probe Design

For this study, the two targeted methylation panels described in Example I were pooled together. The Pan-Cancer Panel targets 9,921 affected CpG sites in 20 major cancer types as selected from The Cancer Genome Atlas Database. The CpG sites included in the Pan-Cancer Panel are listed in Table I. The CRC Panel targets 1,162 affected CpG sites in colorectal cancer. The CpG sites included in the CRC Panel are listed in Table II. The combined CpG sites listed in Table I and Table II refer to Genome Build 37.

The probe sequences for the CpG sites were selected from the Infinium HM450 array (Illumina, Inc., San Diego, Calif.). Design principles for the probes are shown in FIG. 1. Two probes were used for targets having greater than 4 CpG sites, including a completely methylated probe (having a G nucleotides that complements the C position of each CpG site) and completely unmethylated probe (having an A nucleotide that complements the U that is expected to result from bisulfite conversion of each of the C positions of a CpG site) as shown in FIG. 1. In contrast, only one probe was used for targets having 4 or fewer CpG sites (the probe includes degenerate nucleotide R, complementary to U or C, at the C position of each CpG site).

Isolation and Extraction of cfDNA from Plasma

Plasma samples were obtained from human blood draws. Cell free DNA (cfDNA) was extracted using the QIAamp Circulating Nucleic Acid Kit (Qiagen, Hilden, Germany). Targeted ctDNA methylation sequencing was carried out according to the workflow shown in FIG. 2, and as set forth below in the context of evaluating titration and detection sensitivity.

Titration and Detection Sensitivity

As described above, NA12878 genomic DNA was purchased from Coriell Institute (Coriell Institute, Camden, N.J.), and LS1034 genomic DNA was purchased from ATCC (ATCC, Manassas, Va.). Genomic DNA was fragmented using Covaris M200 (Covaris, Woburn, Mass.) and size-selected to 130-250 bp using BluePippin (Sage Science, Beverly, Mass.) to simulate the size distribution of cfDNA. DNA quantification was performance using Quant-iT™ PicoGreen® dsDNA Assay Kit (ThermoFisher Scientific, Grand Island, N.Y.). 10%, 1%, or 0.1% LS1034 DNA was spiked into NA12878 DNA background to make the DNA mixtures. 30 ng of each mixture, 100% NA12878, or 100% LS1034 DNA was used in library preparation. Three replicated libraries were generated for each titration level. A set of six replicates of NA12878 was used as the baseline reference genome.

Extracted cfDNA or sheared and size-selected genomic DNA was bisulfite treated and purified using EZ DNA Methylation-Lightning Kit (Zymo Research, Irvine, Calif.).

Bisulfite-seq Libraries were prepared using the Accel-NGS® Methyl-Seq DNA Library Kit (Swift Biosciences, Ann Arbor, Mich.).

Targeted capture was carried out on the bisulfite-seq libraries using probes that were complementary to fragments having the CpG sites listed in Table I or Table II. Capture probes were synthesized and biotinylated at Illumina, Inc. Target capture was performed using Illumina TruSight™ Rapid Capture Kit according to manufacturer's instructions except that customized capture probes were used, and hybridization and wash steps were performed at 48 C.

The products of the capture step were sequenced on an Illumina HiSeq 2500 Sequencer using 2×100 cycle runs, with four samples in rapid run mode, according to manufacturer's instructions.

Bioinformatic Analysis

FASTQ sequences were demultiplexed followed by in silico demethylation whereby all C's on read 1 were converted to T's and all G's on read 2 were converted to A's. Subsequently, these "demethylated" FASTQ sequences were aligned using BWA (v 0.7.10-r789) to an index comprising a "demethylated" hg19 genome. BWA alignment is described in Li and Durbin (2010) Fast and accurate long-read alignment with Burrows-Wheeler Transform. Bioinformatics, Epub. [PMID: 20080505], which is incorporated herein by reference. Following alignment, the "demethylated" FASTQ sequences were replaced with the original FASTQ sequences. Methylation levels were calculated as the fraction of 'C' bases at a target CpG site out of 'C'+'T' total bases.

After calculation of methylation levels at each CpG site for each sample and replicate, coverage-weighted methylation scores were calculated as follows.

(1) The methylation level at each CpG site was normalized by subtracting the mean methylation level in baseline and dividing by the standard deviation of methylation levels in the baseline to obtain a per-site z-score. Specifically, the normalized methylation difference at each CpG site was determined according to the formula:

$$Z_i = \frac{\chi_i - \mu_i}{\sigma_i}$$

where $Z_i$ represents a normalized methylation difference for a particular site identified as i, $\chi_i$ represents the methylation level at site i in the test genomic DNA, $\mu_i$ represents the mean methylation level at site i in the reference genome, and $\sigma_i$ represents the standard deviation of methylation levels at site i in the reference genomic DNA.

(2) The z-score for each CpG site i ($Z_i$) was converted into the probability of observing such a z-score or greater by converting the z-score into a one-sided p-value ($p_i$). Probabilities were calculated assuming a normal distribution, although other distributions (e.g., t-distribution or binomial distribution) may be used as well.

(3) The p-value at each CpG site was weighted by multiplying the p-value at each CpG site i ($p_i$) by the coverage observed at the CpG site ($w_i$), and a coverage-weighted methylation score (MS) was determined by combining the weighted p-values according to the formula:

$$MS = -2\sum_{i=1}^{k} \ln(w_i p_i)$$

where $p_i$ represents the one-sided p-value at site i, k represents the total number of sites, and $w_i$ represents the coverage at site i.

Results

Figure 4:
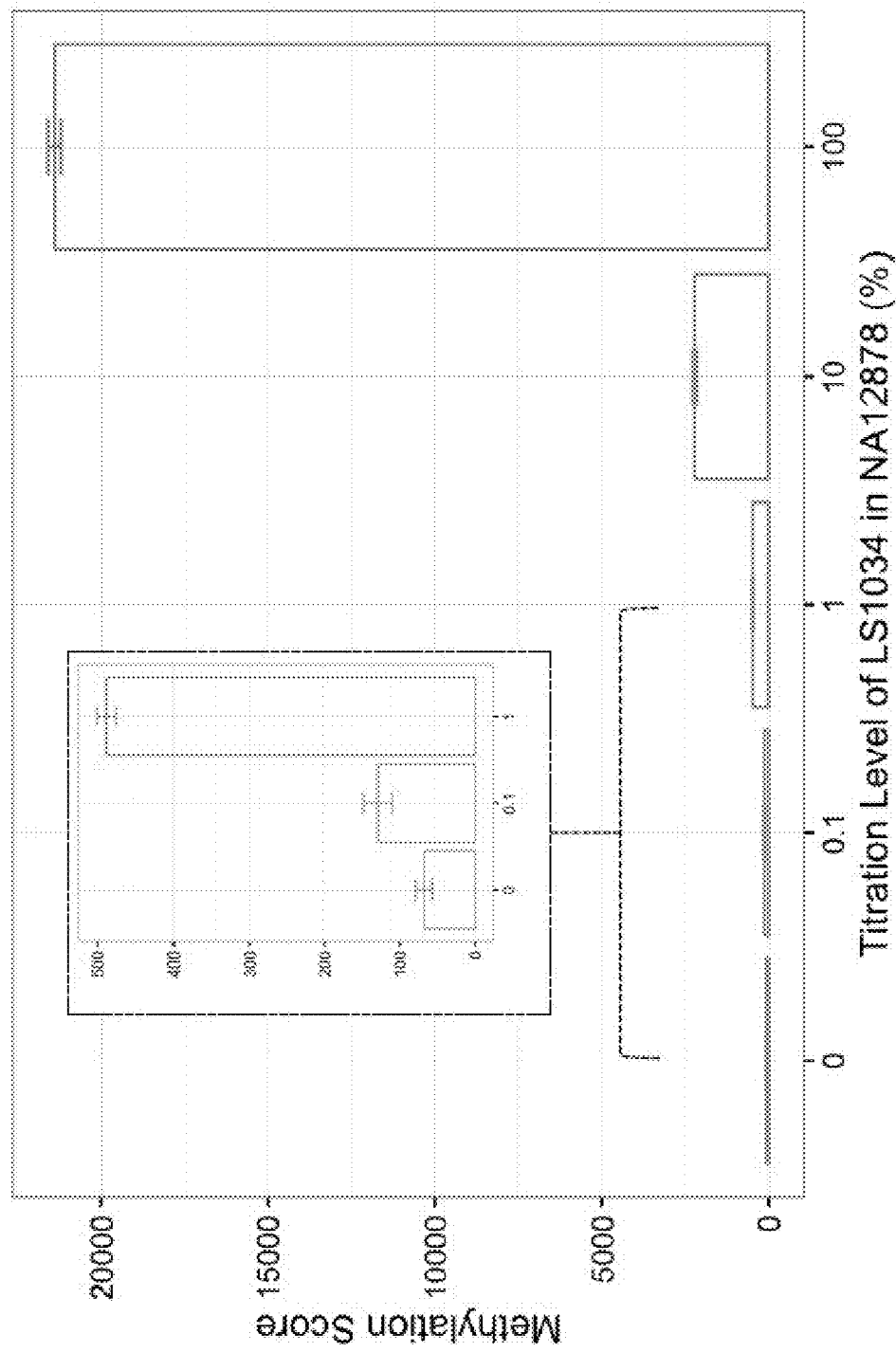
FIG. 4 shows coverage-weighted methylation scores determined as described herein for colorectal cancer samples at various titration levels.

A titration experiment was performed to demonstrate analytical sensitivity using a colorectal cancer cell line LS1034 and a normal cell line NA12878. Namely, targeted ctDNA methylation sequencing was performed in triplicates using the combined Pan-Cancer and CRC panels on 0.1%, 1%, and 10% titrations of LS1034 into NA12878 along with pure LS1034 and pure NA12878. For each of the 15 sample replicates, the coverage-weighted methylation scores were calculated using the normal NA12878 samples as the baseline (FIG. 4). The results indicate that the within sample variation is far less than the variation between titration levels. In particular, the clear separation of the 0.1% titration of LS1034 into NA12878 from the NA12878 sample indicates the assay and accompanying coverage-weighted methylation score can achieve a 0.1% limit of detection (see inset of FIG. 4).

Similar to the results in Example I, results obtained using the methods of this example provide high sensitivity evaluation of the cumulative effect of multiple affected CpG sites across the genome. By providing an alternative method for detecting methylation patterns, the methods of this example can provide a more sensitive cancer diagnosis than methods relying on detection of somatic mutations.

Example III

Clinical Performance of ctDNA Methylation-Based Cancer Detection Using Normalized Coverage-Weighted Methylation Score Differences This example evaluates clinical sensitivity and specificity of the methylation-based cancer detection in circulating tumor DNA (ctDNA) using normalized coverage weighted methylation score differences. As noted above, the assay described in this example can be useful for cancer screening, monitoring disease progression, or evaluating a patient's response to a therapeutic treatment.

Targeted Capture Probe Design

For this study, the two targeted methylation panels described in Example I were pooled together. The Pan-Cancer Panel targets 9,921 affected CpG sites in 20 major cancer types as selected from The Cancer Genome Atlas Database. The CpG sites included in the Pan-Cancer Panel are listed in Table I. The CRC Panel targets 1,162 affected CpG sites in colorectal cancer. The CpG sites included in the CRC Panel are listed in Table II. The combined CpG sites listed in Table I and Table II refer to Genome Build 37.

The probe sequences for the CpG sites were selected from the Infinium HM450 array (Illumina, Inc., San Diego, Calif.). Design principles for the probes are shown in FIG. 1. Two probes were used for targets having greater than 4 CpG sites, including a completely methylated probe (having a G nucleotides that complements the C position of each CpG site) and completely unmethylated probe (having an A nucleotide that complements the U that is expected to result from bisulfite conversion of each of the C positions of a CpG site) as shown in FIG. 1. In contrast, only one probe was used for targets having 4 or fewer CpG sites (the probe includes degenerate nucleotide R, complementary to U or C, at the C position of each CpG site).

Blood Sample Collection and Processing

Cancer patients were recruited at MD Anderson Cancer Center (Houston, Tex.). A total of 70 blood samples collected from 63 late stage cancer patients of three cancer types were used in this study (n=30 for colorectal cancer (CRC), n=14 for breast cancer (BRCA), n=19 for lung cancer). Four CRC patients had blood samples collected at multiple time points. Three breast cancer samples and one colorectal cancer sample failed sample quality control and therefore were excluded from the analysis, resulting in the final set of 66 cancer samples (36 CRC, 11 BRCA, and 19 lung), representing 59 different patients (29 CRC, 11 BRCA, and 19 lung). A total of 65 normal blood samples were collected from healthy subjects to be used as baseline methylation controls (20), training controls (20) and testing controls (25) as described herein.

Plasma was separated by centrifugation at 1600 G for 10 minutes. The supernatant was transferred to 15 mL centrifuge tubes and centrifuged at room temperature for 10 minutes at 3000 G. The supernatant was transferred to a fresh 15 mL centrifuge tube and stored in a freezer (−80° C.) and shipped on dry ice. Plasma samples from healthy donors were obtained from BioreclamationIVT (Westbury, N.Y.). All samples were de-identified.

Isolation and Extraction of cfDNA from Plasma

Cell free DNA (cfDNA) was extracted using the QIAamp Circulating Nucleic Acid Kit (Qiagen, Hilden, Germany). Targeted ctDNA methylation sequencing was carried out according to the workflow shown in FIG. 2, and as set forth below in the context of evaluating titration and detection sensitivity.

Targeted Bisulfite Sequencing Library Preparation and Sequencing cfDNA was bisulfite treated and purified using EZ DNA Methylation-Lightning Kit (Zymo Research, Irvine, Calif.).

Whole genome amplification of bisulfite-converted DNA was performed using Accel-NGS® Methyl-Seq DNA Library Kit (Swift Biosciences, Ann Arbor, Mich.).

Targeted capture was carried out on the bisulfite-seq libraries using probes that were complementary to fragments having the CpG sites listed in Tables I and II. Capture probes were synthesized and biotinylated at Illumina, Inc. (San Diego, Calif.). Target capture was performed using Illumina TruSight™ Rapid Capture Kit according to manufacturer's instructions. Hybridization and wash conditions were modified to yield optimal capture efficiency.

The products of the capture step were sequenced on an Illumina Hiseq2500 Sequencer using 2×100 cycle runs, with four samples in rapid run mode, according to manufacturer's instructions.

Bioinformatic Analysis

FASTQ sequences were demultiplexed followed by in silico demethylation whereby all C's on read 1 were converted to T's and all G's on read 2 were converted to A's. Subsequently, these "demethylated" FASTQ sequences were aligned using BWA (v 0.7.10-r789) to an index comprising a "demethylated" hg19 genome. BWA alignment is described in Li and Durbin (2010) Fast and accurate long-read alignment with Burrows-Wheeler Transform. Bioinformatics, Epub. [PMID: 20080505], which is incorporated herein by reference. Following alignment, the "demethylated" FASTQ sequences were replaced with the original FASTQ sequences. Methylation levels were calculated as the fraction of 'C' bases at a target CpG site out of 'C'+'T' total bases.

After calculation of methylation levels at each CpG site for each sample and replicate, coverage-weighted methylation scores were calculated as follows.

(1) Methylation scores were initially determined for the training set of 20 normal genomic DNA samples. First, a normalized methylation difference (z-score) at a particular site i (e.g., CpG site) was determined according to the formula:

$$Z_i = \frac{\chi_i - \mu_i}{\sigma_i}$$

wherein $Z_i$ represents a normalized methylation difference for a particular site identified as i, $\chi_i$ represents the methylation level at site i in a member of the training set of normal genomic DNA, $\mu_i$ represents the mean methylation level at site i in the baseline samples, and $\sigma_i$ represents the standard deviation of methylation levels at site i in the baseline samples.

(2) The z-score for each CpG site i ($Z_i$) was converted into the probability of observing such a z-score or greater by converting the z-score into a one-sided p-value ($p_i$). Probabilities were calculated assuming a normal distribution, although other distributions (e.g., t-distribution or binomial distribution) may be used as well.

(3) The p-value at each CpG site was weighted by multiplying the p-value at each CpG site i ($p_i$) by the coverage observed at the CpG site ($w_i$), and a coverage-weighted methylation score (MS) was determined by combining the weighted p-values according to the formula:

$$MS = -2\sum_{i=1}^{k} \ln(w_i p_i)$$

wherein $p_i$ represents the one-sided p-value at site i, k represents the total number of sites, and $w_i$ represents the significance, for instance coverage, of the site i.

(4) Statistical analysis of the training set methylation scores was then performed. The mean methylation score ($\mu_{MS}$) and standard deviation of methylation scores ($\sigma_{MS}$) in the training set of normal genomic DNA were calculated, characterizing the distribution of the methylation score in a normal population.

(5) Next, methylation scores were determined for the 66 cancer genomic DNA samples and 25 testing controls. First, a normalized methylation difference (z-score) at each CpG site was determined according to the formula:

$$Z_i = \frac{\chi_i - \mu_i}{\sigma_i}$$

where $Z_i$ represents a normalized methylation difference for a particular site identified as i, $\chi_i$ represents the methylation level at site i in the test genomic DNA, $\mu_i$ represents the mean methylation level at site i in the reference genome, and $\sigma_i$ represents the standard deviation of methylation levels at site i in the reference genomic DNA.

(6) The z-score for each CpG site i ($Z_i$) was converted into the probability of observing such a z-score or greater by converting the z-score into a one-sided p-value ($p_i$). Probabilities were calculated assuming a normal distribution, although other distributions (e.g., t-distribution or binomial distribution) may be used as well.

(7) The p-value at each CpG site was weighted by multiplying the p-value at each CpG site i ($p_i$) by the coverage observed at the CpG site ($w_i$), and a coverage-weighted methylation score (MS) was determined by combining the weighted p-values according to the formula:

$$MS = -2\sum_{i=1}^{k} \ln(w_i p_i)$$

where $p_i$ represents the one-sided p-value at site i, k represents the total number of sites, and $w_i$ represents the coverage at site i.

(8) Finally, the methylation scores of the test genomic DNA samples were evaluated against the distribution of methylation scores determined for the training set population, represented by the mean methylation score ($\mu_{MS}$) and standard deviation of methylation scores ($\sigma_{MS}$) for the training set of normal genomic DNA. The number of standard deviations between the methylation score for the test genomic DNA and the methylation score mean ($\mu_{MS}$) of the training set of normal genomic DNA was determined according to the formula:

$$Z_{MS} = \frac{MS - \mu_{MS}}{\sigma_{MS}}$$

wherein $Z_{MS}$ represents a normalized methylation score difference, MS represents the methylation score of the test sample, $\mu_{MS}$ represents the mean methylation score for the training set of normal genomic DNA, and $\sigma_{MS}$ represents the standard deviation of methylation scores for the training set of normal genomic DNA. A $Z_{MS}$ value greater than 3 standard deviations was used as a threshold to identify cancer samples.

Results

Figure 5:
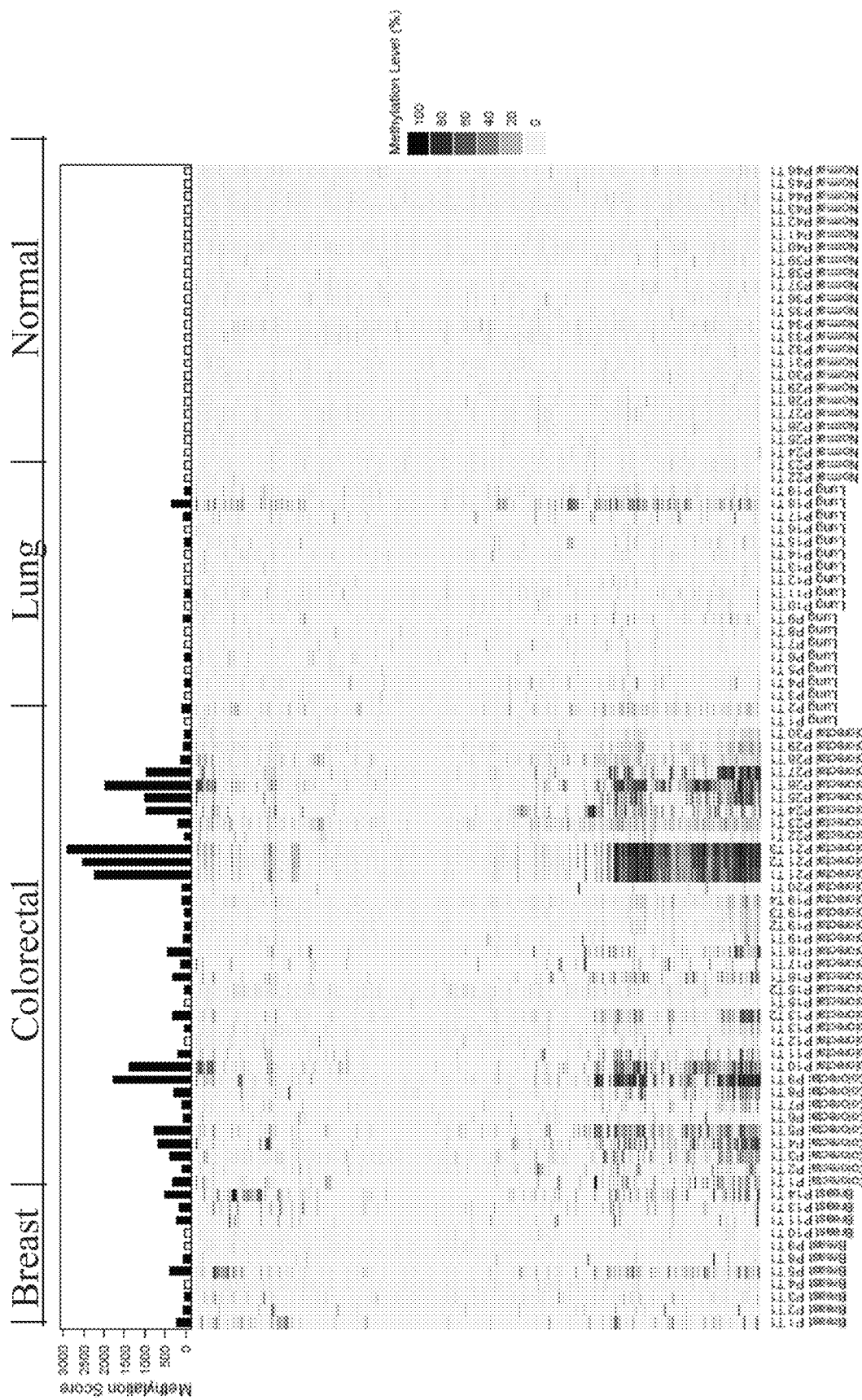
FIG. 5 shows methylation scores for 66 samples from advanced cancer patients and 25 samples from normal individuals, demonstrating the ability of the methylation score algorithm to distinguish advanced cancer samples from normal samples.

As noted above, the purpose of this experiment was to evaluate the clinical performance of the normalized coverage-weighted methylation score difference algorithm, including its clinical sensitivity and specificity. The 66 cancer samples and 25 normal samples were subjected to the methylation score analysis as described herein, including determining the z-score for each of the CpG sites listed in Tables I and II, converting the z-score into a one-sided p-value based on a normal distribution assumption, weighting the p-values by coverage, and aggregating the individual weighted p-values into a single methylation score using the Fisher formula. The resulting methylation scores were used to distinguish the cancer samples from the normal samples. FIGS. 5 and 6 show that the normalized coverage-weighted methylation score difference algorithm was able to detect 34 out of 36 CRC samples (94.4% sensitivity), 8 out of 11 BRCA samples (72.7% sensitivity), and 10 out of 19 lung cancer samples (52.6% sensitivity). The algorithm exhibited 100% specificity, having correctly identified all 25 of the testing control samples as normal.

Results obtained using the methods of this example provide highly sensitive and specific evaluation of the cumulative effect of multiple affected CpG sites across the genome. By providing an alternative method for detecting methylation patterns, the methods of this example can provide a more sensitive and specific cancer diagnosis than methods relying on detection of somatic mutations.

Example IV

Clinical Performance of Cancer Type Classification Method Based on Average Methylation Levels Across Preselected Subsets of Methylation Sites This example evaluates the clinical sensitivity of a method for cancer type classification based on average methylation levels across preselected subsets of CpG methylation sites referred to herein as "hypermethylated" sites. The assay described in this example can be useful for identifying the source of tumor in circulating cell-free DNA. Correlation of Methylation Profiles Between Plasma and Tissue DNA Samples As an initial inquiry, we set out to determine how well the methylation profiles of circulating tumor DNA (ctDNA) isolated from plasma samples correlated to those of DNA isolated from tumor tissues. A high degree of correlation would lend credence to the idea that methylation profiles of cfDNA can be used to classify the tumor of origin. To this end, we compared the methylation profiles of the colorectal, breast and lung cancer samples that were detected in Example III to the average methylation profiles for each of the 32 cancer types from TCGA (The Cancer Genomic Atlas) that had a minimum of 30 cancer samples in the database. The methylation profiles were determined substantially as described in Examples I-III and consisted of methylation levels at 9,242 CpG sites (poorly performing methylation sites from the original CpG panels were filtered out to improve accuracy).

Figure 7:
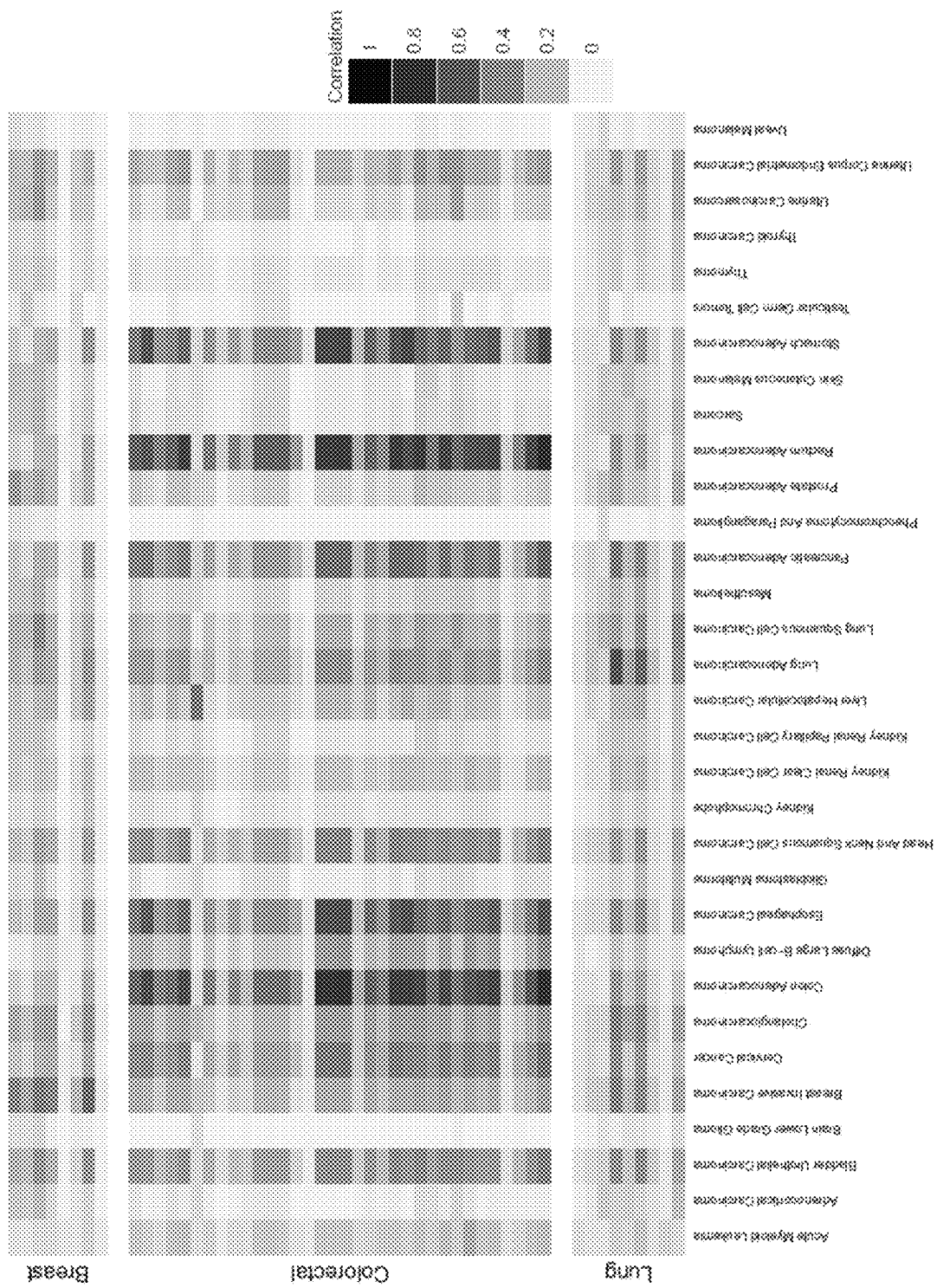
FIG. 7 shows correlation of methylation profiles between plasma and tissue DNA samples from cancer patients.

The comparison was performed in a pairwise manner between each cancer-positive plasma sample from Example III and each of the 32 cancer type from TCGA, resulting in correlation coefficients ranging from 0 to 1. The correlations were plotted as a two-dimensional correlation map, which is shown in FIG. 7. The darker areas of the map correspond to higher correlations, whereas the lighter areas of the map signify lower correlations. The observed correlations between the methylation profiles were generally highest for the matching tumor types. For example, in the breast cancer samples from plasma, the correlation was highest to the breast cancer tissue (breast invasive carcinoma), and lower in all other tumor tissue types. Similarly, for the CRC plasma samples, the correlation was highest to colon and rectum tissues (e.g., colon adenocarcinoma, esophageal carcinoma, rectum adenocarcinoma and stomach adenocarcinoma). The correlation was less pronounced in the lung cancer samples. Development and Testing of Cancer Type Classification Having determined that there is a significant correlation between methylation profiles of ctDNA and DNA from tumor tissues, we proceeded to develop and test a cancer type classification method in silico.

First, we identified 24 cancer types with more than 100 samples in the TCGA database. For each of these types, we created a list of "hypermethylated" sites, which were defined as sites having a mean methylation level (across samples) in the top 3% across the entire panel and greater than 6% in terms of absolute values.

Given a test sample, we determined its cancer types in a three-step process. First, for each of the 24 cancer types, the methylation levels for each of the "hypermethylated" sites on the list were determined as described in Examples I-III. Next, the average methylation level across the "hypermethylated" sites were calculated for each of the 24 cancer types. Finally, each of the 24 cancer types was ranked by their average methylation levels across the "hypermethylated" sites and classified the test sample by the cancer type with the highest average methylation level.

Figure 8:
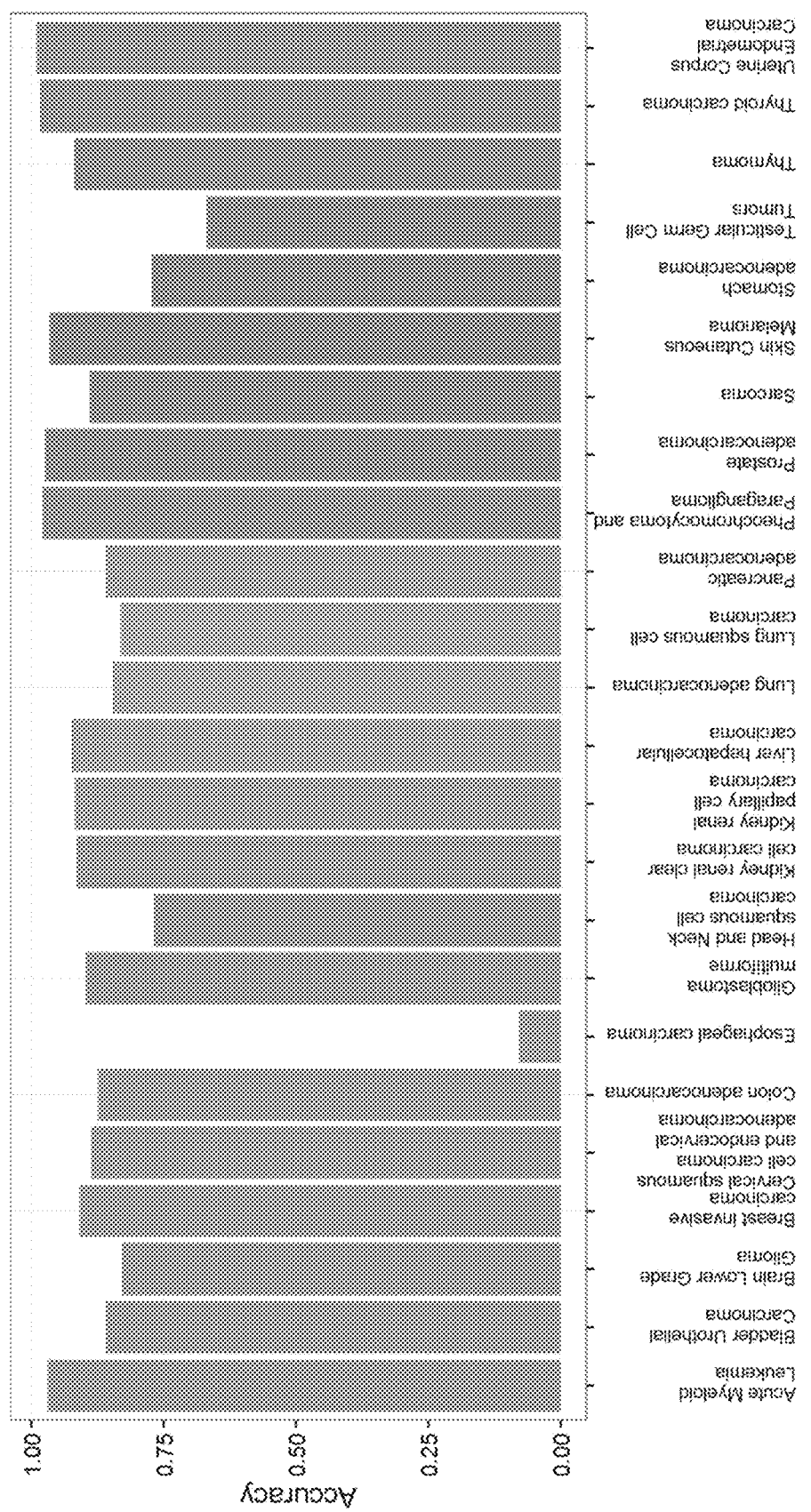
FIG. 8 shows cancer type classification results on tumor tissue samples, demonstrating the ability of the cancer type classification algorithm to identify most tumors based on DNA methylation data with a high degree of accuracy.

We then proceeded to back-test the method on each of the TCGA tissue samples that was used to generate the lists of "hypermethylated" sites. Accuracy of the method was defined as the ratio of the number of cancer samples of a particular type that were identified correctly to the total number of samples of that cancer type. Results of this analysis are shown in FIG. 8. As one can easily see from this figure, 22 out of 24 cancer types were classified with over 75% accuracy. Indeed, many of the cancer types were correctly identified about 90% of the time or better. Only two types—esophageal carcinoma and testicular germ cell tumors—failed to cross the 75% threshold.

Cancer Type Classification of Plasma Samples

The 52 plasma samples correctly identified as cancer samples in Example III (34 CRC, 8 BRCA, and 10 lung) were subjected to the cancer type classification analysis as described above. Results of this analysis are shown in FIG. 9. The cancer classification algorithm correctly identified 28 out of 34 CRC samples (82%), 7 out of 8 BRCA samples (88%) and 7 out of 10 lung cancer samples (70%). These results demonstrate that the cancer type classification method described herein may be used with a high clinical sensitivity to identify the tissue of origin in ctDNA from plasma samples.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method for monitoring for relapse of a tumor in an individual treated for cancer, comprising
   (a) providing a cell free DNA sample from plasma comprising a mixture of circulating tumor and non-tumor DNA obtained from the individual at a first time point after initiation of cancer treatment, thereby providing test genomic DNA;
   (b) detecting methylation states for a plurality of CpG sites in the test genomic DNA;
   (c) determining the coverage at each of the CpG sites for the detecting of the methylation states;
   (d) providing methylation states for the plurality of CpG sites in reference genomic DNA from at least one reference individual;
   (e) determining, for each of the CpG sites, the methylation difference between the test genomic DNA and the reference genomic DNA, thereby providing a normalized methylation difference for each CpG site;
   (f) weighting the normalized methylation difference for each CpG site by the coverage at each of the CpG sites, thereby determining an aggregate coverage-weighted normalized methylation difference score;
   (g) repeating steps (a) through (f) using a second test genomic DNA provided from plasma comprising a mixture of circulating tumor and non-tumor DNA obtained from the individual at a second time point after initiation of cancer treatment, and using the same reference genomic DNA from the at least one reference individual;
   (h) determining that a change has occurred in the aggregate coverage-weighted normalized methylation difference score between the test genomic DNA and the second test genomic DNA; wherein said change is indicative of relapse of said tumor in said individual, and
   (i) treating the individual with a therapy to reduce the relapse, wherein the therapy comprises surgery, chemotherapy, or radiation therapy.

2. The method of claim 1, wherein the providing of the sample in step (a) comprises targeted selection of a subset of genomic DNA fragments comprising a set of predetermined target CpG sites.

3. The method of claim 2, wherein the providing of the sample in step (a) further comprises treating the subset of genomic DNA fragments with bisulfate.

4. The method of claim 1, wherein the detecting in step (b) comprises a sequencing technique that serially distinguishes nucleotides in the test genomic DNA.

5. The method of claim 4, wherein the sequencing technique comprises massively parallel sequencing.

6. The method of claim 1, wherein the normalized methylation difference at a particular CpG site is determined according to $$Z_i = \frac{\chi_i - \mu_i}{\sigma_i}$$

wherein $Z_i$ represents a normalized methylation difference for a particular CpG site identified as i, $\chi_i$ represents the methylation level at CPG site i in the test genomic DNA, $\mu_i$ represents the mean methylation level at CpG site i in the reference genome, and $\sigma_i$ represents the standard deviation of methylation levels at CpG site i in the reference genomic DNA.

7. The method of claim 6, wherein the aggregate coverage-weighted normalized methylation difference score (represented as A) is determined according to $$A = \frac{\sum_{i=1}^{k} w_i Z_i}{\sqrt{\sum_{i=1}^{k} w_i^2}}$$

wherein $w_i$ represents the coverage at CpG site i, and k represents the total number of CpG sites.

8. The method of claim 1, wherein the test sample is from an individual known or suspected to have cancer.

9. The method of claim 1, wherein the test organism is a human.

10. The method of claim 9, wherein the method further comprises communicating counseling information to the human.

11. The method of claim 1, wherein the detecting in step (b) comprises:
   (b1) treating the test genomic DNA with bisulfite to generate bisulfite treated DNA;
   (b2) enriching for a subset of fragments of the bisulfite treated DNA by targeted selection, the subset comprising a set of predetermined target CpG sites;
   (b3) performing massively parallel sequencing of the subset to generate sequence reads; and
   (b4) aligning the sequence reads to a reference.

12. The method of claim 11, wherein the subset comprises at least 100 predetermined target CpG sites.

13. The method of claim 11, wherein the subset comprises at least 1000 predetermined target CpG sites.

14. The method of claim 11, wherein the massively parallel sequencing generates at least 10,000 sequence reads.

* * * * *

UNITED STATES PATENT AND TRADEMARK OFFICE
CERTIFICATE OF CORRECTION

PATENT NO. : 11,319,593 B2
APPLICATION NO. : 15/380348
DATED : May 3, 2022
INVENTOR(S) : Toung et al.

It is certified that error appears in the above-identified patent and that said Letters Patent is hereby corrected as shown below:

In the Claims

Claim 3, Line 47 delete "bisulfate." and insert -- bisulfite. --.

Claim 6, Line 65 delete "$\sigma_i$," and insert -- $\sigma_i$ --.

Signed and Sealed this
Sixth Day of September, 2022

*Katherine Kelly Vidal*
*Director of the United States Patent and Trademark Office*